United States Patent
Kumar et al.

(10) Patent No.: US 11,993,613 B2
(45) Date of Patent: May 28, 2024

(54) THIAZOLO[5,4-B]PYRIDINE MALT-1 INHIBITORS

(71) Applicant: AbbVie Inc., North Chicago, IL (US)

(72) Inventors: Puneet Kumar, Santa Clara, CA (US); Anthony Mastracchio, Libertyville, IL (US); Mark Mills, Nottingham (GB); Andrew William Phillips, Nottingham (GB)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 18/192,810

(22) Filed: Mar. 30, 2023

(65) Prior Publication Data

US 2023/0312601 A1    Oct. 5, 2023

Related U.S. Application Data

(60) Provisional application No. 63/362,302, filed on Mar. 31, 2022.

(51) Int. Cl.
*A61P 35/00* (2006.01)
*C07D 513/04* (2006.01)

(52) U.S. Cl.
CPC ............ *C07D 513/04* (2013.01); *A61P 35/00* (2018.01)

(58) Field of Classification Search
CPC .............................. C07D 513/04; A61P 35/00
See application file for complete search history.

(56) References Cited

U.S. PATENT DOCUMENTS

| | | | |
|---|---|---|---|
| 4,492,692 A | 1/1985 | Jung et al. | |
| 5,646,128 A | 7/1997 | Firestein et al. | |
| 5,658,889 A | 8/1997 | Gruber et al. | |
| 5,726,302 A | 3/1998 | Ugarkar et al. | |
| 5,795,977 A | 8/1998 | Ugarkar et al. | |
| 5,851,741 A | 12/1998 | Takahashi et al. | |
| 6,251,911 B1 | 6/2001 | Bold et al. | |
| 7,560,553 B1 | 7/2009 | Kelleher-Andersson et al. | |
| 7,625,922 B2 | 12/2009 | Niculescu-Duvaz et al. | |
| 7,709,471 B2 | 5/2010 | Halsall et al. | |
| 8,377,945 B2 | 2/2013 | Zhang et al. | |
| 8,466,186 B2 | 6/2013 | Priepke et al. | |
| 8,586,604 B2 | 11/2013 | Priepke et al. | |
| 8,637,532 B2 | 1/2014 | Sutton et al. | |
| 8,674,113 B2 | 3/2014 | Priepke et al. | |
| 8,703,938 B2 | 4/2014 | Or et al. | |
| 8,759,332 B2 | 6/2014 | Qiu et al. | |
| 8,759,537 B2 | 6/2014 | Priepke et al. | |
| 8,815,928 B2 | 8/2014 | Or et al. | |
| 8,822,700 B2 | 9/2014 | Qiu et al. | |
| 8,921,405 B2 | 12/2014 | Pfau et al. | |
| 8,927,709 B2 | 1/2015 | Qiu et al. | |
| 9,040,560 B2 | 5/2015 | Sutton et al. | |
| 9,096,545 B2 | 8/2015 | Gharat et al. | |
| 9,145,415 B2 | 9/2015 | Takasaki et al. | |
| 9,266,874 B2 | 2/2016 | Ho et al. | |
| 9,439,890 B2 | 9/2016 | Gharat et al. | |
| 9,725,445 B2 | 8/2017 | Childers et al. | |
| 9,949,955 B2 | 4/2018 | Gharat et al. | |
| 9,987,278 B2 | 6/2018 | Naoe et al. | |
| 10,030,005 B2 | 7/2018 | Brubaker et al. | |
| 10,030,034 B2 | 7/2018 | Ho et al. | |
| 10,351,548 B2 | 7/2019 | Sestito et al. | |
| 10,391,083 B2 | 8/2019 | Gharat et al. | |
| 10,584,114 B2 | 3/2020 | Brubaker et al. | |
| 10,604,533 B2 | 3/2020 | Ho et al. | |
| 10,626,081 B2 | 4/2020 | Smith et al. | |
| 10,662,195 B2 | 5/2020 | Singh et al. | |
| 10,821,100 B2 | 11/2020 | Gharat et al. | |
| 10,844,044 B2 | 11/2020 | Alvarado et al. | |
| 10,933,068 B2 | 3/2021 | Rickard et al. | |
| 11,040,976 B2 | 6/2021 | Maianti et al. | |

(Continued)

FOREIGN PATENT DOCUMENTS

| | | |
|---|---|---|
| CN | 112409331 A | 2/2021 |
| CN | 113527291 A | 10/2021 |

(Continued)

OTHER PUBLICATIONS

Butcher A., et al., "An Allosteric Modulator of the Adenosine A1 Receptor Improves Cardiac Function Following Ischaemia in Murine Isolated Hearts", Pharmaceuticals, 2013, vol. 6(4), pp. 546-556.
Butcher A., et al., "Effect of a Novel Partial Adenosine A1 Receptor Agonist VCP102 in Reducing Ischemic Damage in the Mouse Heart", Drug Development Research, 2007, vol. 68, pp. 529-537.
Devine S.M., et al., "Synthesis and Evaluation of New N6-Substituted Adenosine-5'-N-Methylcarboxamides as A3 Adenosine Receptor Agonists", Bioorganic & Medicinal Chemistry, 2010, vol. 18(9), pp. 3078-3087.
Go M., et al., "Synthesis of Some Novel Amodiaquine Analogues as Potential Antimalarial and Antifilarial Compounds", Journal of Medicinal Chemistry, 1981, vol. 24, pp. 1471-1475.
Gregg A., et al., "Dual Acting Antioxidant A1 Adenosine Receptor Agonists",Bioorganic & Medicinal Chemistry Letters, 2007, vol. 17(19), pp. 5437-5441.

(Continued)

*Primary Examiner* — Erich A Leeser
(74) *Attorney, Agent, or Firm* — Allisyn Monteleone

(57) ABSTRACT

The present disclosure provides for compounds of the general Formula (I)

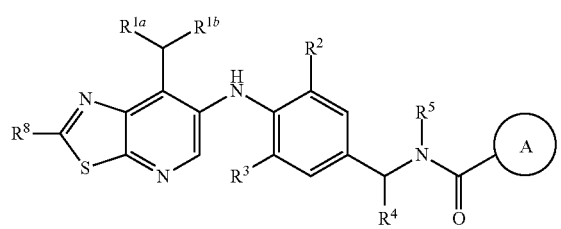

(I)

wherein $R^{1a}$, $R^{1b}$, $R^2$, $R^3$, $R^4$, $R^5$, $R^6$, $R^7$, $R^8$, and Ring A have any of the values defined in the specification, and pharmaceutically acceptable salts thereof.

2 Claims, No Drawings

(56) References Cited

U.S. PATENT DOCUMENTS

| | | |
|---|---|---|
| 11,091,460 B2 | 8/2021 | Liu et al. |
| 11,135,207 B2 | 10/2021 | Romero et al. |
| 11,166,959 B2 | 11/2021 | Araujo et al. |
| 11,186,593 B2 | 11/2021 | Ho et al. |
| 11,279,688 B2 | 3/2022 | Brubaker et al. |
| 2003/0092709 A1 | 5/2003 | Yoon et al. |
| 2004/0077638 A1 | 4/2004 | Geneste et al. |
| 2008/0153799 A1 | 6/2008 | Laurent et al. |
| 2010/0048536 A1 | 2/2010 | Geneste et al. |
| 2010/0121052 A1 | 5/2010 | Jain et al. |
| 2010/0216767 A1 | 8/2010 | Aikawa et al. |
| 2010/0256188 A1 | 10/2010 | Pfau et al. |
| 2010/0267697 A1 | 10/2010 | Galullo et al. |
| 2011/0313156 A1 | 12/2011 | Engelhardt et al. |
| 2012/0196897 A1 | 8/2012 | Pfau et al. |
| 2015/0344444 A1 | 12/2015 | Schmees et al. |
| 2018/0273573 A1 | 9/2018 | Tan et al. |
| 2019/0038603 A1 | 2/2019 | Jakobsson |
| 2020/0270211 A1 | 8/2020 | Burnett et al. |
| 2021/0113534 A1 | 4/2021 | Richards et al. |
| 2021/0196723 A1 | 7/2021 | Rickard et al. |
| 2021/0355088 A1 | 11/2021 | Schönbrunn et al. |
| 2022/0079926 A1 | 3/2022 | Romero et al. |
| 2022/0119413 A1 | 4/2022 | Ho et al. |

FOREIGN PATENT DOCUMENTS

| | | |
|---|---|---|
| JP | 2006241089 A | 9/2006 |
| JP | 5219583 B2 | 6/2013 |
| JP | 5219594 B2 | 6/2013 |
| JP | 5443720 B2 | 3/2014 |
| WO | WO-03044014 A1 | 5/2003 |
| WO | WO-2007058482 A1 | 5/2007 |
| WO | WO-2008003958 A2 | 1/2008 |
| WO | WO-2008079988 A2 | 7/2008 |
| WO | WO-2009153313 A1 | 12/2009 |
| WO | WO-2010093419 A1 | 8/2010 |
| WO | WO-2010100249 A1 | 9/2010 |
| WO | WO-2010147898 A2 | 12/2010 |
| WO | WO-2012022792 A1 | 2/2012 |
| WO | WO-2012022793 A1 | 2/2012 |
| WO | WO-2012068546 A1 | 5/2012 |
| WO | WO-2012075232 A1 | 6/2012 |
| WO | WO-2012076673 A1 | 6/2012 |
| WO | WO-2013038308 A1 | 3/2013 |
| WO | WO-2013157540 A1 | 10/2013 |
| WO | WO-2014146246 A1 | 9/2014 |
| WO | WO-2014146490 A1 | 9/2014 |
| WO | WO-2016027904 A1 | 2/2016 |
| WO | WO-2017144909 A1 | 8/2017 |
| WO | WO-2018020474 A1 | 2/2018 |
| WO | WO-2018226150 A1 | 12/2018 |
| WO | WO-2018228369 A1 | 12/2018 |
| WO | WO-2020031107 A1 | 2/2020 |
| WO | WO-2020126954 A1 | 6/2020 |
| WO | WO-2021071821 A1 | 4/2021 |
| WO | WO-2021074251 A1 | 4/2021 |
| WO | WO-2021175200 A1 | 9/2021 |
| WO | WO-2022047260 A1 | 3/2022 |
| WO | WO-2022066774 A1 | 3/2022 |
| WO | WO-2022081967 A1 | 4/2022 |
| WO | WO-2022081995 A1 | 4/2022 |
| WO | WO-2022094244 A1 | 5/2022 |
| WO | WO-2022106857 A1 | 5/2022 |
| WO | WO-2023192913 A1 | 10/2023 |

OTHER PUBLICATIONS

Hu C., et al., "Integrating Docking Scores and Key Interaction Profiles to Improve the Accuracy of Molecular Docking: Towards Novel B-Raf V600E Inhibitors", MedChemComm, 2017, vol. 8(9), pp. 1-11.

International Search Report and Written Opinion for Application No. PCT/US2023/065111, mailed on Jun. 23, 2023, 28 pages.

Hamp I., et al., "A Patent Review of MALT1 Inhibitors (2013-Present)," Expert Opinion on Therapeutic Patents, 2021, vol. 31(12), pp. 1-18.

Ngiam M.L., et al., "Hydrophobicity and Antifilarial Activities of 4-Aminoquinolines", The Southeast Asian Journal of Tropical Medicine and Public Health, 1982, vol. 13(4), pp. 658-661.

NVS-MALTI: "Allosteric inhibitor",URL: https://www.thesgc.org/node/1330339.

NVS-MALTI: "Overview for NVS-MALT1 an allosteric inhibitor of MALT1", Interface between caspase and Ig3 domains, URL: https://www.sgc-ffm.uni-frankfurt.de/chemProbes#!specificprobeoverview/NVS-MALT1.

Oliveira T.M., et al., "The Structure of Human GCN2 Reveals a Parallel, Back-to-Back Kinase Dimer with a Plastic DFG Activation Loop Motif", The Biochemical Journal, 2020, vol. 477(1), pp. 275-284.

Vasbinder M.M., et al., "Discovery and Optimization of a Novel Series of Potent Mutant B-Raf(V600E) Selective Kinase Inhibitors", Journal of Medicinal Chemistry, 2013, vol. 56(5), pp. 1996-2015.

THIAZOLO[5,4-B]PYRIDINE MALT-1 INHIBITORS

CROSS REFERENCE TO RELATED APPLICATIONS

This application is a non-provisional application which claims the benefit of, and priority to, U.S. Provisional Application No. 63/362,302, filed on Mar. 31, 2022, the content of which is hereby incorporated by reference in its entirety.

FIELD

The present disclosure relates to compounds that inhibit the activity of Mucosa Associated Lymphoid tissue lymphoma translocation protein 1 (MALT-1) and compositions containing the compounds.

BACKGROUND

The B and T cells of the adaptive immune system utilize the pleiotropic NF-κB signaling pathway to transduce extracellular signals from cognate antigen receptors to increase survival and proliferation. This signal transduction leads to a rapid nuclear localization of NF-κB and activation of target genes including proinflammatory cytokines and negative regulators of apoptosis. A key downstream signaling hub of the NF-κB pathway is the CARD11-BCL10-MALT1 (CBM) complex, which plays an essential regulatory role. Upon B cell receptor and T cell receptor stimulation, the CBM complex is formed and recruits multiple signaling proteins, setting canonical NF-κB activation in motion.

The paracaspase MALT1 is an essential modulator within the CBM complex. MALT1 not only acts as a scaffold that assembles protein complexes for NF-κB activation, but it also acts as a protease that cleaves negative regulators of the NF-κB pathway for signal reinforcement.

Aberrant activation of NF-κB signaling occurs in activated B cell-like subtype diffuse large B cell lymphoma (ABC-DLBCL). ABC-DLBCL tumors have a gene expression signature characteristic of B cells activated through their B cell receptor. In the case of DLBCL, gain-of-function alternations in the BCR pathway are frequently detected, and these mutations trigger constitutive NF-κB activation, which is required for tumor cell survival.

Given MALT-1's role as a modulator of the NF-κB pathway, which plays a central role in diseases including ABC-DLBCL, there is a need for compounds that inhibit MALT-1 protease activity for their use as anti-ABC-DLBCL therapies. In particular, there is a need for MALT-1 compounds that inhibit MALT-1 protease activity that have improved pharmaceutical properties.

BRIEF SUMMARY

In one aspect, the present disclosure provides for compounds of Formula (I), or a pharmaceutically acceptable salt thereof,

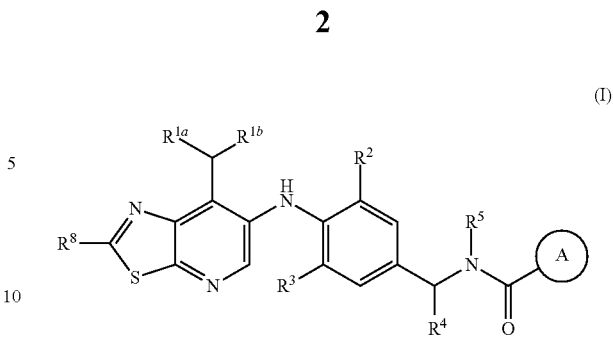

wherein:

$R^{1a}$ is selected from the group consisting of $OCH_3$ and $CH_3$;

$R^{1b}$ is selected from the group consisting of $CH_3$, $CHF_2$, and $CF_3$;

$R^2$ is selected from the group consisting of H and F;

$R^3$ is selected from the group consisting of H and F;

$R^4$ is selected from the group consisting of $CHF_2$ and $CF_3$;

$R^5$ is $C_1$-$C_4$ alkyl;

Ring A is a ring selected from the group consisting of

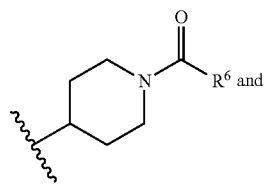

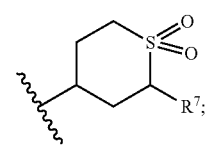

$R^6$ is selected from the group consisting of $C_1$-$C_4$ alkyl and $C_1$-$C_4$ hydroxyalkyl;

$R^7$ is selected from the group consisting of H and $C_1$-$C_4$ alkyl; and $R^7$ is selected from the group consisting of $CHF_2$ and $CH_3$.

$R^8$ is selected from the group consisting of $CHF_2$ and $CH_3$.

In another aspect, Ring A is

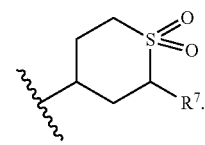

In another aspect, $R^2$ is H. In another aspect, $R^3$ is H. In another aspect, $R^{1a}$ is $OCH_3$. In another aspect, $R^{1b}$ is $CHF_2$. In another aspect, $R^5$ is methyl.

In another aspect, Ring A is

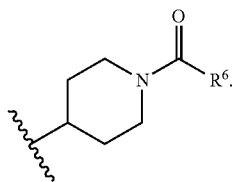

In another aspect, $R^{1a}$ is $OCH_3$. In another aspect, $R^{1b}$ is $CHF_2$. In another aspect, $R^6$ is $C_1$-$C_4$ alkyl. In another aspect, $R^5$ is $C_1$-$C_4$ alkyl.

In another aspect, the compound is selected from the group consisting of:

N-methyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1$\lambda^6$-thiane-4-carboxamide;

N-methyl-1,1-dioxo-N-{(1S)-2,2,2-trifluoro-1-[4-({2-methyl-7-[(1R)-2,2,2-trifluoro-1-methoxyethyl][1,3]thiazolo[5,4-b]pyridin-6-yl}amino)phenyl]ethyl}-1$\lambda^6$-thiane-4-carboxamide;

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1$\lambda^6$-thiane-4-carboxamide;

N-{(1S)-2,2-difluoro-1-[4-({7-[(1S)-1-methoxyethyl]-2-methyl[1,3]thiazolo[5,4-b]pyridin-6-yl}amino)phenyl]ethyl}-N-methyl-1,1-dioxo-1$\lambda^6$-thiane-4-carboxamide;

N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1$\lambda^6$-thiane-4-carboxamide;

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-N-methyl-1,1-dioxo-1$\lambda^6$-thiane-4-carboxamide;

N-ethyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1$\lambda^6$-thiane-4-carboxamide;

N-methyl-1,1-dioxo-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}-1$\lambda^6$-thiane-4-carboxamide;

N-{(1S)-1-[3,5-difluoro-4-({7-[(1S)-1-methoxyethyl]-2-methyl[1,3]thiazolo[5,4-b]pyridin-6-yl}amino)phenyl]-2,2,2-trifluoroethyl}-N-methyl-1,1-dioxo-1$\lambda^6$-thiane-4-carboxamide;

N-methyl-1,1-dioxo-N-{(1S)-2,2,2-trifluoro-1-[3-fluoro-4-({7-[(1S)-1-methoxyethyl]-2-methyl[1,3]thiazolo[5,4-b]pyridin-6-yl}amino)phenyl]ethyl}-1$\lambda^6$-thiane-4-carboxamide;

N-methyl-1,1-dioxo-N-{(1S)-2,2,2-trifluoro-1-[4-({2-methyl-7-[(1S)-2,2,2-trifluoro-1-methoxyethyl][1,3]thiazolo[5,4-b]pyridin-6-yl}amino)phenyl]ethyl}-1$\lambda^6$-thiane-4-carboxamide;

N-{(1S)-2,2-difluoro-1-[4-({7-[(1R)-1-methoxyethyl]-2-methyl[1,3]thiazolo[5,4-b]pyridin-6-yl}amino)phenyl]ethyl}-N-methyl-1,1-dioxo-1$\lambda^6$-thiane-4-carboxamide;

N-{(1S)-1-[4-({7-[(1S)-2,2-difluoro-1-methoxyethyl]-2-methyl[1,3]thiazolo[5,4-b]pyridin-6-yl}amino)phenyl]-2,2-difluoroethyl}-N-methyl-1,1-dioxo-1$\lambda^6$-thiane-4-carboxamide;

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-N-methyl-1,1-dioxo-1$\lambda^6$-thiane-4-carboxamide;

N-{(1S)-1-[4-({2-(difluoromethyl)-7-[(1S)-1-methoxyethyl][1,3]thiazolo[5,4-b]pyridin-6-yl}amino)phenyl]-2,2,2-trifluoroethyl}-N-methyl-1,1-dioxo-1$\lambda^6$-thiane-4-carboxamide;

N-[(1S)-1-(4-{[7-(1,1-difluoropropan-2-yl)-2-methyl[1,3]thiazolo[5,4-b]pyridin-6-yl]amino}phenyl)-2,2,2-trifluoroethyl]-N-methyl-1,1-dioxo-1$\lambda^6$-thiane-4-carboxamide;

N-{(1S)-1-[4-({7-[(1R)-2,2-difluoro-1-methoxyethyl]-2-methyl[1,3]thiazolo[5,4-b]pyridin-6-yl}amino)-3-fluorophenyl]-2,2,2-trifluoroethyl}-N-methyl-1,1-dioxo-1$\lambda^6$-thiane-4-carboxamide;

1-acetyl-N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methylpiperidine-4-carboxamide;

1-acetyl-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

1-(hydroxyacetyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide;

1-(3-hydroxypropanoyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

1-(2-hydroxy-2-methylpropanoyl)-N-methyl-N-{(1S)-2,2,2-trifluoro-1-({7-[(1S)-1-methoxyethyl]-2-methyl[1,3]thiazolo[5,4-b]pyridin-6-yl}amino)phenyl]ethyl}piperidine-4-carboxamide;

1-(2,3-dihydroxypropanoyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

1-[(2R)-2-hydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

1-[(2S)-2-hydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

1-[(2R)-2,3-dihydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

N-{(1S)-2,2-difluoro-1-[4-({7-[(1S)-1-methoxyethyl]-2-methyl[1,3]thiazolo[5,4-b]pyridin-6-yl}amino)phenyl]ethyl}-1-(hydroxyacetyl)-N-methylpiperidine-4-carboxamide;

1-acetyl-N-{(1S)-2,2-difluoro-1-[4-({7-[(1S)-1-methoxyethyl]-2-methyl[1,3]thiazolo[5,4-b]pyridin-6-yl}amino)phenyl]ethyl}-N-methylpiperidine-4-carboxamide;

1-[(2S)-2,3-dihydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide;

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-1-(hydroxyacetyl)-N-methylpiperidine-4-carboxamide;

N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide;

1-acetyl-N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-N-methylpiperidine-4-carboxamide;

1-(hydroxyacetyl)-N-methyl-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}piperidine-4-carboxamide;

1-acetyl-N-methyl-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}piperidine-4-carboxamide;

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-1-(hydroxyacetyl)-N-methylpiperidine-4-carboxamide;

1-acetyl-N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-N-methylpiperidine-4-carboxamide;

N-methyl-1,1-dioxo-N-{(1S)-2,2,2-trifluoro-1-[4-({2-methyl-7-[(2R)-1,1,1-trifluoropropan-2-yl][1,3]thiazolo[5,4-b]pyridin-6-yl}amino)phenyl]ethyl}-1$\lambda^6$-thiane-4-carboxamide; and N-methyl-1,1-dioxo-N-{(1S)-2,2,2-trifluoro-1-[4-({2-methyl-7-[(2S)-1,1,1-trifluoropropan-2-yl][1,3]thiazolo[5,4-b]pyridin-6-yl}amino)phenyl]ethyl}-1$\lambda^6$-thiane-4-carboxamide; or a pharmaceutically acceptable salt thereof.

In another aspect, the compound is N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1$\lambda^6$-thiane-4-carboxamide, or a pharmaceutically acceptable salt thereof.

In another aspect, the compound is N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1$\lambda^6$-thiane-4-carboxamide.

In another aspect, the present disclosure provides for a pharmaceutical composition comprising a therapeutically effective amount of a compound of Formula (I) according to any of the preceding aspects, or a pharmaceutically acceptable salt thereof, in combination with a pharmaceutically acceptable carrier.

In another aspect, the present disclosure provides for a method for treating activated B cell-like subtype diffuse large B cell lymphoma (ABC-DLBCL) in a subject comprising administering a therapeutically effective amount of a compound of Formula (I) according to any of the preceding aspects or a pharmaceutically acceptable salt thereof, to a subject in need thereof.

In another aspect, the present disclosure provides for a method of synthesizing a compound of Formula (3A) according to claim 1, by reacting a compound of Formula (1G)

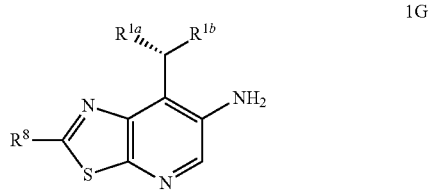

with a compound of Formula (2G)

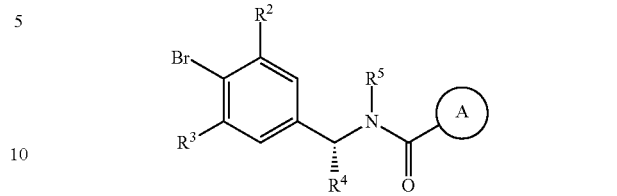

in a solvent, in the presence of a base and a catalyst, to form a compound of Formula (3A)

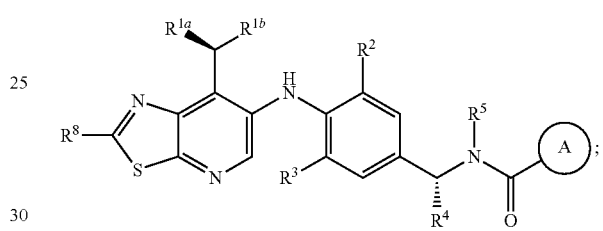

wherein:

$R^{1a}$ is selected from the group consisting of $OCH_3$ and $CH_3$;

$R^{1b}$ is selected from the group consisting of $CH_3$, $CHF_2$, and $CF_3$;

$R^2$ is selected from the group consisting of H and F;

$R^3$ is selected from the group consisting of H and F;

$R^4$ is selected from the group consisting of $CHF_2$ and $CF_3$;

$R^5$ is $C_1$-$C_4$ alkyl;

Ring A is a ring selected from the group consisting of

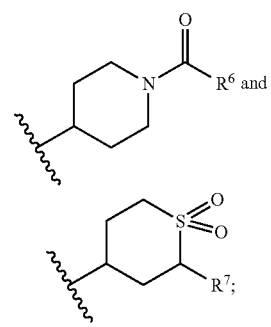

$R^6$ is selected from the group consisting of $C_1$-$C_4$ alkyl and $C_1$-$C_4$ hydroxyalkyl;

$R^7$ is selected from the group consisting of H and $C_1$-$C_4$ alkyl; and $R^8$ is selected from the group consisting of $CHF_2$ and $CH_3$.

DETAILED DESCRIPTION

The present disclosure describes compounds that inhibit the activity of MALT-1.

Disclosed herein are compounds of Formula (I)

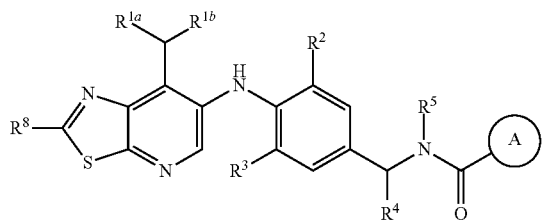

wherein:

$R^{1a}$ is selected from the group consisting of $OCH_3$ and $CH_3$;

$R^{1b}$ is selected from the group consisting of $CH_3$, $CHF_2$, and $CF_3$;

$R^2$ is selected from the group consisting of H and F;

$R^3$ is selected from the group consisting of H and F;

$R^4$ is selected from the group consisting of $CHF_2$ and $CF_3$;

$R^5$ is $C_1$-$C_4$ alkyl;

Ring A is a ring selected from the group consisting of

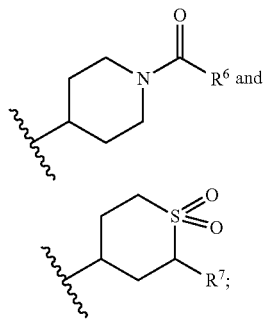

$R^6$ is selected from the group consisting of $C_1$-$C_4$ alkyl and $C_1$-$C_4$ hydroxyalkyl;

$R^7$ is selected from the group consisting of H and $C_1$-$C_4$ alkyl; and $R^8$ is selected from the group consisting of $CHF_2$ and $CH_3$.

Definitions

Certain terms as used in the specification are intended to refer to the following definitions, as detailed below.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds.

As used in the specification and the appended claims, unless specified to the contrary, the following terms have the meaning indicated:

The term "alkyl," as used herein, refers to a saturated, straight or branched hydrocarbon chain radical. Representative examples of alkyl include, but are not limited to, methyl, ethyl, n-propyl, isopropyl, n-butyl, sec-butyl, isobutyl, tert-butyl, and the like.

The term "hydroxyalkyl," as used herein, refers to one or more hydroxy groups (OH) appended to the parent molecular moiety through an alkyl group, as defined herein. The hydroxyalkyl group may have one, two, three, or four carbons unless otherwise specified. Representative examples of hydroxyalkyl include, but are not limited to, hydroxymethyl, 2-hydroxyethyl, 3-hydroxypropyl, and the like.

In some instances, the number of carbon atoms in a moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms.

With reference to the use of the words "comprise" or "comprises" or "comprising" in the present disclosure (including the claims), unless the context requires otherwise, those words are used on the basis and clear understanding that they are to be interpreted inclusively, rather than exclusively.

The phrase "pharmaceutical composition" refers to a composition suitable for administration in medical use.

The phrase "a pharmaceutically acceptable carrier" means a single pharmaceutically acceptable carrier as well as one or more pharmaceutically acceptable carriers, and the like.

The phrase "pharmaceutically acceptable salt" refers to salts that are within the scope of sound medical judgement, suitable for use in contact with the tissues of humans and lower animals without undue toxicity, irritation, allergic response and the like and are commensurate with a reasonable benefit/risk ratio.

The term "stable" refers to compounds that possess stability sufficient to allow manufacture and that maintain the integrity of the compound for a sufficient period of time to be useful for the purpose detailed herein.

The term "subject," as used herein, refers to humans. The terms "human," "patient," and "subject" are used interchangeably herein.

The phrase "therapeutically effective amount" refers to an amount of a compound, or a pharmaceutically acceptable salt thereof, sufficient to treat one or more of the symptoms of the condition or disorder being treated when administered for treatment in a particular subject or subject population.

The terms "treat," "treating," and "treatment," as used herein, refer to a method of alleviating or abrogating a disease and/or its attendant symptoms.

Compounds

Compounds of the present disclosure have the general Formula (I) as described herein.

In embodiments, the present disclosure provides for compounds of Formula (I), or a pharmaceutically acceptable salt thereof,

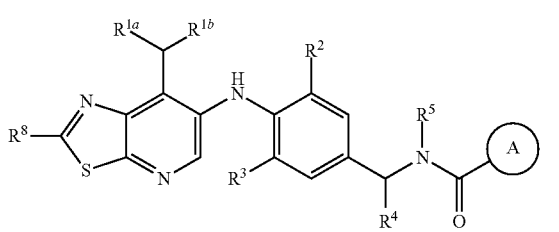

wherein:

$R^{1a}$ is selected from the group consisting of $OCH_3$ and $CH_3$;

$R^{1b}$ is selected from the group consisting of $CH_3$, $CHF_2$, and $CF_3$;

$R^2$ is selected from the group consisting of H and F;

$R^3$ is selected from the group consisting of H and F;

$R^4$ is selected from the group consisting of $CHF_2$ and $CF_3$;

$R^5$ is $C_1$-$C_4$ alkyl;

Ring A is a ring selected from the group consisting of

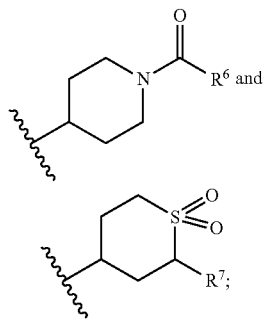

$R^6$ is selected from the group consisting of $C_1$-$C_4$ alkyl and $C_1$-$C_4$ hydroxyalkyl;

$R^7$ is selected from the group consisting of H and $C_1$-$C_4$ alkyl; and $R^8$ is selected from the group consisting of $CHF_2$ and $CH_3$.

Particular values of variable groups in compounds of Formula (I) are as follows. Such values may be used where appropriate with any of the other values, definitions, claims or embodiments defined herein.

In certain embodiments of Formula (I), or a pharmaceutically acceptable salt thereof, $R^{1a}$ is selected from the group consisting of $OCH_3$ and $CH_3$. In certain embodiments of Formula (I), or a pharmaceutically acceptable salt thereof, $R^{1a}$ is $OCH_3$. In certain embodiments of Formula (I), or a pharmaceutically acceptable salt thereof, $R^{1a}$ is $CH_3$.

In certain embodiments of Formula (I), or a pharmaceutically acceptable salt thereof, $R^{1b}$ is selected from the group consisting of $CH_3$, $CHF_2$, and $CF_3$. In certain embodiments of Formula (I), or a pharmaceutically acceptable salt thereof, $R^{1b}$ is selected from the group consisting of $CH_3$ and $CHF_2$. In certain embodiments of Formula (I), or a pharmaceutically acceptable salt thereof, $R^{1b}$ is selected from the group consisting of $CH_3$ and $CF_3$. In certain embodiments of Formula (I), or a pharmaceutically acceptable salt thereof, $R^{1b}$ is selected from the group consisting of $CHF_2$ and $CF_3$. In certain embodiments of Formula (I), or a pharmaceutically acceptable salt thereof, $R^{1b}$ is $CH_3$. In certain embodiments of Formula (I), or a pharmaceutically acceptable salt thereof, $R^{1b}$ is $CHF_2$. In certain embodiments of Formula (I), or a pharmaceutically acceptable salt thereof, $R^{1b}$ is $CF_3$.

In certain embodiments of Formula (I), or a pharmaceutically acceptable salt thereof, $R^{1a}$ is $OCH_3$ and $R^{1b}$ is $CHF_2$.

In certain embodiments of Formula (I), or a pharmaceutically acceptable salt thereof, $R^2$ is selected from the group consisting of H and F. In certain embodiments of Formula (I), or a pharmaceutically acceptable salt thereof, $R^2$ is H, or a pharmaceutically acceptable salt thereof. In certain embodiments, of Formula (I), or a pharmaceutically acceptable salt thereof, $R^2$ is F.

In certain embodiments of Formula (I), or a pharmaceutically acceptable salt thereof, $R^{1a}$ is $OCH_3$, $R^{1b}$ is $CHF_2$, and $R^2$ is H.

In certain embodiments of Formula (I), or a pharmaceutically acceptable salt thereof, $R^3$ is selected from the group consisting of H and F. In certain embodiments of Formula (I), or a pharmaceutically acceptable salt thereof, $R^3$ is H. In certain embodiments of Formula (I), or a pharmaceutically acceptable salt thereof, $R^3$ is F.

In certain embodiments of Formula (I), or a pharmaceutically acceptable salt thereof, $R^{1a}$ is $OCH_3$, $R^{1b}$ is $CHF_2$, $R^2$ is H, and $R^3$ is H.

In certain embodiments of Formula (I), or a pharmaceutically acceptable salt thereof, $R^4$ is selected from the group consisting of $CHF_2$ and $CF_3$. In certain embodiments of Formula (I), or a pharmaceutically acceptable salt thereof, $R^4$ is $CHF_2$. In certain embodiments of Formula (I), or a pharmaceutically acceptable salt thereof, $R^4$ is $CF_3$.

In certain embodiments of Formula (I), or a pharmaceutically acceptable salt thereof, $R^{1a}$ is $OCH_3$, $R^{1b}$ is $CHF_2$, $R^2$ is H, $R^3$ is H, and $R^4$ is $CF_3$.

In certain embodiments of Formula (I), or a pharmaceutically acceptable salt thereof, $R^5$ is $C_1$-$C_4$ alkyl. In certain embodiments of Formula (I), or a pharmaceutically acceptable salt thereof, $R^5$ is methyl. In certain embodiments of Formula (I), or a pharmaceutically acceptable salt thereof, $R^5$ is ethyl.

In certain embodiments of Formula (I), or a pharmaceutically acceptable salt thereof, $R^{1a}$ is $OCH_3$, $R^{1b}$ is $CHF_2$, $R^2$ is H, $R^3$ is H, $R^4$ is $CF_3$, and $R^5$ is methyl.

In certain embodiments of Formula (I), or a pharmaceutically acceptable salt thereof, $R^{1a}$ is $OCH_3$, $R^{1b}$ is $CHF_2$, $R^2$ is H, $R^3$ is H, $R^4$ is $CF_3$, and $R^5$ is H.

In certain embodiments of Formula (I), or a pharmaceutically acceptable salt thereof, Ring A is selected from the group consisting of

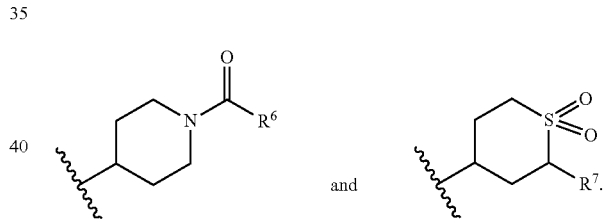

In certain embodiments of Formula (I), or a pharmaceutically acceptable salt thereof, Ring A is

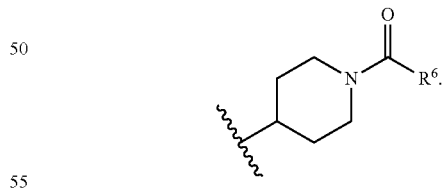

In certain embodiments of Formula (I), or a pharmaceutically acceptable salt thereof, Ring A

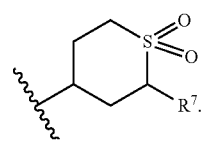

In certain embodiments of Formula (I), or a pharmaceutically acceptable salt thereof, $R^6$ is selected from the group consisting of $C_1$-$C_4$ alkyl and $C_1$-$C_4$ hydroxyalkyl. In certain embodiments of Formula (I), or a pharmaceutically acceptable salt thereof, $R^6$ is $C_1$-$C_4$ alkyl. In certain embodiments of Formula (I), or a pharmaceutically acceptable salt thereof, $R^6$ is $C_1$-$C_4$ hydroxyalkyl.

In certain embodiments of Formula (I), or a pharmaceutically acceptable salt thereof, $R^{1a}$ is $OCH_3$, $R^{1b}$ is $CHF_2$, $R^2$ is H, $R^3$ is H, $R^4$ is $CF_3$, $R^5$ is H, and Ring A is

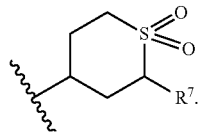

In certain embodiments of Formula (I), or a pharmaceutically acceptable salt thereof, $R^7$ is selected from the group consisting of H and $C_1$-$C_4$ alkyl. In certain embodiments of Formula (I), or a pharmaceutically acceptable salt thereof, $R^7$ is H. In certain embodiments of Formula (I), or a pharmaceutically acceptable salt thereof, $R^7$ is $C_1$-$C_4$ alkyl. In certain embodiments of Formula (I), or a pharmaceutically acceptable salt thereof, $R^7$ is methyl.

In certain embodiments of Formula (I), or a pharmaceutically acceptable salt thereof, $R^{1a}$ is $OCH_3$, $R^{1b}$ is $CHF_2$, $R^2$ is H, $R^3$ is H, $R^4$ is $CF_3$, $R^5$ is H, Ring A is

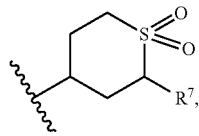

and $R^7$ is H.

In certain embodiments of Formula (I), or a pharmaceutically acceptable salt thereof, $R^8$ is selected from the group consisting of $CHF_2$ and $CH_3$. In certain embodiments of Formula (I), or a pharmaceutically acceptable salt thereof, $R^8$ is $CHF_2$. In certain embodiments of Formula (I), or a pharmaceutically acceptable salt thereof, $R^8$ is $CH_3$.

In certain embodiments of Formula (I), or a pharmaceutically acceptable salt thereof, $R^{1a}$ is $OCH_3$, $R^{1b}$ is $CHF_2$, $R^2$ is H, $R^3$ is H, $R^4$ is $CF_3$, $R^5$ is H, Ring A is

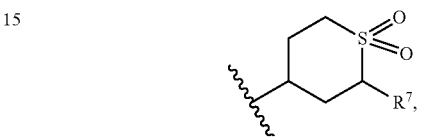

$R^7$ is H, and $R^8$ is $CH_3$.

Compounds disclosed herein may contain one or more variable(s) that occur more than one time in any substituent or in the Formulae herein. Definition of a variable at each occurrence is independent of its definition at another occurrence. Further, combinations of substituents are permissible only if such combinations result in stable compounds.

Compounds of the present disclosure and intermediates were named by using ACD/Name 2021.1.3 (File Version N15E41, Build 123232, 7 Jul. 2021) software program and/or by using Struct=Name naming algorithm as part of CHEMDRAW® Professional v. 15.0.0.106.

Exemplary compounds of Formula (I) include, but are not limited to, the compounds shown in Table 1 below, and pharmaceutically acceptable salts thereof. It is to be understood that when there is a discrepancy between the name of the compound found herein and the structure found in Table 1, the structure in Table 1 shall prevail.

TABLE 1

Exemplary Compounds

| EX | CHEMISTRY |
|---|---|
| 1 | 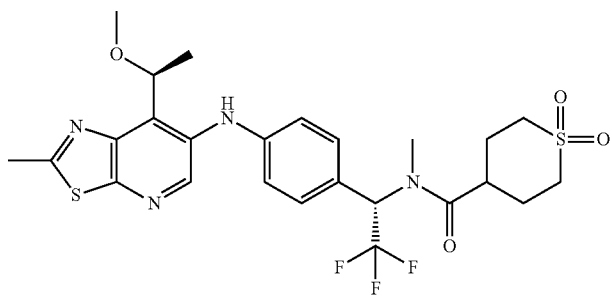 [SMILES: CO[C@@H](C)c1c(Nc2ccc([C@H](N(C)C(=O)C3CCS(=O)(=O)CC3)C(F)(F)F)cc2)cnc2sc(C)nc12] |

TABLE 1-continued
Exemplary Compounds
| EX | CHEMISTRY |
|---|---|
| 2 | 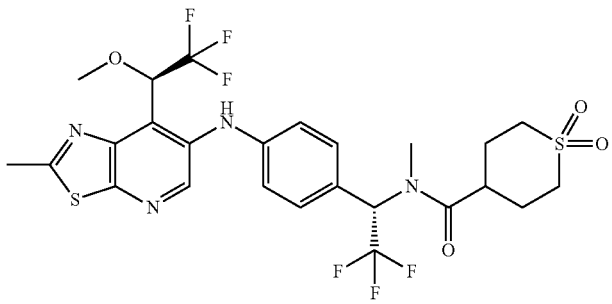 [SMILES: CO[C@H](c1c(Nc2ccc([C@H](N(C)C(=O)C3CCS(=O)(=O)CC3)C(F)(F)F)cc2)cnc2sc(C)nc12)C(F)(F)F] |
| 3 | 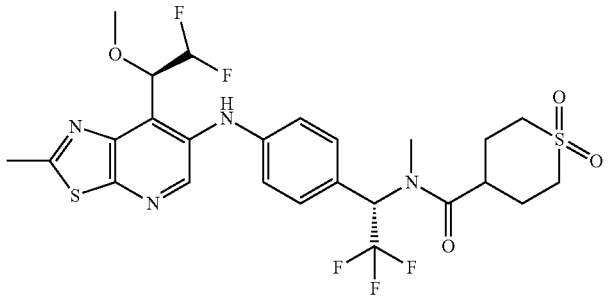 [SMILES: CO[C@H](c1c(Nc2ccc([C@H](N(C)C(=O)C3CCS(=O)(=O)CC3)C(F)(F)F)cc2)cnc2sc(C)nc12)C(F)F] |
| 4 | 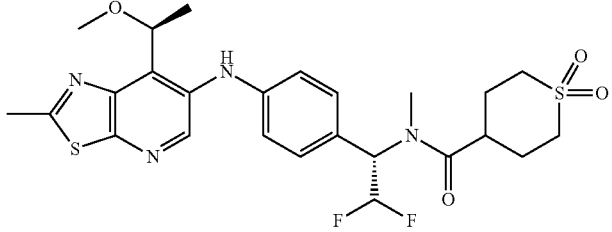 [SMILES: CO[C@@H](C)c1c(Nc2ccc([C@@H](C(F)F)N(C)C(=O)C3CCS(=O)(=O)CC3)cc2)cnc2sc(C)nc12] |
| 5 | 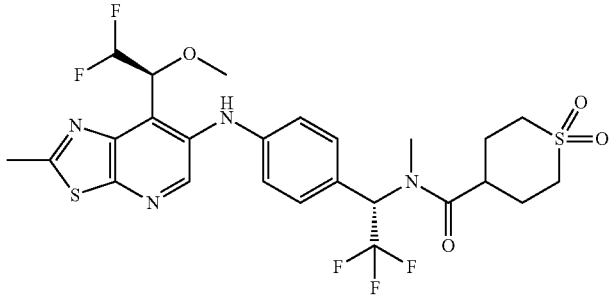 [SMILES: CO[C@@H](c1c(Nc2ccc([C@H](N(C)C(=O)C3CCS(=O)(=O)CC3)C(F)(F)F)cc2)cnc2sc(C)nc12)C(F)F] |
| 6 | 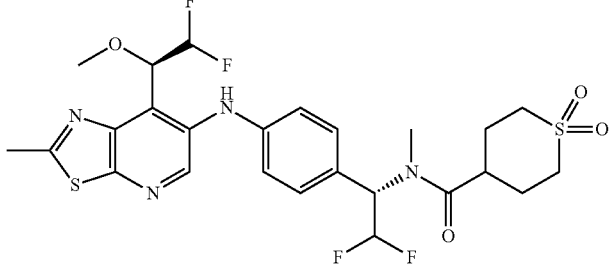 |

TABLE 1-continued
Exemplary Compounds
EX  CHEMISTRY
7  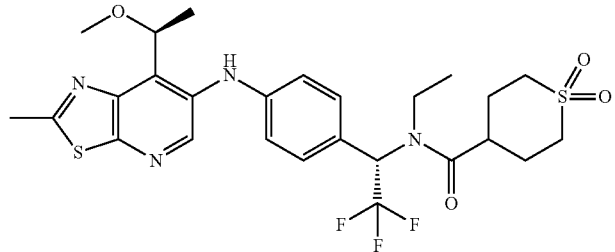 [SMILES: CCN(C(=O)C1CCS(=O)(=O)CC1)[C@@H](c1ccc(Nc2cnc3sc(C)nc3c2[C@H](C)OC)cc1)C(F)(F)F]
8  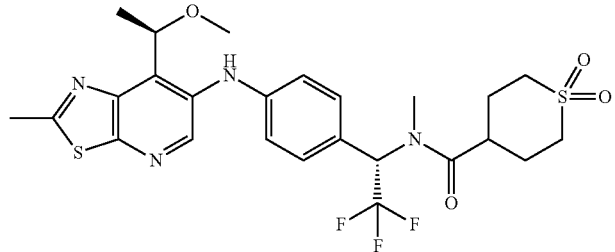 [SMILES: CO[C@H](C)c1c(Nc2ccc([C@H](N(C)C(=O)C3CCS(=O)(=O)CC3)C(F)(F)F)cc2)cnc2sc(C)nc12]
9  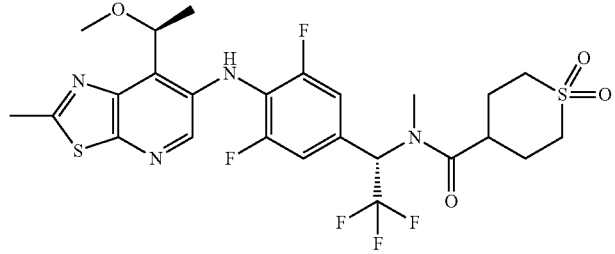 [SMILES: CO[C@@H](C)c1c(Nc2c(F)cc([C@H](N(C)C(=O)C3CCS(=O)(=O)CC3)C(F)(F)F)cc2F)cnc2sc(C)nc12]
10 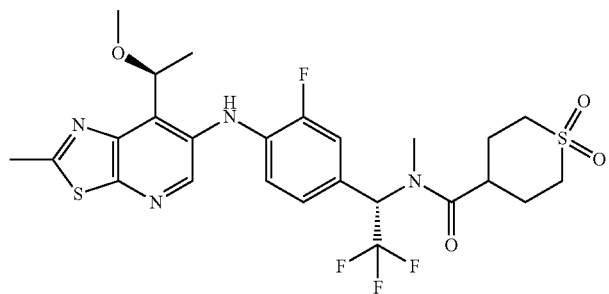 [SMILES: CO[C@@H](C)c1c(Nc2ccc([C@H](N(C)C(=O)C3CCS(=O)(=O)CC3)C(F)(F)F)cc2F)cnc2sc(C)nc12]
11 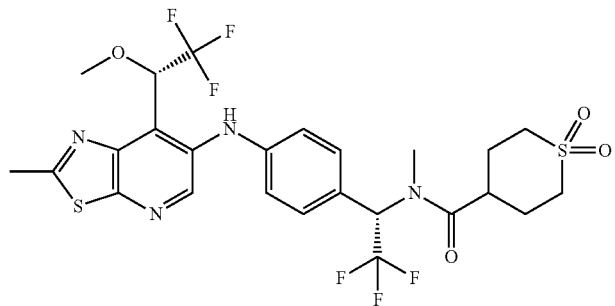 [SMILES: CO[C@@H](c1c(Nc2ccc([C@H](N(C)C(=O)C3CCS(=O)(=O)CC3)C(F)(F)F)cc2)cnc2sc(C)nc12)C(F)(F)F]

TABLE 1-continued
Exemplary Compounds
| EX | CHEMISTRY |
|---|---|
| 12 | 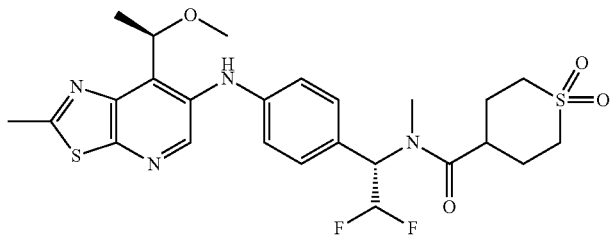 [SMILES: CO[C@H](C)c1c(Nc2ccc([C@@H](C(F)F)N(C)C(=O)C3CCS(=O)(=O)CC3)cc2)cnc2sc(C)nc12] |
| 13 | 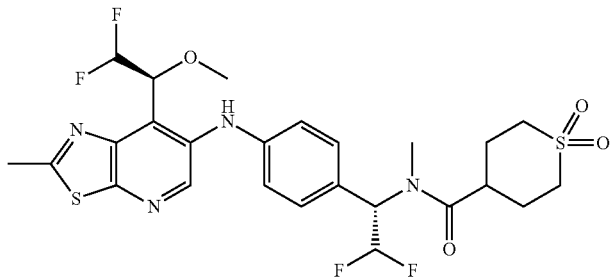 [SMILES: CO[C@@H](c1c(Nc2ccc([C@@H](C(F)F)N(C)C(=O)C3CCS(=O)(=O)CC3)cc2)cnc2sc(C)nc12)C(F)F] |
| 14 | 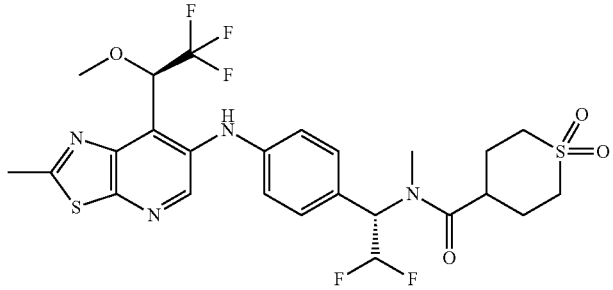 [SMILES: CO[C@H](c1c(Nc2ccc([C@@H](C(F)F)N(C)C(=O)C3CCS(=O)(=O)CC3)cc2)cnc2sc(C)nc12)C(F)(F)F] |
| 15 | 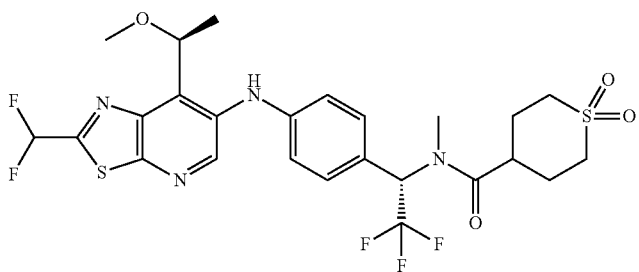 [SMILES: CO[C@@H](C)c1c(Nc2ccc([C@H](N(C)C(=O)C3CCS(=O)(=O)CC3)C(F)(F)F)cc2)cnc2sc(C(F)F)nc12] |
| 16 | 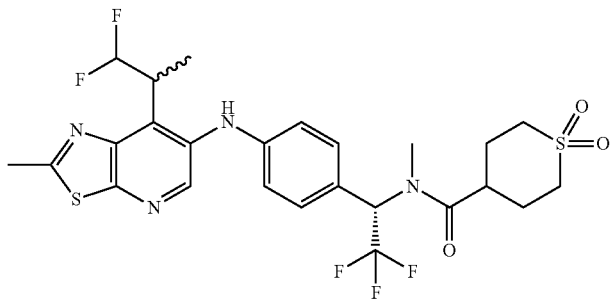 [SMILES: Cc1nc2c(C(C)C(F)F)c(Nc3ccc([C@H](N(C)C(=O)C4CCS(=O)(=O)CC4)C(F)(F)F)cc3)cnc2s1] |

TABLE 1-continued
Exemplary Compounds
| EX | CHEMISTRY |
|---|---|
| 17 | 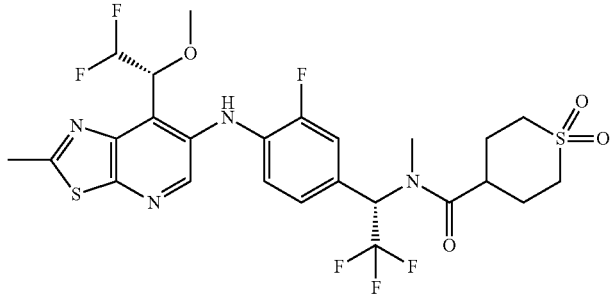 [SMILES: CO[C@H](c1c(Nc2ccc([C@H](N(C)C(=O)C3CCS(=O)(=O)CC3)C(F)(F)F)cc2F)cnc2sc(C)nc12)C(F)F] |
| 18 | 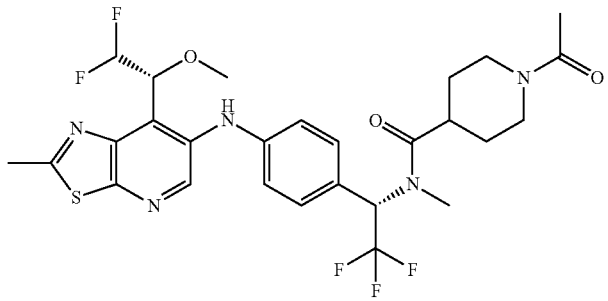 [SMILES: CO[C@H](c1c(Nc2ccc([C@H](N(C)C(=O)C3CCN(C(C)=O)CC3)C(F)(F)F)cc2)cnc2sc(C)nc12)C(F)F] |
| 19 | 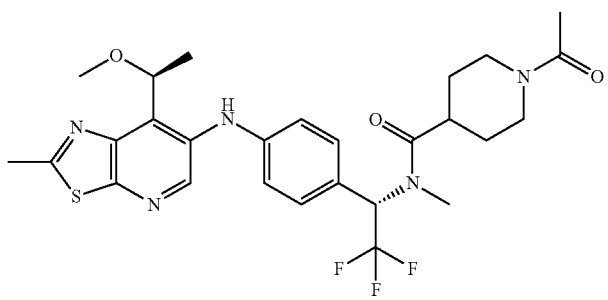 [SMILES: CO[C@@H](C)c1c(Nc2ccc([C@H](N(C)C(=O)C3CCN(C(C)=O)CC3)C(F)(F)F)cc2)cnc2sc(C)nc12] |
| 20 | 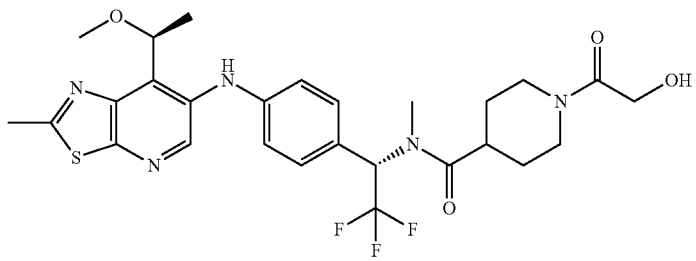 [SMILES: CO[C@@H](C)c1c(Nc2ccc([C@H](N(C)C(=O)C3CCN(C(=O)CO)CC3)C(F)(F)F)cc2)cnc2sc(C)nc12] |
| 21 | 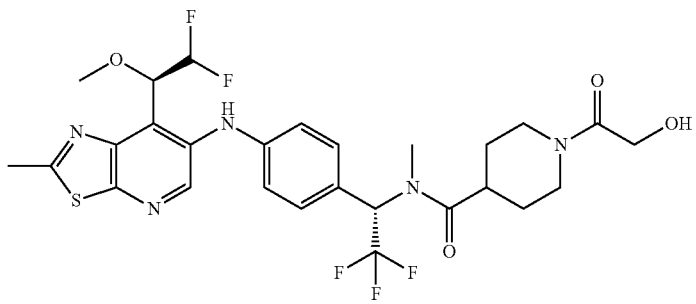 [SMILES: CO[C@H](c1c(Nc2ccc([C@H](N(C)C(=O)C3CCN(C(=O)CO)CC3)C(F)(F)F)cc2)cnc2sc(C)nc12)C(F)F] |

TABLE 1-continued

Exemplary Compounds

| EX | CHEMISTRY |
|---|---|
| 22 | |
| 23 | |
| 24 | |
| 25 | |
| 26 | |

TABLE 1-continued
Exemplary Compounds
EX  CHEMISTRY
27
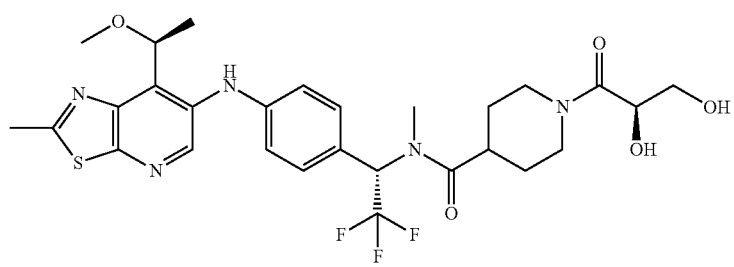 [SMILES: CO[C@@H](C)c1c(Nc2ccc([C@H](N(C)C(=O)C3CCN(C(=O)[C@H](O)CO)CC3)C(F)(F)F)cc2)cnc2sc(C)nc12]
28
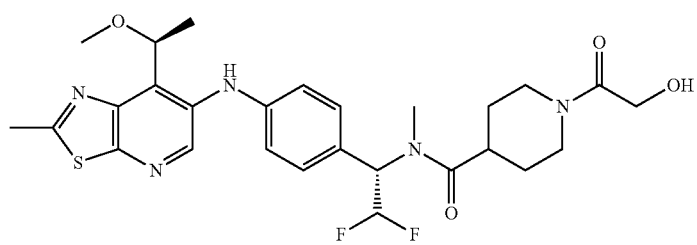 [SMILES: CO[C@@H](C)c1c(Nc2ccc([C@@H](C(F)F)N(C)C(=O)C3CCN(C(=O)CO)CC3)cc2)cnc2sc(C)nc12]
29
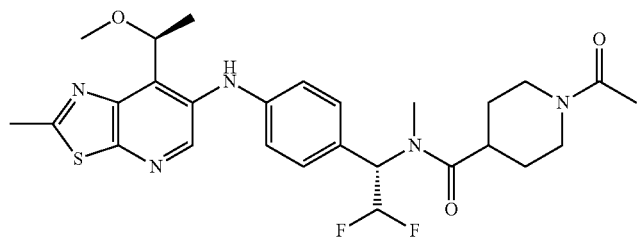 [SMILES: CO[C@@H](C)c1c(Nc2ccc([C@@H](C(F)F)N(C)C(=O)C3CCN(C(C)=O)CC3)cc2)cnc2sc(C)nc12]
30
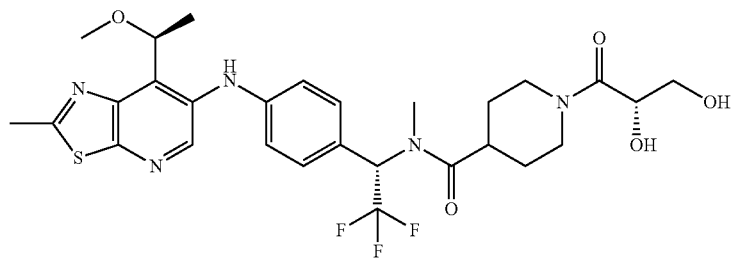 [SMILES: CO[C@@H](C)c1c(Nc2ccc([C@H](N(C)C(=O)C3CCN(C(=O)[C@@H](O)CO)CC3)C(F)(F)F)cc2)cnc2sc(C)nc12]
31
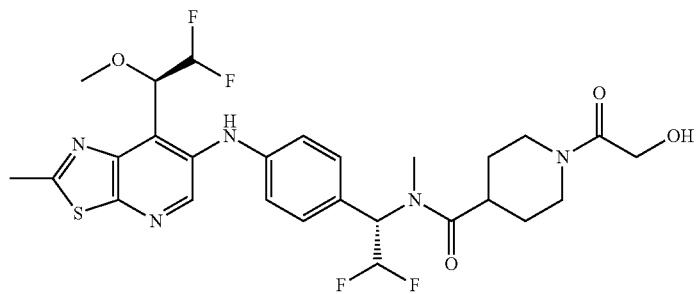 [SMILES: CO[C@H](c1c(Nc2ccc([C@@H](C(F)F)N(C)C(=O)C3CCN(C(=O)CO)CC3)cc2)cnc2sc(C)nc12)C(F)F]

TABLE 1-continued
Exemplary Compounds
| EX | CHEMISTRY |
|----|-----------|
| 32 | 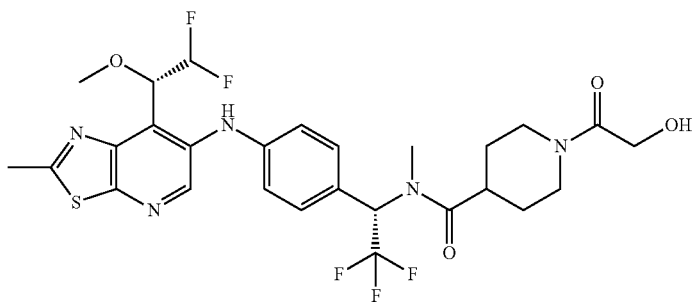 [SMILES: CO[C@@H](c1c(Nc2ccc([C@H](N(C)C(=O)C3CCN(C(=O)CO)CC3)C(F)(F)F)cc2)cnc2sc(C)nc12)C(F)F] |
| 33 | 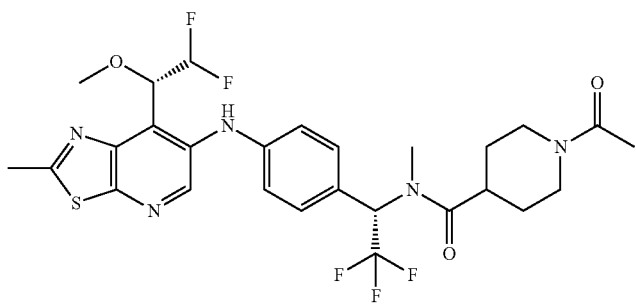 [SMILES: CO[C@@H](c1c(Nc2ccc([C@H](N(C)C(=O)C3CCN(C(C)=O)CC3)C(F)(F)F)cc2)cnc2sc(C)nc12)C(F)F] |
| 34 | 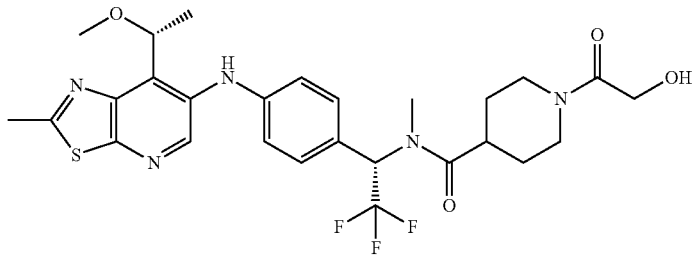 [SMILES: CO[C@H](C)c1c(Nc2ccc([C@H](N(C)C(=O)C3CCN(C(=O)CO)CC3)C(F)(F)F)cc2)cnc2sc(C)nc12] |
| 35 | 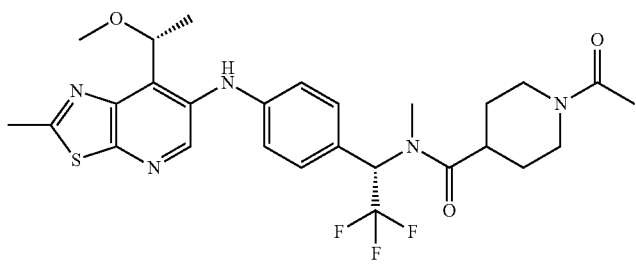 [SMILES: CO[C@H](C)c1c(Nc2ccc([C@H](N(C)C(=O)C3CCN(C(C)=O)CC3)C(F)(F)F)cc2)cnc2sc(C)nc12] |
| 36 | 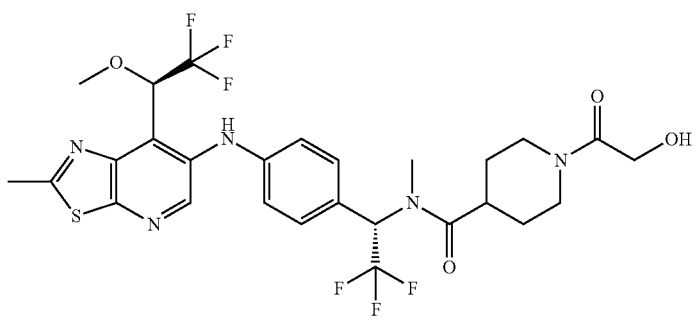 [SMILES: CO[C@H](c1c(Nc2ccc([C@H](N(C)C(=O)C3CCN(C(=O)CO)CC3)C(F)(F)F)cc2)cnc2sc(C)nc12)C(F)(F)F] |

TABLE 1-continued

Exemplary Compounds

| EX | CHEMISTRY |
|---|---|
| 37 | 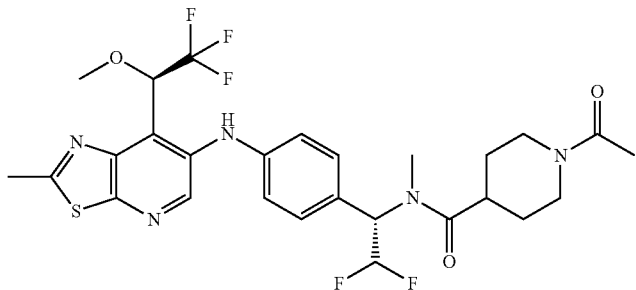 [SMILES: CO[C@H](c1c(Nc2ccc([C@@H](C(F)F)N(C)C(=O)C3CCN(C(C)=O)CC3)cc2)cnc2sc(C)nc12)C(F)(F)F] |
| 38 | 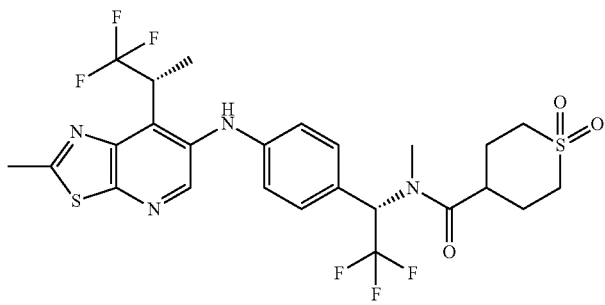 [SMILES: Cc1nc2c([C@@H](C)C(F)(F)F)c(Nc3ccc([C@H](N(C)C(=O)C4CCS(=O)(=O)CC4)C(F)(F)F)cc3)cnc2s1] |
| 39 | 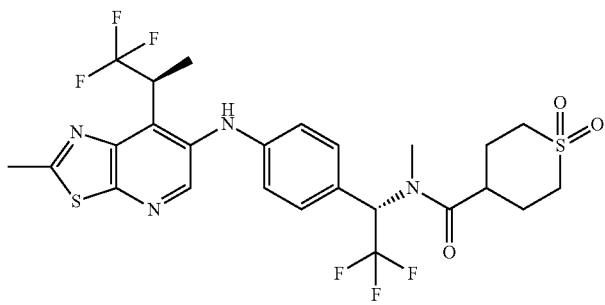 [SMILES: Cc1nc2c([C@H](C)C(F)(F)F)c(Nc3ccc([C@H](N(C)C(=O)C4CCS(=O)(=O)CC4)C(F)(F)F)cc3)cnc2s1] |

Compounds of Formula (I) may be used in the form of pharmaceutically acceptable salts.

Compounds of Formula (I) may contain either a basic or an acidic functionality, or both, and may be converted to a pharmaceutically acceptable salt, when desired, by using a suitable acid or base.

Methods of Making Exemplary Compounds

The compounds of the present disclosure can be better understood in connection with the following synthetic schemes and methods that illustrate a means by which the compounds can be prepared. The compounds of the present disclosure can be prepared by a variety of synthetic procedures. Representative synthetic procedures are shown in, but not limited to, Schemes 1-8. The variables $R^{1a}$, $R^{1b}$, $R^2$, $R^3$, $R^4$, $R^5$, $R^6$, and A are defined as detailed herein.

Abbreviations used in the schemes and description thereof have the following meaning: BOC for tert-butyloxycarbonyl protecting group.

Representative schemes for the synthesis of exemplary intermediates and compounds of Formula (I):

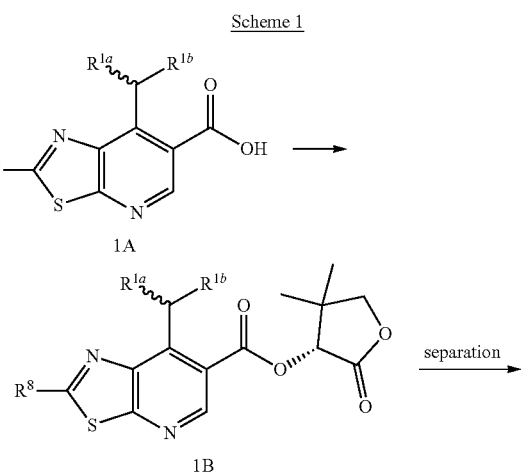

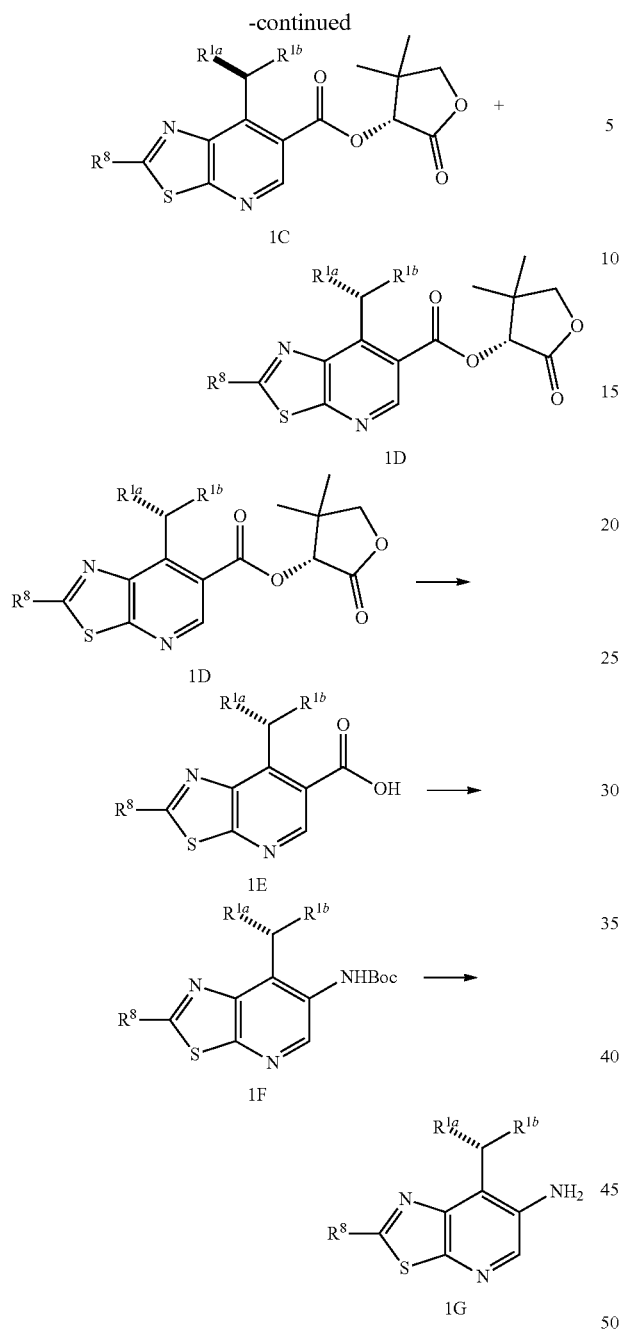

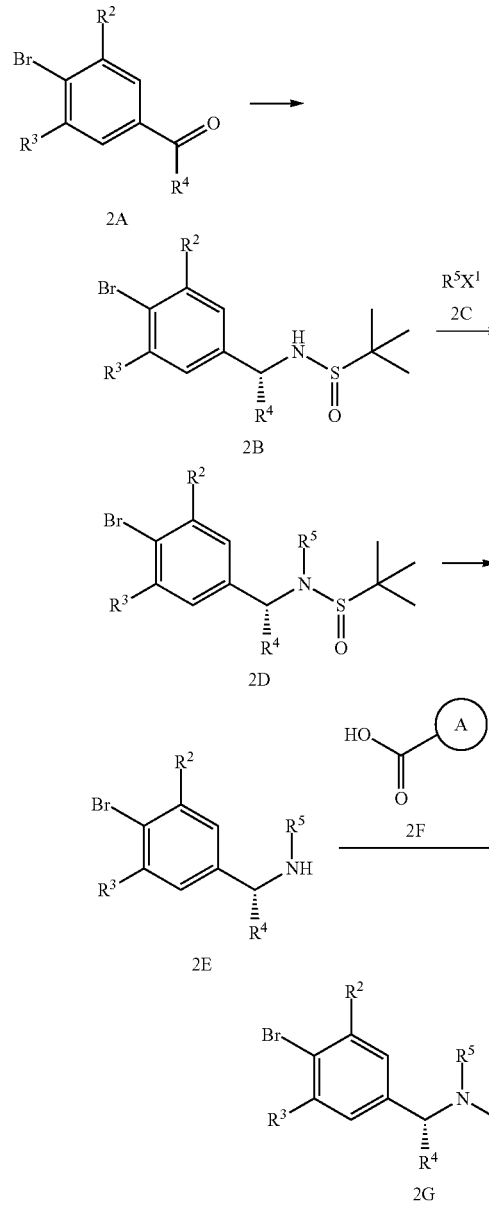

temperature, in which the elevated temperature is a temperature greater than ambient temperature, for example greater than 20° C. Compounds of Formula (1F) can be prepared by reacting compounds of Formula (1E) with diphenyl phosphorazidate in tert-butanol in the presence of a base such as triethylamine. The reaction is typically performed at an elevated temperature. Compounds of Formula (1G) can be prepared by treating compounds of Formula (1F) with an acid such as 2,2,2-trifluoroacetic acid in a solvent such as dichloromethane. The reaction may be performed at a reduced temperature.

Scheme 1 describes the synthesis of intermediates of Formula (1G). Compounds of Formula (1A) wherein $R^{1A}$, $R^{1B}$, and $R^8$ are as described herein, may be converted to compounds of Formula (1B) by reacting the former and (R)-3-hydroxy-4,4-dimethyldihydrofuran-2(3H)-one, in the presence of N,N'-dicyclohexylcarbodiimide and 4-dimethylaminopyridine. The reaction is typically performed at ambient temperature in a solvent such as, but not limited to, dichloromethane. Separation of compounds of Formula (1B) to compounds of Formula (1C) and (1D) can be performed via precipitation techniques as described herein. Compounds of Formula (1D) can be subjected to hydrolysis using a base such as lithium hydroxide, followed by the addition of an acid such as hydrochloric acid to provide compounds of Formula (1E). The reaction is typically performed in an aqueous environment and may be performed at an elevated As shown in Scheme 2, compounds of Formula (2A), wherein $R^2$, $R^3$, and $R^4$ are as described herein, can be reacted with (R)-2-methylpropane-2-sulfinamide and tetraisopropoxytitanium at an elevated temperature, followed by treatment with lithium tri-sec-butylborohydride at reduced temperature to provide compounds of Formula (2B). The reaction is typically performed in a solvent such as tetrahydrofuran. Compounds of Formula (2D) can be prepared by treating compounds of Formula (2B) with sodium hydride at a reduced temperature followed by addition of a compound of Formula (2C), wherein $R^5$ and $\lambda^1$ are as described herein, in a solvent such as, but not limited to, tetrahydrofuran. Compounds of Formula (2D) can be treated with hydrochloric acid in a solvent such as 1,4-dioxane, methanol, or a mixture thereof, to provide compounds of Formula (2E). Compounds of Formula (2F), wherein A is as described herein, can be treated with oxalyl chloride at ambient temperature to provide an intermediate acid chloride, followed by reaction with compounds of Formula (2E) and a base such as but not limited to N,N-diisopropylethylamine, to provide compounds of Formula (2G). The reaction is typically performed in a solvent such as dichloromethane, N,N-dimethylformamide, or mixtures thereof.

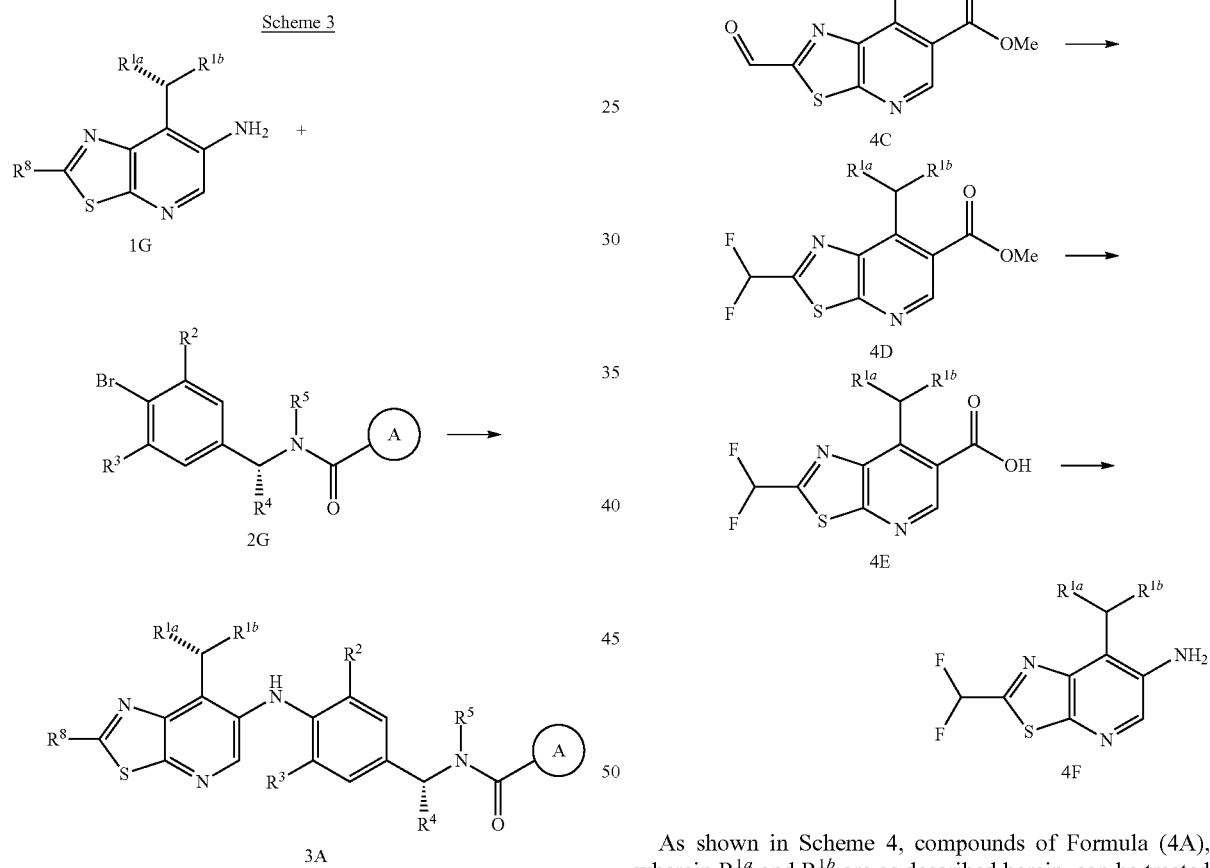

Scheme 3 describes the synthesis of compounds of Formula (3A), which are representative of compounds of Formula (I). Compounds of Formula (1G), wherein $R^{1A}$, $R^{1B}$, and $R^8$ are as described herein, can be coupled to compounds of Formula (2G), wherein $R^2$, $R^3$, $R^4$, $R^5$ and A are as described herein, under Buchwald coupling reaction conditions, which may include the use of a base such as, but not limited to, cesium carbonate and a catalyst such as, but not limited to, XantPhos Pd G3, to provide compounds of Formula (3A). The reaction is typically performed at an elevated temperature in a solvent such as, but not limited to, 1,4-dioxane.

As shown in Scheme 4, compounds of Formula (4A), wherein $R^{1a}$ and $R^{1b}$ are as described herein, can be treated with iodomethane in the presence of a base such as, but not limited to, potassium carbonate to provide compounds of Formula (4B). The reaction is typically performed at ambient temperature in a solvent such as, but not limited to, N,N-dimethylformamide. Compounds of Formula (4B) can be treated with selenium dioxide to provide compounds of Formula (4C). The reaction is typically performed at elevated temperature in a solvent such as, but not limited to, 1,4-dioxane. Compounds of Formula (4D) can be prepared by treating compounds of Formula (4C) with [bis(2-methoxyethyl)amino]sulfur trifluoride at low temperature, followed by heat. The reaction is typically performed in a solvent such as, but not limited to, toluene. Treatment of compounds of Formula (4D), at ambient temperature, with a base, such as sodium carbonate, in a solvent, such as methanol, will provide compounds of Formula (4E). Compounds of Formula (4F) can be prepared by reacting compounds of Formula (4E) with diphenyl phosphorazidate in tert-butanol in the presence of a base such as triethylamine. The reaction is typically performed at an elevated temperature. Compounds of Formula (4F) can be utilized as described in Scheme 3 to provide compounds of Formula (I).

Formula (5B), to provide compounds of Formula (5C), which are representative of compounds of Formula (I).

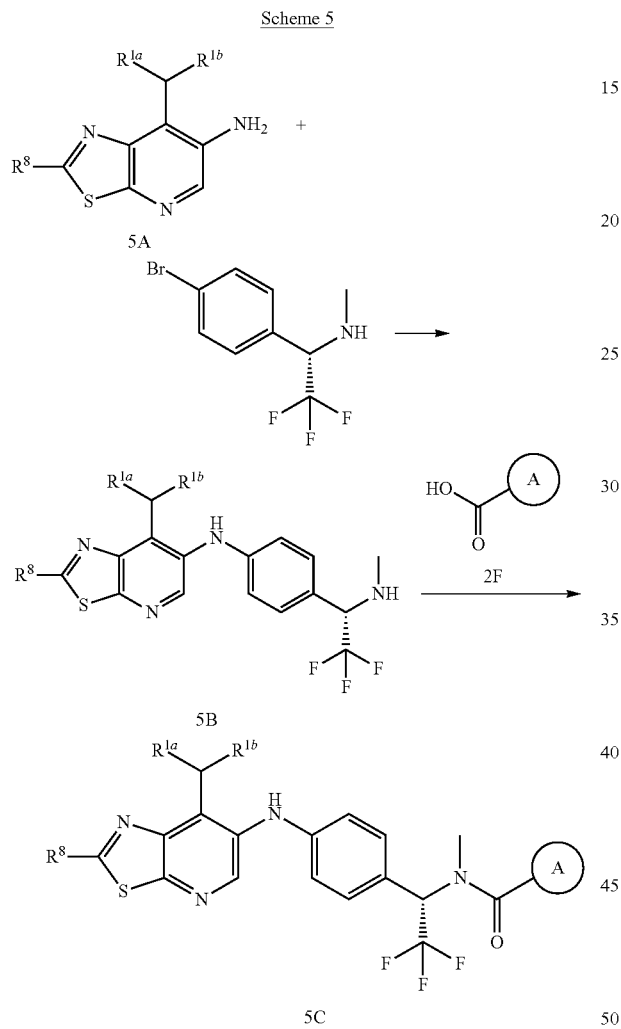

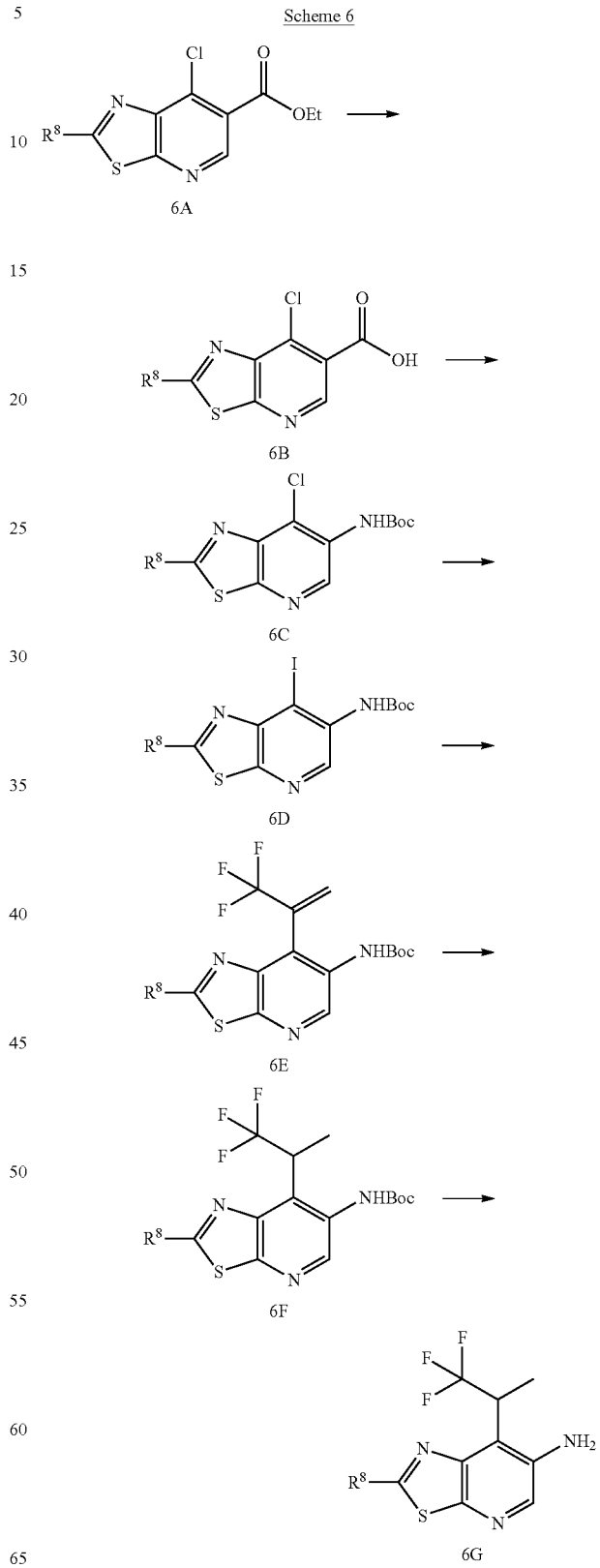

Scheme 5 describes the synthesis of compounds of Formula (5C), which are representative of compounds of Formula (I). Compounds of Formula (5A), wherein $R^8$, $R^{1a}$, and $R^{1b}$ are as described herein, can be coupled to (S)-1-(4-bromophenyl)-2,2,2-trifluoro-N-methylethan-1-amine under Buchwald coupling reaction conditions, which may include the use of a base such as, but not limited to, cesium carbonate and a catalyst such as, but not limited to, XantPhos Pd G3 to provide compounds of Formula (5B). The reaction is typically performed at an elevated temperature in a solvent such as, but not limited to, 1,4-dioxane. Compounds of Formula (2F), wherein A is as described herein, can be treated with 2,4-dichloro-6-methoxy-1,3,5-triazine and N-methylmorpholine in dichloromethane at ambient temperature, followed by the addition of compounds of As shown in Scheme 6, compounds of Formula (6A), wherein $R^8$ is as described herein, can be treated with a base such as, but not limited to, LiOH to provide compounds of Formula (6B). The reaction is typically performed at ambient temperature in an aqueous solvent system such as, but not limited to, a mixture of water and 1,4-dioxane. Compounds of Formula (6C) can be prepared by reacting compounds of Formula (6B) with diphenyl phosphorazidate in tert-butanol in the presence of a base such as triethylamine. The reaction is typically performed at an elevated temperature. Compounds of Formula (6C) can be treated with sodium iodide and acetyl chloride to provide compounds of Formula (6D). The reaction is typically performed at a reduced temperature in a solvent such as, but not limited to, acetonitrile. Compounds of Formula (6E) can be prepared by reacting compounds of Formula (6D) with 4,4,6-trimethyl-2-(3,3,3-trifluoroprop-1-en-2-yl)-1,3,2-dioxaborinane in the presence of a base such as, but not limited to, cesium carbonate and a catalyst such as, but not limited to, [bis(diphenylphosphino)ferrocene]dichloropalladium(II)-dichloromethane. The reaction is typically performed at an elevated temperature and may be heated via microwave irradiation, and in a solvent such as 1,2dimethoxyethane, water, or mixtures thereof. Compounds of Formula (6E) can be treated with hydrogen gas and palladium (5 weight % on carbon) to provide compounds of Formula (6F). The reaction is typically performed at an elevated temperature in a solvent such as, but not limited to, ethanol. Compounds of Formula (6G) can be prepared by treating compounds of Formula (6F) with 2,2,2-trifluoroacetic acid in dichloromethane at ambient temperature. Compounds of Formula (6G) can be utilized as described in Scheme 3 to provide compounds of Formula (I).

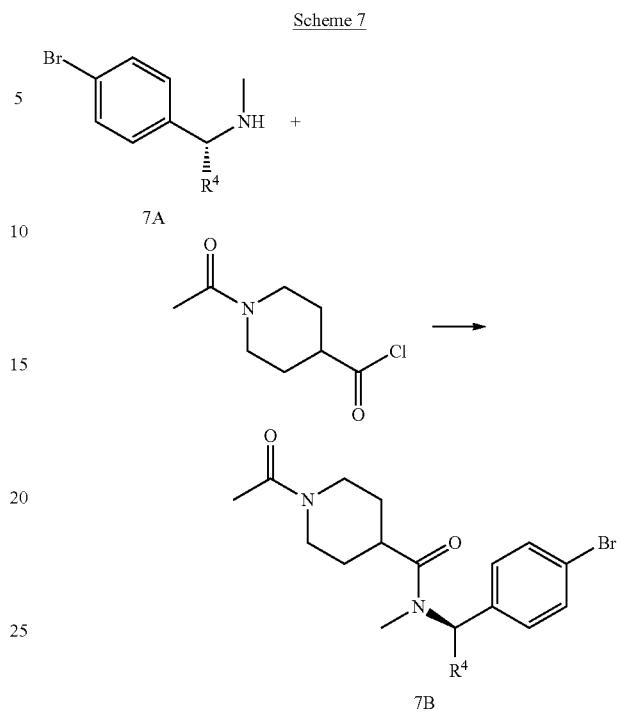

Scheme 7

Scheme 7 describes the synthesis of compounds of Formula (7B), which can be used as an intermediate in the synthesis of compounds of Formula (I). Compounds of Formula (7A), wherein $R^4$ is as described herein, can be reacted with 1-acetylpiperidine-4-carbonyl chloride in the presence of pyridine and N,N-dimethylpyridin-4-amine to provide compounds of Formula (7B).

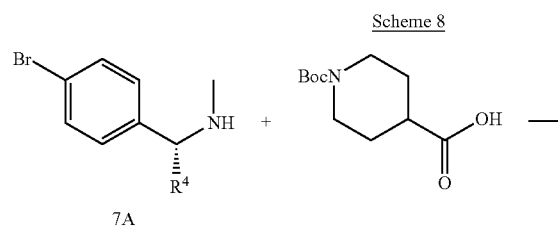

Scheme 8

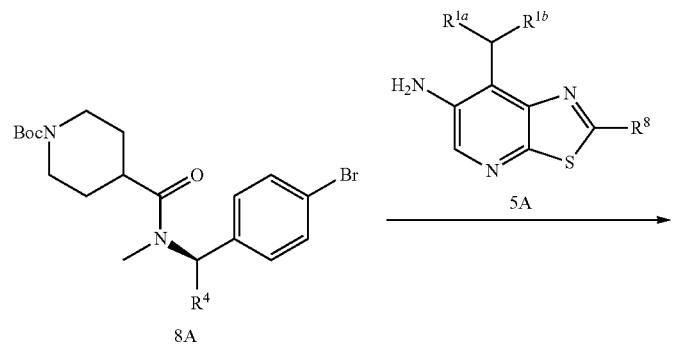

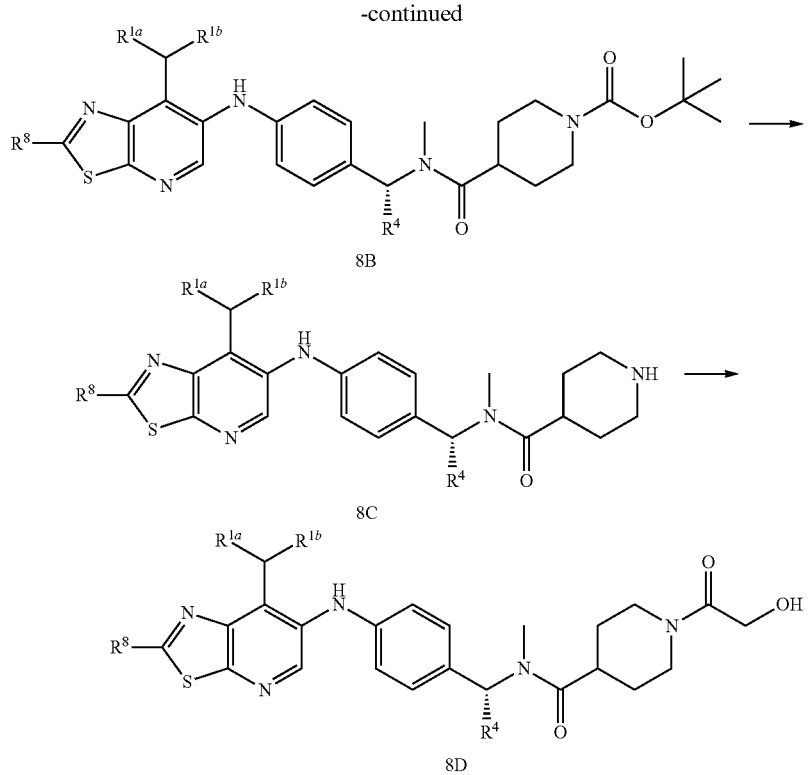

1-(tert-Butoxycarbonyl)piperidine-4-carboxylic acid can be treated with oxalyl chloride at ambient temperature to provide the intermediate acid chloride, followed by reaction with compounds of Formula (7A), wherein $R^4$ is as described herein, and a base such as but not limited to N,N-diisopropylethylamine, to provide compounds of Formula (8A). The reaction is typically performed at low temperature in a solvent such as dichloromethane, N,N-dimethylformamide, or mixtures thereof. Compounds of Formula (8A) can be reacted with a compound of Formula (5A) under Buchwald coupling conditions, which include the presence of a base such as, but not limited to, cesium carbonate and a catalyst such as but not limited to XPhos Pd G3, to provide compounds of Formula (8B). The reaction is typically performed at an elevated temperature in a solvent such as, but not limited to, dioxane. Compounds of Formula (8C) can be prepared by treating compounds of Formula (8B) with an acid such as 2,2,2-trifluoroacetic acid in a solvent such as dichloromethane. Compounds of Formula (8D), which are representative of compounds of Formula (I), can be prepared by reacting compounds of Formula (8C) with 2-hydroxyacetic acid in the presence of a coupling agent such as but not limited to 1-[bis(dimethylamino)methylene]-1H-1,2,3-triazolo[4,5-b]pyridinium 3-oxid hexafluorophosphate, and a base such as, but not limited to, N,N-diisopropylethylamine. The reaction is typically performed at ambient temperature in a solvent such as, but not limited to, N,N-dimethylformamide.

It can be appreciated that the synthetic schemes and specific examples as illustrated in the synthetic examples section are illustrative and are not to be read as limiting the scope of the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Specific procedures are provided in the Synthetic Examples section. Unless otherwise described, the starting materials and reagents are either commercially available or may be prepared by one skilled in the art from commercially available materials using methods described in the chemical literature.

Pharmaceutical Compositions

When employed as a pharmaceutical, a compound of the present disclosure may be administered in the form of a pharmaceutical composition. Such composition may a therapeutically effective amount of a compound of Formula (I) or a pharmaceutically acceptable salt thereof, together with a pharmaceutically acceptable carrier.

Method of Use

The compounds of Formula (I) or pharmaceutically acceptable salts thereof, and pharmaceutical compositions comprising a compound of Formula (I) or a pharmaceutically acceptable salt thereof, may be administered to a subject suffering from ABC-DLBCL. The term "administering" refers to the method of contacting a compound with a subject in need thereof.

In another embodiment, compounds of the present disclosure, or pharmaceutical compositions comprising a compound of the present disclosure, may be for use in medicine. In a particular embodiment, compounds of the present disclosure, or pharmaceutical compositions comprising a compound of the present disclosure, may be for use in the treatment of diseases or disorders as described herein above, including ABC-DLBCL.

The present disclosure is also directed to the use of a compound according to Formula (I), or a pharmaceutically acceptable salt thereof, in the manufacture of a medicament for the treatment of ABC-DLBCL.

EXAMPLES

The following Examples may be used for illustrative purposes and should not be deemed to narrow the scope of the present disclosure.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference.

The following abbreviations have the indicated meaning unless otherwise specified: NMR for nuclear magnetic resonance; s for singlet; br s for broad singlet; d for duplet or doublet; m for multiplet; t for triplet; q for quartet; LC/MS or LCMS for liquid chromatography-mass spectrometry; min for minute; mL for milliliter; μL for microliter; L for liter; g for gram; mg for milligram; mmol for millimoles; HPLC for high pressure liquid chromatography; ppm for parts per million; DCI for desorption chemical ionization; DSI for droplet spray ionization; ESI for electrospray ionization; M for molarity (moles/liter); N for normality (equivalent/liter); and APCI for atmospheric pressure chemical ionization.

Example 1

N-methyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1λ$^6$-thiane-4-carboxamide Example 1A (R)-4,4-dimethyl-2-oxotetrahydrofuran-3-yl 7-(1-methoxyethyl)-2-methylthiazolo[5,4-b]pyridine-6-carboxylate N,N'-dicyclohexylcarbodiimide (175 g) and 4-dimethylaminopyridine (9.44 g) were added to a solution of 7-(1-methoxyethyl)-2-methylthiazolo[5,4-b]pyridine-6-carboxylic acid (195 g, WO2018020474A1) in dichloromethane (2 L), and the reaction mixture was stirred at 20° C. for 10 minutes. (R)-3-hydroxy-4,4-dimethyldihydrofuran-2(3H)-one (101 g) was added, and the reaction mixture was stirred at 20° C. for 3 hours. The reaction mixture was concentrated in vacuo to afford a residue, which was triturated with tetrahydrofuran (2.5 L) at 50° C. for 30 minutes. The reaction mixture was concentrated in vacuo to reduce the volume to approximately 400 mL and stirred at 20° C. for 30 minutes. The precipitate was collected by filtration to afford the title compound. $^1$H NMR (400 MHz, CDCl$_3$) δ ppm 8.78 (s, 0.2H), 8.70 (s, 1H), 5.67 (s, 1H), 5.63 (s, 0.2H), 5.45-5.39 (m, 0.2H), 5.36 (q, 1H), 4.12 (s, 2H), 3.30 (s, 3H), 3.30-3.29 (m, 0.7H), 2.90 (s, 3H), 1.78 (d, 0.7H), 1.74 (d, 3H), 1.36 (s, 3H), 1.35 (br s, 0.7H), 1.25 (s, 3H), 1.19 (s, 0.7H).

Example 1B (R)-4,4-dimethyl-2-oxotetrahydrofuran-3-yl 7-((S)-1-methoxyethyl)-2-methylthiazolo[5,4-b]pyridine-6-carboxylate; and Example 1C (R)-4,4-dimethyl-2-oxotetrahydrofuran-3-yl 7-((R)-1-methoxyethyl)-2-methylthiazolo[5,4-b]pyridine-6-carboxylate Example 1A (370 g) in tetrahydrofuran (3 L) was stirred at 70° C. for 30 minutes. The mixture was concentrated in vacuo to reduce the volume to about 1 L and then stirred at 25° C. for 30 minutes. The resultant precipitate was collected by filtration to afford the crude product. The process was repeated 3 times, and the precipitate was collected by filtration to obtain Example 1B. The mother liquor of the first filtration was concentrated in vacuo to afford Example 1C. Example 1B: $^1$H NMR (400 MHz, CDCl$_3$) δ ppm 8.70 (s, 1H), 5.68 (s, 1H), 5.37 (q, 1H), 4.12 (s, 2H), 3.30 (s, 3H), 2.90 (s, 3H), 1.75 (d, 3H), 1.36 (s, 3H), 1.25 (s, 3H). Chiral purity of the combined Example 1B: 97.66% de. Chiral purity of Example 1C: 92% de.

Example 1D (S)-7-(1-methoxyethyl)-2-methylthiazolo[5,4-b]pyridine-6-carboxylic acid A mixture of Example 1B (230 g) and lithium hydroxide hydrate (79 g) in water (1.2 L) was stirred at 80° C. for 1.5 hours. The reaction mixture was filtered, and the filtrate was diluted with water (2 L). 6 M Aqueous HCl was added to adjust the pH to 1.57. The mixture was heated to 100° C. over a period of 50 minutes and then stirred at 100° C. for 30 minutes. The mixture was cooled to 25° C. over a period of 5 hours and stirred for 30 minutes. The precipitate was collected by filtration to afford the crude product, which was triturated with water (2 L) for 30 minutes at 25° C. The precipitate was collected by filtration, air-drying over a period of 3 hours, and then dried in vacuo at 50° C. for 6 hours to afford the title compound. $^1$H NMR (400 MHz, CDCl$_3$) δ ppm 9.13 (s, 1H), 5.91-5.83 (m, 1H), 3.47 (s, 3H), 2.89 (s, 3H), 1.73 (d, 3H). One exchangeable proton was not observed.

Example 1E tert-butyl (S)-(7-(1-methoxyethyl)-2-methylthiazolo[5,4-b]pyridin-6-yl)carbamate To a solution of Example 1D (20 g) in tert-butanol (305 mL) at 40° C. under atmosphere of nitrogen, was added triethylamine (14.36 mL). The mixture was heated to 60° C., and diphenyl phosphorazidate (18.79 mL) was added dropwise over about 6 minutes. The reaction mixture was stirred at 60° C. for 5 hours. After cooling to ambient temperature, sodium hydroxide (5 weight % in water, 60 mL) was added to the reaction mixture, which was then concentrated in vacuo. Water (200 mL) was added, and the suspension was stirred for 15 minutes. The precipitate was collected by filtration, washed with water (2×200 mL), and air-dried for 1 hour. To the precipitate was added ethyl acetate (600 mL), and the resulting suspension was warmed to about 40° C. and stirred until a slightly cloudy solution formed. The solution was cooled to ambient temperature, stirred for 30 minutes, and filtered. The filtrate was concentrated in vacuo to afford the title compound. $^1$H NMR (600 MHz, CDCl$_3$) δ ppm 9.30 (s, 1H), 8.40 (s, 1H), 5.57 (q, 1H), 3.38 (s, 3H), 2.81 (s, 3H), 1.56 (d, 9H). MS (ESI) m/z 324.3 (M+H)$^+$.

Example 1F (S)-7-(1-methoxyethyl)-2-methylthiazolo[5,4-b]pyridin-6-amine

To a solution of Example 1E (22.9 g) in anhydrous dichloromethane (201 mL) at 10° C., was added 2,2,2-trifluoroacetic acid (46.4 mL) over a period of 7 minutes. The reaction mixture was stirred overnight at ambient temperature and then concentrated in vacuo. Dichloromethane (100 mL) was added, and disodium hydrogen phosphate (1 M in water) was added to adjust to neutral pH. The phases were separated, and the organic layer was washed with brine, dried over sodium sulfate, and filtered. The filtrate was concentrated in vacuo. Ethyl acetate (150 mL) was added, and the resulting suspension was stirred for 5 minutes and filtered. The filtrate was diluted with heptane (150 mL), stirred for 5 minutes, and filtered. The filtrate was concentrated in vacuo to about 80 mL. Heptane (150 mL) was added and the mixture was stirred for 5 minutes at 70° C. The mixture was cooled to ambient temperature and the precipitate was collected by filtration to afford the title compound. $^1$H NMR (600 MHz, CDCl$_3$) δ ppm 7.99 (s, 1H), 5.50 (q, 1H), 4.16 (s, 2H), 3.35 (s, 3H), 2.79 (s, 3H), 1.57 (d, 3H). MS (ESI) m/z 224.2 (M+H)$^+$.

Example 1G (R)—N—((S)-1-(4-bromophenyl)-2,2,2-trifluoroethyl)-2-methylpropane-2-sulfinamide A mixture of 1-(4-bromophenyl)-2,2,2-trifluoroethanone (3.01 mL), (R)-2-methylpropane-2-sulfinamide (2.99 g) and tetraisopropoxytitanium (14.63 mL) was dissolved in tetrahydrofuran (200 mL) and stirred at 50° C. overnight. The reaction mixture was cooled to −78° C., lithium tri-sec-butylborohydride (1 M in tetrahydrofuran, 59.3 mL) was added, and the reaction mixture stirred at −78° C. for 3 hours. Brine (50 mL) was added to the reaction mixture, which was allowed to warm to ambient temperature. The reaction mixture was filtered through diatomaceous earth and washed with ethyl acetate (200 mL). The phases were separated, and the aqueous layer was extracted with ethyl acetate (2×100 mL). The combined organic layers were dried over magnesium sulfate and filtered. The filtrate was concentrated in vacuo. The crude material was purified by chromatography on silica gel (0-100% ethyl acetate/2-methylpentane) to afford the title compound. $^1$H NMR (400 MHz, CDCl$_3$) δ ppm 7.58-7.52 (m, 2H), 7.33-7.30 (m, 2H), 4.80 (p, 1H), 3.59 (d, 1H), 1.25 (s, 9H). MS (ESI) m/z 358/360 (M+H)$^+$.

Example 1H (R)—N—((S)-1-(4-bromophenyl)-2,2,2-trifluoroethyl)-N-2-dimethylpropane-2-sulfinamide At 0° C., sodium hydride (0.475 g) was added portionwise to a solution of Example 1G (3.73 g) in tetrahydrofuran (50 mL), and the reaction mixture stirred at 0° C. for 2 hours. Iodomethane (3.26 mL) was added to the reaction mixture, which was stirred for 10 minutes at 0° C. and a further 10 minutes at ambient temperature. Saturated aqueous ammonium chloride (50 mL) and ethyl acetate (50 mL) were added. The layers were separated, and the aqueous layer was extracted with ethyl acetate (2×50 mL). The combined organic layers were washed with water (50 mL), brine (50 mL), dried over magnesium sulfate and filtered. The filtrate was concentrated in vacuo. The crude material was purified by chromatography on silica gel (0-60% ethyl acetate/2-methylpentane) to afford the title compound. $^1$H NMR (400 MHz, CDCl$_3$) δ ppm 7.56-7.49 (m, 2H), 7.39-7.30 (m, 2H), 5.05 (q, 1H), 2.45 (s, 3H), 1.25 (s, 9H). MS (ESI) m/z 372.1/374.2 (M+H)$^+$.

Example 1I (S)-1-(4-bromophenyl)-2,2,2-trifluoro-N-methylethanamine

To a solution of Example 1H (1.90 g) in 1,4-dioxane (15 mL) and methanol (15 mL) was added 4 M HCl in 1,4-dioxane (5.10 mL), and the reaction mixture was stirred at ambient temperature for 2 hours. The solution was concentrated in vacuo and 0.5 M aqueous HCl (80 mL) was added. The aqueous layer was extracted with ethyl acetate (3×30 mL). Sodium hydroxide (2 M in water) was added to the aqueous layer to adjust to pH 14, and the aqueous layer was extracted with ethyl acetate (3×40 mL). The combined organic layers were dried over magnesium sulfate and filtered. The filtrate was concentrated in vacuo to afford the title compound. $^1$H NMR (400 MHz, DMSO-d$_6$) δ ppm 7.64-7.58 (m, 2H), 7.47-7.38 (m, 2H), 4.30 (p, 1H), 2.87 (dq, 1H), 2.20 (d, 3H). MS (ESI) m/z 268.1/270.1 (M+H)$^+$.

Example 1J (S)—N-(1-(4-bromophenyl)-2,2,2-trifluoroethyl)-N-methyltetrahydro-2H-thiopyran-4-carboxamide 1,1-dioxide To a solution of tetrahydro-2H-thiopyran-4-carboxylic acid 1,1-dioxide (0.83 g) in dichloromethane (20 mL) was added oxalyl chloride (0.41 mL) and N,N-dimethylformamide (0.014 mL). The reaction mixture was stirred at ambient temperature for 1 hour and then concentrated in vacuo. The residue was dissolved in dichloromethane (10 mL) and added to a solution of Example 1I (0.96 g) and N,N-diisopropylethylamine (1.876 mL) in dichloromethane (10 mL). The reaction mixture was stirred at ambient temperature for 90 minutes and dichloromethane (20 mL) and brine (30 mL) were added. The phases were separated, and the aqueous layer was extracted with dichloromethane (2×30 mL). The combined organic layers were washed with saturated aqueous sodium hydrogen carbonate (2×30 mL), dried over magnesium sulfate, and filtered. The filtrate was concentrated in vacuo. The crude material was purified by chromatography on silica gel (0-10% methanol/dichloromethane) to afford the title compound. $^1$H NMR (400 MHz, DMSO-d$_6$) δ ppm 7.67 (d, 2H), 7.32 (d, 2H), 6.54 (q, 1H), 3.31-3.00 (m, 5H), 2.88 (s, 3H), 2.18-1.89 (m, 4H). MS (ESI) m/z 428/430 (M+H)$^+$. Example 1K N-methyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1λ$^6$-thiane-4-carboxamide To a degassed mixture of Example 1F (60 mg), Example 1J (127 mg) and cesium carbonate (263 mg) in 1,4-dioxane (6 mL) was added XantPhos Pd G3 ([(4,5-Bis(diphenylphosphino)-9,9-dimethylxanthene)-2-(2'-amino-1,1'-biphenyl)]palladium(II) methanesulfonate) (25.5 mg), and the reaction mixture was stirred at 90° C. for 16 hours. The reaction mixture was cooled to ambient temperature, filtered through diatomaceous earth, washed with ethyl acetate (20 mL) and concentrated in vacuo. The crude material was purified by chromatography on silica gel (0-80% ethyl acetate-ethanol (3:1)/2-methylpentane) and the residue was precipitated from dichloromethane/2-methylpentane to afford the title compound. $^1$H NMR (400 MHz, DMSO-$d_6$, 90° C.) δ ppm 8.48 (s, 1H), 7.57 (s, 1H), 7.25 (d, 2H), 7.10-7.01 (m, 2H), 6.42 (s, 1H), 5.39 (q, 1H), 3.27 (s, 3H), 3.24-3.03 (m, 5H), 2.91 (s, 3H), 2.83 (s, 3H), 2.10 (td, 4H), 1.54 (d, 3H). MS (ESI) m/z 571.2 (M+H)$^+$.

Example 2

N-methyl-1,1-dioxo-N-{(1S)-2,2,2-trifluoro-1-[4-({2-methyl-7-[(1R)-2,2,2-trifluoro-1-methoxyethyl][1,3]thiazolo[5,4-b]pyridin-6-yl}amino)phenyl]ethyl}-1λ$^6$-thiane-4-carboxamide Example 1IG (50 mg, 0.180 mmol), Example 1J (85 mg, 0.198 mmol), XPhos Pd G2 (14.19 mg, 0.018 mmol) and cesium carbonate (176 mg, 0.541 mmol) were mixed in 1,4-dioxane (0.9 mL). The mixture was sparged with nitrogen for 10 minutes and the reaction vial was sealed. The reaction was stirred at 95° C. for 16 hours. After cooling, the reaction mixture was directly loaded onto a 40 g silica gel column. The crude material was purified by flash chromatography (0-100% ethyl acetate/heptanes) to afford the title compound. $^1$H NMR (600 MHz, DMSO-$d_6$) δ ppm 8.59 (s, 1H), 7.60 (s, 1H), 7.24 (d, J=8.4 Hz, 2H), 7.14 (d, J=8.6 Hz, 2H), 6.46 (q, J=9.3 Hz, 1H), 5.93 (q, J=7.6 Hz, 1H), 3.52 (s, 3H), 3.30-3.07 (m, 5H), 2.91 (s, 3H), 2.86 (s, 3H), 2.16-1.97 (m, 4H). MS (APCI) m/z 625.3 (M+H)$^+$.

Example 3

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1λ$^6$-thiane-4-carboxamide Example 3A ethyl 2-methyl-7-vinylthiazolo[5,4-b]pyridine-6-carboxylate To a mixture of ethyl 7-chloro-2-methylthiazolo[5,4-b]pyridine-6-carboxylate (60 g, 234 mmol, WO2018020474A1, Example 16, step 2) in 1,4-dioxane (600 mL) and water (100 mL) was added 4,4,5,5-tetramethyl-2-vinyl-1,3,2-dioxaborolane (72.0 g, 467 mmol), tetrakis(triphenylphosphine)palladium(0) (27.0 g, 23.37 mmol) and Na$_2$CO$_3$ (61.9 g, 584 mmol). The mixture was stirred at 100° C. for 12 hours after which another batch of 4,4,5,5-tetramethyl-2-vinyl-1,3,2-dioxaborolane (14.4 g, 93.4 mmol), tetrakis(triphenylphosphine)palladium(0) (5.4 g, 4.67 mmol), and Na$_2$CO$_3$ (12.4 g, 116.8 mmol) were added, and the mixture was stirred at 100° C. for an additional 4 hours. After cooling to 25° C., the reaction was quenched with water (500 mL) and extracted with ethyl acetate (3×1500 mL). The combined organic phase was washed with brine (300 mL), dried over Na$_2$SO$_4$, filtered, and concentrated to afford crude product. The crude product was purified by column chromatography (1:4 ethyl acetate/ petroleum ether) to afford the title compound. $^1$H NMR (400 MHz, DMSO-$d_6$) δ ppm 1.33 (t, J=7.1 Hz, 3H), 2.85 (s, 3H), 4.30-4.42 (m, 2H), 5.89-5.97 (m, 1H), 6.63-6.74 (m, 1H), 7.27-7.39 (m, 1H), 8.82 (s, 1H). LCMS (ES) m/z (M+H)$^+$ 249.2.

Example 3B 2-methyl-7-vinylthiazolo[5,4-b]pyridine-6-carboxylic acid

To a solution of Example 3A (120 g, 483 mmol) in 1,4-dioxane (960 mL) and water (720 mL) was added lithium hydroxide (17.36 g, 725 mmol) and the reaction was stirred at 20° C. for 2 hours. The mixture was concentrated under vacuum to remove most 1,4-dioxane. The pH was adjusted to about 3 with 2 M aqueous HCl and the mixture was filtered. The filter cake was washed with water (1000 mL), dissolved in tetrahydrofuran (1000 mL), dried over MgSO$_4$, filtered, and concentrated to afford the title compound. $^1$H NMR (300 MHz, DMSO-$d_6$) δ ppm 2.87 (s, 3H), 5.95 (dd, J=11.7, 2.1 Hz, 1H), 6.74 (dd, J=17.6, 2.1 Hz, 1H), 7.45 (dd, J=17.6, 11.7 Hz, 1H), 8.87 (s, 1H), 13.62 (s, 1H). LCMS (ES) m/z 221 (M+H)$^+$.

Example 3C tert-butyl (2-methyl-7-vinylthiazolo[5,4-b]pyridin-6-yl)carbamate

To a mixture of Example 3B (73 g, 331 mmol, dried by oven), triethylamine (138 mL, 994 mmol, dried with molecular sieves) in toluene (1095 mL, dried with molecular sieves) was added diphenylphosphoryl azide (137 g, 497 mmol). After being stirred for 1 hour at 20° C., tert-butanol (91 mL, 994 mmol, dried with molecular sieves) was added, and the mixture was stirred at 90° C. for 2 hours. After cooling, the mixture was concentrated to small a volume. The residue was poured into water (1000 mL) and extracted with ethyl acetate (3×500 mL). The combined organic layers were washed with brine (500 mL), dried over Na$_2$SO$_4$, filtered, and concentrated to afford a crude product. The crude product was purified by column chromatography (1:3 ethyl acetate/petroleum ether) to afford the title compound. $^1$H NMR (400 MHz, DMSO-$d_6$) δ ppm 1.46 (s, 9H), 2.86 (s, 3H), 5.89 (d, J=11.5 Hz, 1H), 6.86 (d, J=15.2 Hz, 1H), 6.93-7.06 (m, 1H), 8.43 (s, 1H), 9.09 (s, 1H). LCMS (ES) m/z 292.25 (M+H)$^+$.

Example 3D tert-butyl (7-formyl-2-methylthiazolo[5,4-b]pyridin-6-yl)carbamate

Example 3C (50 g, 172 mmol) was dissolved in acetonitrile (750 mL), water (750 mL), and tetrahydrofuran (750 mL) and treated with potassium osmate(VI) dihydrate (6.32 g, 17.16 mmol) followed by sodium periodate (110 g, 515 mmol) at 0° C. The reaction was warmed to 20° C. and stirred overnight. The mixture was filtered, and the filter cake was dissolved in dichloromethane (2500 mL) and water (2000 mL). The layers were separated, and the aqueous layer was extracted with ethyl acetate (3×1000 mL). The combined organic layers were washed with brine (800 mL), dried over MgSO$_4$, filtered, and concentrated to afford the title compound. $^1$H NMR (300 MHz, DMSO-$d_6$) δ ppm 1.53

(s, 9H), 2.93 (s, 3H), 9.41 (s, 1H), 10.17 (s, 1H), 10.81 (s, 1H). LCMS (ES) m/z 294.05 (M+H)+.

Example 3E tert-butyl (7-(2,2-difluoro-1-hydroxyethyl)-2-methylthiazolo[5,4-b]pyridin-6-yl)carbamate To a suspension of Example 3D (50 g, 170 mmol) and triphenylphosphine (71.5 g, 273 mmol) in NN-dimethyl formamide (350 mL) was added (bromodifluoromethyl)trimethylsilane (42.4 mL, 273 mmol) and the reaction mixture was stirred at 25° C. for 3 hours. 1.5 M Potassium hydroxide (352 mL, 528 mmol) was added slowly, and the reaction mixture was stirred for a further 1 hour at 0° C. The reaction was quenched with saturated aqueous NH$_4$Cl (400 mL), and the mixture was extracted with ethyl acetate (4×800 mL). The organic layers were combined and washed with brine (700 mL), dried with Na$_2$SO$_4$, filtered, and the filtrate was concentrated. The crude product was purified by column chromatography (3:7 ethyl acetate/petroleum ether) to afford tert-butyl (7-(2,2-difluoro-1-hydroxyethyl)-2-methylthiazolo[5,4-b]pyridin-6-yl)carbamate (50 g, purity 83%, contained POPh$_3$) and tert-butyl (7-(2,2-difluoro-1-hydroxyethyl)-2-methylthiazolo[5,4-b]pyridin-6-yl)carbamate (265 g, purity 65%, contained POPh$_3$). POPh$_3$ was removed in next step. $^1$H NMR (400 MHz, DMSO-d$_6$) δ ppm 1.46 (s, 9H), 2.82 (s, 3H), 5.75 (s, 1H), 6.39 (t, J=55.2 Hz, 1H), 7.28-7.43 (m, 1H), 8.87 (s, 1H), 8.98 (s, 1H). LCMS (ES) m/z 346.25 (M+H)+.

Example 3F 1-(6-amino-2-methylthiazolo[5,4-b]pyridin-7-yl)-2,2-difluoroethan-1-ol A solution of Example 3E (50 g, 145 mmol) in 4 M HCl in 1,4-dioxane (500 mL, 2000 mmol) was stirred for 4 hours at 25° C. and then filtered. The filter cake was dissolved in ethyl acetate and basified to about pH 8 with aqueous saturated sodium carbonate solution and extracted with ethyl acetate (4×600 mL). The combined organic extracts were washed with water (800 mL), saturated sodium bicarbonate solution (800 mL) and brine (800 mL). The organic layer was dried over Na$_2$SO$_4$ and filtered. The filtrate was concentrated in vacuo. The crude product was purified by column chromatography (2:3 ethyl acetate/petroleum ether) to afford the title compound. $^1$H NMR (400 MHz, DMSO-d$_6$) δ ppm 2.74 (s, 3H), 5.58 (d, J=26.5 Hz, 3H), 6.12-6.49 (m, 1H), 6.74 (s, 1H), 8.05 (s, 1H). LCMS (ES) m/z 346.01 (M+H)+.

Example 3G (R)-7-(2,2-difluoro-1-methoxyethyl)-2-methylthiazolo[5,4-b]pyridin-6-amine Example 3H (S)-7-(2,2-difluoro-1-methoxyethyl)-2-methylthiazolo[5,4-b]pyridin-6-amine To a solution of Example 3E (25 g, 102 mmol) in NN-dimethyl formamide (500 mL) at 0° C. was added sodium hydride (4.89 g, 122 mmol), and the reaction mixture was stirred for 20 minutes at 0° C. Iodomethane (15.92 g, 112 mmol) was added, and the reaction mixture stirred for 2 hours at 25° C. The reaction was quenched with half-saturated brine solution (1000 mL), and the mixture was extracted with ethyl acetate (4×600 mL). The organic layers were combined and washed with water (3×600 mL), brine (3×500 mL), dried over Na$_2$SO$_4$, and filtered. The filtrate was concentrated in vacuo. The crude racemic mixture was purified by column chromatography (1:4 ethyl acetate/petroleum ether) to afford the desired product as a mixture of enantiomers (49.3 g). The enantiomers were separated by preparative chiral SFC using a CHIRAL ART Cellulose-SB, 5*25 cm, 10 μm column. The conditions used are as follows: Mobile Phase A: CO$_2$, Mobile Phase B: isopropyl alcohol (0.5% 2 M ammonia solution in methanol); flow rate: 200 mL/minute; gradient: isocratic 20% B; column temperature: 35° C.; back pressure: 100 bar; wavelength: 220 nm. Example 3G retention time: 6.93 minutes; Example 3H retention time: 8.25 minutes. $^1$H NMR (400 MHz, DMSO-d$_6$) δ ppm 2.76 (s, 3H), 3.32 (s, 3H), 5.34-5.45 (m, 1H), 5.59 (s, 2H), 6.36-6.65 (m, 1H), 8.09 (s, 1H). LCMS (ES) m/z 260 (M+H)+.

Example 3I

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1λ$^6$-thiane-4-carboxamide To a degassed mixture of Example 3G (39 mg), Example 1J (85 mg) and cesium carbonate (147 mg) in 1,4-dioxane (2 mL) was added XantPhos Pd G3 (14.26 mg), and the reaction mixture was stirred at 90° C. for 16 hours. The reaction mixture was cooled to ambient temperature, filtered through diatomaceous earth, washing with ethyl acetate (20 mL) and concentrated in vacuo. The crude material was purified by chromatography on silica gel (0-100% ethyl acetate/2-methylpentane) to afford the title compound. $^1$H NMR (500 MHz, DMSO-d$_6$) δ ppm 8.53 (s, 1H), 8.00 (s, 1H), 7.20 (d, 2H), 6.97 (d, 2H), 6.89-6.62 (m, 1H), 5.31 (dt, 1H), 6.43 (q, 1H), 3.28 (s, 3H), 3.25-3.04 (m, 5H), 2.90 (s, 3H), 2.86 (s, 3H), 2.10-1.95 (m, 4H). MS (ESI) m/z 607.2 (M+H)+.

Example 4

N-{(1S)-2,2-difluoro-1-[4-({7-[(1S)-1-methoxyethyl]-2-methyl[1,3]thiazolo[5,4-b]pyridin-6-yl}amino)phenyl]ethyl}-N-methyl-1,1-dioxo-1λ$^6$-thiane-4-carboxamide Example 4A 1-(4-bromophenyl)-2,2-difluoroethan-1-one To a solution of 1-bromo-4-iodobenzene (50 g, 177 mmol) in tetrahydrofuran (500 mL) was added dropwise n-butyllithium (78 mL, 194 mmol). The reaction mixture was stirred at −78° C. for 30 minutes. Ethyl 2,2-difluoroacetate (24.12 g, 194 mmol) was added dropwise at −78° C. over 1 hour. The reaction mixture was stirred at −78° C. for an additional hour, and then at 0° C. for 1 hour. The reaction was quenched with aqueous 1 N HCl (15 mL) and extracted with dichloromethane (3×200 mL). The combined organic layers were washed with brine, dried over anhydrous sodium sulfate, filtered, and the filtrate was concentrated. The residue was purified by flash chromatography with ethyl acetate/ petroleum ether to afford the title compound. ¹H NMR (400 MHz, DMSO) δ ppm 7.16 (t, 1H), 7.80-7.89 (m, 2H), 7.94-8.01 (m, 2H).

Example 4B (S)-1-(4-bromophenyl)-2,2-difluoro-N-methyl-ethanamine

To a solution of Example 4A (30 g, 128 mmol), methanamine in ethyl alcohol (39.6 g, 383 mmol) and titanium (IV) isopropoxide (72.6 g, 255 mmol) in dichloromethane (450 mL) was added sodium cyanoborohydride (16.04 g, 255 mmol) portion-wise. The reaction mixture was stirred at 40° C. for 16 hours. The reaction mixture was quenched with ammonium hydroxide (33% in water) and the solvents were removed in vacuo. The residue was purified by flash chromatography (1:1 petroleum ether/dichloromethane). The enantiomers were separated on normal phase HPLC using a CHIRALPAK® OD-H column (20×250 mm, 5 micron), eluting with hexane (0.1% diethylamine)/isopropanol, 20 mL/minute; 10 minutes, to afford the title compound. ¹H NMR (400 MHz, DMSO-$d_6$) δ ppm 2.16 (s, 3H), 2.54 (d, J=3.2 Hz, 1H), 3.79-3.94 (m, 1H), 5.89-6.25 (m, 1H), 7.33-7.40 (m, 2H), 7.55-7.61 (m, 2H). MS (ESI) m/z 250 (M+H)⁺. $[\alpha]^{22.7}_D$=+50.67 ($C_{0.01}$ CH₃OH).

Example 4C

N-(4-((S)-2,2-difluoro-1-(methylamino)ethyl)phenyl)-7-((S)-1-methoxyethyl)-2-methylthiazolo[5,4-b]pyridin-6-amine Example 1F (152 mg, 0.682 mmol), Example 4B (155 mg, 0.620 mmol), XPhos Pd G2 (48.8 mg, 0.062 mmol) and cesium carbonate (606 mg, 1.859 mmol) were mixed in 1,4-dioxane (8.9 mL). The mixture was sparged with nitrogen for 5 minutes and the vessel was sealed. The reaction was stirred at 90° C. for 16 hours. After cooling, the reaction mixture was filtered and concentrated. The crude was purified by flash chromatography (40 g silica gel, 0-70% ethyl acetate/heptanes) to afford the title compound. MS (ESI) m/z 393.0 (M+H)⁺. Example 4D N-{(1S)-2,2-difluoro-1-[4-({7-[(1S)-1-methoxy-ethyl]-2-methyl[1,3]thiazolo[5,4-b]pyridin-6-yl}amino)phenyl]ethyl}-N-methyl-1,1-dioxo-1λ⁶-thiane-4-carboxamide Tetrahydro-2H-thiopyran-4-carboxylic acid 1,1-dioxide (113 mg, 0.633 mmol), 2,4-dichloro-6-methoxy-1,3,5-triazine (142 mg, 0.791 mmol), and N-methylmorpholine (87 μL, 0.791 mmol) were mixed in dichloromethane (2.7 mL) and stirred at ambient temperature for one hour. A mixture of Example 4C (207 mg, 0.527 mmol) in dichloromethane (2.7 mL) was added, and the mixture was stirred at ambient temperature overnight. The mixture was concentrated and directly purified by reverse phase HPLC (C18 Phenomenex® LUNA®, 250×50 mm, 10-90% acetonitrile/0.1% trifluoroacetic acid water solution). The fractions containing the product were concentrated and redissolved in acetonitrile. The sample was desalted by filtering through a 1 g SiliCycle SiliaPrep carbonate cartridge to afford the title compound. ¹H NMR (400 MHz, DMSO-$d_6$) δ ppm 8.46 (s, 1H), 7.49 (s, 1H), 7.26 (d, J=8.2 Hz, 2H), 7.04 (d, J=8.6 Hz, 2H), 6.66 (t, J=54.9 Hz, 1H), 5.70 (s, 1H), 5.40 (q, J=6.7 Hz, 1H), 3.28 (s, 3H), 3.25-3.06 (m, 5H), 2.93 (s, 3H), 2.83 (s, 3H), 2.09 (q, J=7.1, 5.4 Hz, 4H), 1.54 (d, J=6.6 Hz, 3H). MS (APCI) m/z 553.2 (M+H)⁺.

Example 5

N-{(1S)-1-[4-({7-[(1S)-2,2-difluoro-1-methoxy-ethyl]-2-methyl[1,3]thiazolo[5,4-b]pyridin-6-yl}amino)phenyl]-2,2,2-trifluoroethyl}-N-methyl-1,1-dioxo-1λ⁶-thiane-4-carboxamide Example 5A 7-((S)-2,2-difluoro-1-methoxyethyl)-2-methyl-N-(4-((S)-2,2,2-trifluoro-1-(methylamino)ethyl)phenyl)thiazolo[5,4-b]pyridin-6-amine Example 3H (1.00 g, 3.86 mmol), Example 1I (1.29 g, 4.24 mmol), and cesium carbonate (3.77 g, 11.6 mmol) in 1,4-dioxane (19 mL) were sparged with N₂ for 2 minutes. XPhos Pd G4 (methanesulfonato(2-dicyclohexylphosphino-2',4',6'-tri-i-propyl-1,1'-biphenyl)(2'-methylamino-1,1'-biphenyl-2-yl)palladium(ii), 0.33 g, 0.39 mmol) was added, and the reaction mixture was heated 95° C. for 16 hours. The reaction mixture was cooled, filtered through diatomaceous earth, and the diatomaceous earth pad was washed with ethyl acetate. The filtrate was concentrated. The material was purified on silica gel (0-70% ethyl acetate/heptanes) to afford the title compound. ¹H NMR (400 MHz, DMSO-$d_6$) δ ppm 8.51 (s, 1H), 7.84 (s, 1H), 7.29 (d, J=8.3 Hz, 3H), 6.95 (d, J=8.6 Hz, 2H), 6.75 (ddd, J=57.6, 54.5, 5.9 Hz, 1H), 5.34 (dt, J=13.9, 5.7 Hz, 1H), 4.10 (q, J=8.1 Hz, 1H), 3.29 (s, 3H), 2.86 (s, 3H), 2.22 (d, J=5.8 Hz, 3H). MS (ESI) m/z 447.7 (M+H)⁺.

Example 5B

N-{(1S)-1-[4-({7-[(1S)-2,2-difluoro-1-methoxy-ethyl]-2-methyl[1,3]thiazolo[5,4-b]pyridin-6-yl}amino)phenyl]-2,2,2-trifluoroethyl}-N-methyl-1,1-dioxo-1λ⁶-thiane-4-carboxamide Tetrahydro-2H-thiopyran-4-carboxylic acid 1,1-dioxide (0.60 g, 3.36 mmol), 2,4-dichloro-6-methoxy-1,3,5-triazine (0.65 g, 3.58 mmol), CH₂Cl₂ (50 mL), and N-methylmorpholine (0.394 mL, 3.58 mmol) were stirred at ambient temperature for 1 hour. To this solution was added Example 5A (1.00 g, 2.24 mmol) and the combined solution was stirred at ambient temperature for 15 hours. Upon completion as determined by LCMS, the reaction mixture was concentrated. The residue was purified on silica gel (0-100% ethyl acetate/heptanes) to afford a residue. This residue was further purified by reverse phase chromatography (C18 250×50 mm C18 Phenomenex® LUNA® HPLC column, eluting with 20-100% acetonitrile in water/0.1% trifluoroacetic acid) to isolate the title compound. Clean fractions were combined and concentrated to remove acetonitrile. The aqueous solution was partitioned with ethyl acetate and neutralized with saturated aqueous sodium bicarbonate to free base the desired product. The organic layer was dried with anhydrous magnesium sulfate, filtered, and the filtrate was concentrated. The residue was lyophilized to provide the title compound. ¹H NMR (600 MHz, DMSO-$d_6$) δ ppm 8.53 (s, 1H), 7.99 (s, 1H), 7.21 (d, J=8.3 Hz, 2H), 7.01-6.92 (m, 2H), 6.75 (ddd, J=57.7, 54.3, 5.9 Hz, 1H), 6.44 (q, J=9.3 Hz, 1H), 5.31 (dt, J=14.1, 5.5 Hz, 1H), 3.28 (s, 3H), 3.26-3.06 (m, 4H), 2.91 (s, 3H), 2.86 (s, 3H), 2.17-1.91 (m, 4H). MS (ESI+) m/z 607.3 (M+H)+.

Example 6

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-N-methyl-1,1-dioxo-1$\lambda^6$-thiane-4-carboxamide

Example 6A

N-(4-((S)-2,2-difluoro-1-(methylamino)ethyl)phenyl)-7-((R)-2,2-difluoro-1-methoxyethyl)-2-methylthiazolo[5,4-b]pyridin-6-amine The title compound (235 mg, 86%) was prepared using the conditions described in Example 4C substituting Example 3G for Example 1F. MS (APCI) m/z 429.3 (M+H)+.

Example 6B

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-N-methyl-1,1-dioxo-1$\lambda^6$-thiane-4-carboxamide The title compound (145 mg, 45%) was prepared using the conditions described in Example 4D substituting Example 6A for Example 4C. $^1$H NMR (400 MHz, DMSO-$d_6$) δ ppm 8.48 (s, 1H), 7.61 (s, 1H), 7.24 (d, J=8.2 Hz, 2H), 7.07-6.89 (m, 2H), 6.66 (ddd, J=56.8, 54.8, 5.5 Hz, 2H), 5.70 (s, 1H), 5.40 (ddd, J=13.0, 7.3, 5.5 Hz, 1H), 3.37 (s, 3H), 3.32-3.04 (m, 5H), 2.93 (s, 3H), 2.85 (s, 3H), 2.21-1.95 (m, 4H). MS (APCI) m/z 589.3 (M+H)+.

Example 7

N-ethyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1$\lambda^6$-thiane-4-carboxamide

Example 7A (S)-1-(4-bromophenyl)-N-ethyl-2,2,2-trifluoroethanamine

To a solution of Example 1I (0.4 g, 1.575 mmol) in methanol (5.3 mL) was added acetaldehyde (0.088 mL, 1.575 mmol) dropwise. The mixture was stirred at ambient temperature for 1 hour, followed by the addition of sodium borohydride (0.119 g, 3.15 mmol). The stirring continued for 18 hours. The reaction was quenched by water and extracted with dichloromethane. The combined organic layers were concentrated and purified by reverse phase HPLC (250×50 mm Phenomenex® LUNA® C18, 10-90% acetonitrile/0.1% trifluoroacetic acid water solution) to afford the title compound (100 mg, 16.03%). MS (APCI) m/z 282.2 (M+H)+.

Example 7B (S)—N-(1-(4-bromophenyl)-2,2,2-trifluoroethyl)-N-ethyltetrahydro-2H-thiopyran-4-carboxamide 1,1-dioxide To a solution of tetrahydro-2H-thiopyran-4-carboxylic acid 1,1-dioxide (0.084 g, 0.47 mmol) in dichloromethane (1.880 mL) was added oxalyl chloride (0.470 mL, 0.940 mmol) and N,N-dimethylformamide (3.64 µL, 0.047 mmol) at 0° C. The mixture was stirred for 1 hour while warming to ambient temperature. The reaction was concentrated to afford crude tetrahydro-2H-thiopyran-4-carbonyl chloride 1,1-dioxide, which was mixed in dichloromethane (0.8 mL). The suspension was dropwise added to a solution of Example 7A (66.3 mg, 0.235 mmol) and triethylamine (0.07 mL, 0.470 mmol) in dichloromethane (0.8 mL). The reaction was stirred at ambient temperature for 20 hours. The mixture was directly purified by flash chromatography (12 g silica gel, 0-70% acetone/heptanes) to afford the title compound (15 mg, 14.43%). MS (APCI) m/z 442.1 (M+H)+.

Example 7C

N-ethyl-1,1-dioxo-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}-1$\lambda^6$-thiane-4-carboxamide Example 1F (19.69 mg, 0.088 mmol), Example 7B (30 mg, 0.068 mmol), XPhos Pd G2 (5.34 mg, 6.78 µmol) and cesium carbonate (66.3 mg, 0.203 mmol) were mixed in 1,4-dioxane (1.0 mL). The mixture was sparged with nitrogen for 5 minutes and the vessel was sealed. The reaction was stirred at 90° C. for 16 hours. After cooling, the reaction mixture was filtered and concentrated. The residue was purified by reverse phase HPLC (250×50 mm C18 Phenomenex® LUNA®, 10-90% acetonitrile/0.1% trifluoroacetic acid water solution). The collected fractions containing the product were concentrated and re-purified by flash chromatography (12 g silica gel, 0-100% ethyl acetate/heptanes) to afford the title compound. $^1$H NMR (400 MHz, DMSO-$d_6$) δ ppm 8.46 (s, 1H), 7.57 (s, 1H), 7.29 (d, J=8.2 Hz, 2H), 7.05 (d, J=8.7 Hz, 2H), 6.33 (s, 1H), 5.38 (q, J=6.7 Hz, 1H), 3.51-3.04 (m, 10H), 2.83 (s, 3H), 2.27-1.95 (m, 4H), 1.53 (d, J=6.6 Hz, 3H), 0.88 (m, 3H). MS (APCI) m/z 585.2 (M+H)+.

Example 8

N-methyl-1,1-dioxo-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}-1$\lambda^6$-thiane-4-carboxamide

Example 8A (R)-7-(1-methoxyethyl)-2-methylthiazolo[5,4-b]pyridine-6-carboxylic acid Example 1C (20 g, 54.9 mmol), lithium hydroxide-H$_2$O (11.52 g, 274 mmol), tetrahydrofuran (80 mL), and water (40 mL) were stirred at ambient temperature for 24 hours. Upon completion, tetrahydrofuran was removed under reduced pressure and mixture was filtered and the filter cake washed with water. The aqueous filtrate was acidified to pH 1 with concentrated HCl (37% by weight). The mixture was filtered, and the filter cake washed with water, and dried in under vacuum at 60° C. for 24 hours. The aqueous filtrate was concentrated under reduced pressure and triturated with water. The mixture was filtered, and the filter cake dried in under vacuum at 60° C. for 24 hours. After drying the combined filter cakes afforded the title compound. $^1$H NMR (500 MHz, DMSO-$d_6$) δ ppm 13.36 (s, 1H), 8.62 (s, 1H), 5.31 (q, J=6.7 Hz, 1H), 3.13 (s, 3H), 2.88 (s, 3H), 1.62 (d, J=6.6 Hz, 3H). MS (ESI) m/z 253.4 (M+H)$^+$.

Example 8B (R)-7-(1-methoxyethyl)-2-methylthiazolo[5,4-b] pyridin-6-amine

Example 8A (11.6 g, 46.2 mmol), tert-butanol (300 mL), N,N-diisopropylethylamine (40 mL, 231 mmol), and diphenyl phosphorazidate (11.9 mL, 55.4 mmol) were heated at 90° C. for 90 minutes. Upon completion the reaction mixture was concentrated. The residue was dissolved in ethyl acetate, washed with brine, dried over magnesium sulfate, filtered, and concentrated. The residue was purified on silica gel (0-40% ethyl acetate/heptanes) to afford the boc-protected aniline. The boc-protected aniline was dissolved in a 1:1 mixture of trifluoroacetic acid and CH$_2$Cl$_2$ and stirred at ambient temperature for 1 hour. Upon completion, the solution was concentrated. The residue was dissolved in ethyl acetate, washed with saturated aqueous sodium bicarbonate, dried with anhydrous magnesium sulfate, filtered, and concentrated. The residue was purified on silica gel (0-80% ethyl acetate/heptanes) to afford the title compound. $^1$H NMR (600 MHz, DMSO-d$_6$) δ ppm 8.04 (s, 1H), 5.40 (s, 2H), 5.37 (q, J=6.7 Hz, 1H), 3.22 (s, 3H), 2.75 (s, 3H), 1.46 (d, J=6.7 Hz, 3H). MS (ESI) m/z 224.4 (M+H)$^+$.

Example 8C

N-methyl-1,1-dioxo-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}-1λ$^6$-thiane-4-carboxamide Example 8B (5.65 g, 3.86 mmol), Example 1I (12.5 g, 29.1 mmol), and cesium carbonate (24.8 g, 11.6 mmol) in 1,4-dioxane (507 mL) were sparged with N$_2$ for 5 minutes. XPhos Pd G4 (3.27 g, 3.80 mmol) was added, and the reaction mixture was heated at 95° C. for 16 hours. The solution was cooled to 50° C. Pyrrolidine-1-carbodithioic acid, ammonia salt (2.08 g, 12.7 mmol), and water (5 mL) were added to the reaction mixture. The solution was stirred at ambient temperature for 1 hour. The reaction mixture was filtered through diatomaceous earth, and the filter pad washed with ethyl acetate. The filtrate was concentrated. The residue was purified on silica gel (0-100% ethyl acetate/heptanes). This residue was further purified by reverse phase chromatography (C18 HPLC, eluting with 20-100% acetonitrile in water/0.1% trifluoroacetic acid) to isolate the title compound. Clean fractions were combined and concentrated. The aqueous solution was partitioned with ethyl acetate and neutralized with saturated aqueous sodium bicarbonate to free base the desired product. To improve the diastereomeric purity to >99%, the material was subjected to chiral SFC (supercritical fluid chromatography) using a CHIRALPAK® OJ-H column (30×250 mm, 5 micron), eluting with 20% methanol in CO$_2$ at 35° C., 150 mL/minute, 120 bar, to afford the title compound. $^1$H NMR (500 MHz, DMSO-d$_6$) δ ppm 8.51 (s, 1H), 7.73 (d, J=15.3 Hz, 1H), 7.22 (d, J=8.3 Hz, 2H), 7.10-7.02 (m, 2H), 6.45 (q, J=9.3 Hz, 1H), 5.33 (q, J=6.7 Hz, 1H), 3.24 (dd, J=13.3, 3.5 Hz, 1H), 3.21 (s, 3H), 3.21-3.15 (m, 1H), 3.17-3.07 (m, 2H), 2.92 (s, 3H), 2.84 (s, 3H), 2.14-1.95 (m, 5H), 1.52 (d, J=6.7 Hz, 3H). MS (ESI+) m/z 571.7 (M+H)$^+$.

Example 9

N-{(1S)-1-[3,5-difluoro-4-({7-[(1S)-1-methoxyethyl]-2-methyl[1,3]thiazolo[5,4-b]pyridin-6-yl}amino)phenyl]-2,2,2-trifluoroethyl}-N-methyl-1,1-dioxo-1λ$^6$-thiane-4-carboxamide Example 9A (R,E)-N-(4-bromo-3,5-difluorobenzylidene)-2-methylpropane-2-sulfinamide To a mixture of (R)-2-methylpropane-2-sulfinamide (16.4 g, 136 mmol) and 4-bromo-3,5-difluorobenzaldehyde (10 g, 45.2 mmol) in dichloroethane (200 mL) was added copper (II) sulfate (21.7 g, 136 mmol) under N$_2$ at 20° C. The mixture was stirred at 85° C. for 12 hours. The mixture was filtered through a pad of diatomaceous earth. The filtrate was purified by column chromatography on silica gel (10:1-about 5:1 petroleum ether:ethyl acetate) to afford the title compound. $^1$H NMR (400 MHz, CDCl$_3$) δ ppm 8.49 (s, 1H), 7.45 (d, J=6.5 Hz, 2H), 1.28 (s, 9H). LCMS m/z 324.0 (M+H)$^+$.

Example 9B (R)—N—((S)-1-(4-bromo-3,5-difluorophenyl)-2,2,2-trifluoroethyl)-2-methylpropane-2-sulfinamide To a mixture of tetrabutylammonium acetate (4.65 g, 15.4 mmol) and Example 9A (5 g, 15.4 mmol) in NN-dimethyl formamide (100 mL) was added (trifluoromethyl)trimethylsilane (4.93 mL, 30.8 mmol) at −55° C. under N$_2$. The mixture was stirred at −20° C. for 0.5 hours. The reaction was quenched with NH$_4$Cl solution at −40° C. and extracted with ethyl acetate (3×100 mL). The combined organic layers were washed with brine (2×50 mL), dried over Na$_2$SO$_4$, and filtered. The filtrate was concentrated under reduced pressure to afford a residue, which was purified by column chromatography on silica gel (10:1-3:1 petroleum ether/ethyl acetate) to afford the title compound. $^1$H NMR (400 MHz, CDCl$_3$) δ ppm 7.09 (d, J=6.8 Hz, 2H), 4.81 (t, J=7.2 Hz, 1H), 3.65 (br d, J=7.3 Hz, 1H), 1.27 (s, 9H). LCMS m/z 394.0 (M+H)$^+$.

Example 9C (S)-1-(4-bromo-3,5-difluorophenyl)-2,2,2-trifluoroethan-1-amine

To a solution of Example 9B (7.5 g, 19.0 mmol) in ethyl acetate (10 mL) was added a solution of 4 N HCl in ethyl acetate (100 mL). The mixture was stirred at 25° C. for 12 hours. The mixture was concentrated under reduced pressure to afford a residue, which was diluted with methyl tert-butyl ether. The mixture was stirred at 20° C. for 2 hours, and then filtered to afford (S)-1-(4-bromo-3,5-difluorophenyl) 2,2,2-trifluoroethanamine, hydrochloride. The hydrochloride was dissolved in water (20 mL), neutralized with NaHCO$_3$ solution (50 mL) and extracted with dichloromethane (3×100 mL). The combined organic layers were washed with brine (30 mL), dried over Na$_2$SO$_4$, filtered, and the filtrate was concentrated under reduced pressure to afford (S)-1-(4-bromo-3,5-difluorophenyl)-2,2,2-trifluoro ethanamine (5.2 g, 92%), which was used in the next step directly without further purification. $^1$H NMR (400 MHz, CDCl$_3$) δ ppm 7.16-7.05 (m, 2H), 4.41 (q, J=7.0 Hz, 1H), 1.78 (br d, J=2.2 Hz, 2H). LCMS m/z 290.0 (M+H)$^+$.

Example 9D (S)-1-(4-bromo-3,5-difluorophenyl)-2,2,2-trifluoro-N-methylethan-1-amine To a mixture of Example 9C (2.5 g, 8.62 mmol) in methanol (50 mL) was added formaldehyde (0.839 g, 10.3 mmol) at 20° C., and the resulting mixture stirred at 20° C. for 12 hours. NaBH$_4$CN (1.63 g, 25.9 mmol) was added, and the mixture was stirred at 20° C. for 2 hours. The combined mixture was poured into ice water (50 mL) and extracted with dichloromethane (3×50 mL). The combined organic layers were washed with brine (20 mL), dried over Na$_2$SO$_4$, and filtered. The filtrate was concentrated under reduced pressure. The residue was purified by column chromatography on silica gel (20:1 to 5:1 petroleum ether/ethyl acetate) to afford the title compound. $^1$H NMR (400 MHz, CDCl$_3$) δ ppm 7.08 (d, J=7.1 Hz, 2H), 4.03 (q, J=6.9 Hz, 1H), 2.40 (s, 3H), 1.69 (br s, 1H). LCMS m/z 304.0 (M+H)$^+$.

Example 9E (S)—N-(1-(4-bromo-3,5-difluorophenyl)-2,2,2-trifluoroethyl)-N-methyltetrahydro-2H-thiopyran-4-carboxamide 1,1-dioxide To a solution of Example 9D (1 g, 3.29 mmol) and triethylamine (1.38 mL, 9.87 mmol) in dichloromethane (10 mL) was added tetrahydro-2H-thiopyran-4-carbonyl chloride 1,1-dioxide (1.75 g, 8.88 mmol) at 0° C. The mixture was stirred at 25° C. for 12 hours, poured into ice water (20 mL) and extracted with dichloromethane (3×30 mL). The combined organic layers were washed with brine (10 mL), dried over Na$_2$SO$_4$, and filtered. The filtrate was concentrated under reduced pressure. The residue was purified by column chromatography on silica gel (3:1-about 1:1 petroleum ether/ethyl acetate) to afford the title compound. $^1$H NMR (400 MHz, CDCl$_3$) δ ppm 6.99 (br d, J=7.1 Hz, 2H), 6.61 (q, J=8.6 Hz, 1H), 3.58-3.39 (m, 1H), 3.39-3.24 (m, 1H), 3.08-2.84 (m, 6H), 2.53-2.18 (m, 4H). LCMS m/z 464.0 (M+H)$^+$.

Example 9F

N-{(1S)-1-[3,5-difluoro-4-({7-[(1S)-1-methoxyethyl]-2-methyl[1,3]thiazolo[5,4-b]pyridin-6-yl}amino)phenyl]-2,2,2-trifluoroethyl}-N-methyl-1,1-dioxo-1λ$^6$-thiane-4-carboxamide To a solution of Example 9E (200 mg, 0.431 mmol), Example 1F (106 mg, 0.474 mmol) and Cs$_2$CO$_3$ (421 mg, 1.29 mmol) in 1,4-dioxane (4 mL) was added methanesulfonato(2-dicyclohexylphosphino-2,4,6-tri-i-propyl-1,1-biphenyl)(2-methylamino-1,1-biphenyl-2-yl)palladium(II) (111 mg, 0.129 mmol) under N$_2$. The reaction was stirred at 90° C. for 3 hours and filtered. The filtrate was concentrated under reduced pressure to afford a residue, which was purified by preparative HPLC (instrument: Shimadzu LC-8A preparative HPLC; Column: 150×40 mm×10 μm, Waters™ Xbridge Prep OBD C18, 40-70% in 10 minutes acetonitrile/10 mM NH$_4$HCO$_3$ in water) to afford the title compound. $^1$H NMR (400 MHz, CDCl$_3$) δ ppm 7.96 (t, J=2.6 Hz, 1H), 7.58 (s, 1H), 7.02 (br d, J=8.6 Hz, 2H), 6.63 (q, J=8.6 Hz, 1H), 5.62 (q, J=6.7 Hz, 1H), 3.56-3.48 (m, 1H), 3.45 (s, 3H), 3.33 (ddd, J=3.5, 7.4, 10.8 Hz, 1H), 3.10-2.90 (m, 6H), 2.84 (s, 3H), 2.54-2.25 (m, 4H), 1.66 (d, J=6.8 Hz, 3H). LCMS m/z 607.1 (M+H)$^+$.

Example 10

N-methyl-1,1-dioxo-N-{(1S)-2,2,2-trifluoro-1-[3-fluoro-4-({7-[(1S)-1-methoxyethyl]-2-methyl[1,3]thiazolo[5,4-b]pyridin-6-yl}amino)phenyl]ethyl}-1λ$^6$-thiane-4-carboxamide Example 10A 1-(4-bromo-3-fluorophenyl)-2,2,2-trifluoroethanol To a solution of 4-bromo-3-fluorobenzaldehyde (5 g) and cesium fluoride (0.075 g) in tetrahydrofuran (50 mL) at 0° C. was added trimethyl(trifluoromethyl)silane (14.59 mL). The reaction mixture was slowly warmed to ambient temperature and stirred over the weekend. 1 M Aqueous HCl (30 mL) was added, and the mixture was stirred at ambient temperature for 1 hour. Water (50 mL) and ethyl acetate (50 mL) were added, and the layers were separated. The aqueous layer was extracted with ethyl acetate (3×80 mL). The combined organic extracts were dried over magnesium sulfate and filtered. The filtrate was concentrated in vacuo. The crude product was purified by chromatography on silica gel (0-40% ethyl acetate/2-methylpentane) to afford the title compound. $^1$H NMR (400 MHz, DMSO-d$_6$) δ ppm 7.77 (dd, 1H), 7.47 (dd, 1H), 7.31 (dt, 1H), 7.08 (d, 1H), 5.32-5.19 (m, 1H).

Example 10B 1-(4-bromo-3-fluorophenyl)-2,2,2-trifluoro-N-methylethanamine

To a solution of Example 10A (1.3 g) in dichloromethane (30 mL) at −30° C. was added 2,6-dimethylpyridine (1.109 mL) and trifluoromethanesulfonic anhydride (1 M in dichloromethane, 7.14 mL). The reaction mixture was stirred for 2.5 hours, slowly warming to ambient temperature. Methanamine (33 weight % in ethanol, 15 mL) was added, and the reaction mixture was stirred at 45° C. for 4 hours. The reaction mixture was left to stand at ambient temperature overnight. Saturated aqueous sodium hydrogen carbonate (20 mL) was added, and the layers were separated. The aqueous layer was extracted with dichloromethane (2×10 mL). The combined organic extracts were dried over magnesium sulfate and filtered. The filtrate was concentrated in vacuo. The crude product was purified by chromatography on silica gel (0-50% ethyl acetate/2-methylpentane) to afford the title compound. $^1$H NMR (400 MHz, DMSO-d$_6$) δ ppm 7.77 (dd, 1H), 7.53 (dd, 1H), 7.30 (dd, 1H), 4.39 (p, 1H), 2.97 (dq, 1H), 2.20 (d, 3H). MS (ESI) m/z 286.0/288.0 (M+H)$^+$.

Example 10C

N-(1-(4-bromo-3-fluorophenyl)-2,2,2-trifluoroethyl)-N-methyltetrahydro-2H-thiopyran-4-carboxamide 1,1-dioxide To a solution of tetrahydro-2H-thiopyran-4-carboxylic acid 1,1-dioxide (530 mg) in dichloromethane (25 mL) was added 4-methylmorpholine (0.359 mL) and 2,4-dichloro-6-methoxy-1,3,5-triazine (588 mg). The reaction mixture was stirred for 90 minutes at ambient temperature. A solution of Example 10B (850 mg) in dichloromethane (1.5 mL) was added, and the reaction mixture was stirred for 3 days at ambient temperature. The reaction mixture was concentrated in vacuo onto silica gel. The crude product was purified by chromatography on silica gel (0-70% ethyl acetate/2-methylpentane) to afford the title compound. $^1$H NMR (400 MHz, DMSO-$d_6$) δ ppm 7.86-7.77 (m, 1H), 7.35 (dd, 1H), 7.18 (dd, 1H), 6.56 (q, 1H), 3.17 (dddd, 5H), 2.92 (s, 3H), 2.14-1.89 (m, 4H). MS (ESI) m/z 447.8 (weak ionization) (M+H)$^+$.

Example 10D

N-methyl-1,1-dioxo-N-{(1S)-2,2,2-trifluoro-1-[3-fluoro-4-({7-[(1S)-1-methoxyethyl]-2-methyl[1,3]thiazolo[5,4-b]pyridin-6-yl}amino)phenyl]ethyl}-1λ$^6$-thiane-4-carboxamide To a degassed suspension of Example 1F (125 mg), Example 10C (250 mg) and cesium carbonate (548 mg) in 1,4-dioxane (5 mL) at ambient temperature was added XPhos Pd G4 (145 mg), and the reaction mixture was stirred at 90° C. for 3 hours. The reaction mixture was filtered through diatomaceous earth, washing with dichloromethane (10 mL). To the filtrate was added water (5 mL) and saturated aqueous ammonium chloride (5 mL) and the layers were separated. The aqueous layer was extracted with dichloromethane (3×10 mL). The combined organic extracts were washed with brine (10 mL), dried over magnesium sulfate, and filtered. The filtrate was concentrated in vacuo. The residue was purified by chromatography on silica gel (0-100% ethyl acetate-ethanol (3:1)/2-methylpentane, then 0-80% ethyl acetate-ethanol (3:1)/2-methylpentane) to afford the product as a mixture of diastereomers. The mixture of diastereomers was separated by chiral SFC (supercritical fluid chromatography) using a CHIRALPAK® IC column (10×250 mm, 5 micron), eluting with 40% methanol (0.1% ammonia) in CO$_2$ at 40° C., 15 mL/minute, 120 bar, to afford the title compounds as individual diastereomers. The absolute stereochemistry of these title compounds was arbitrarily assigned. $^1$H NMR (400 MHz, DMSO-$d_6$) δ ppm 8.50 (s, 1H), 7.76 (d, 1H), 7.28 (t, 1H), 7.23 (d, 1H), 7.10 (d, 1H), 6.49 (q, 1H), 5.39 (q, 1H), 3.26 (s, 3H), 3.24-3.06 (m, 4H), 2.93 (s, 3H), 2.84 (s, 3H), 2.14-1.88 (m, 5H), 1.51 (d, 3H). MS (ESI) m/z 589.3 (M+H)$^+$.

Example 11

N-methyl-1,1-dioxo-N-{(1S)-2,2,2-trifluoro-1-[4-({2-methyl-7-[(1S)-2,2,2-trifluoro-1-methoxyethyl][1,3]thiazolo[5,4-b]pyridin-6-yl}amino)phenyl]ethyl}-1λ$^6$-thiane-4-carboxamide Example 11A ethyl 2-methyl-7-vinylthiazolo[5,4-b]pyridine-6-carboxylate Ethyl-7-chloro-2-methylthiazolo[5,4-b]pyridine-6-carboxylate (30 g, 117 mmol, WO2018020474A1, Example 16), 4,4,5,5-tetramethyl-2-vinyl-1,3,2-dioxaborolane (27 g, 175 mmol), and Na$_2$CO$_3$ (24.8 g, 234 mmol) were dissolved in mixture of 1,4-dioxane (300 mL) and water (30 mL). The solution was purged with nitrogen and tetrakis(triphenylphosphine)palladium (6.75 g, 5.84 mmol) was added. The resulting solution was heated at 110° C. for 16 hours under a nitrogen atmosphere. After cooling to ambient temperature, 1,4-dioxane was removed under reduced pressure. The resulting mixture was diluted with ethyl acetate (300 mL) and washed with water (2×300 mL). The organic layer was dried with anhydrous sodium sulfate, filtered, and concentrated. The residue was purified on silica gel (10% ethyl acetate/petroleum ether) to afford the title compound. $^1$H NMR (300 MHz, CD$_3$OD) δ ppm 1.44 (t, J=7.1 Hz, 3H), 2.89 (s, 3H), 4.44 (q, J=7.1 Hz, 2H), 5.94 (dd, J=11.7, 1.8 Hz, 1H), 6.70 (dd, J=17.6, 1.8 Hz, 1H), 7.47 (dd, J=17.6, 11.7 Hz, 1H), 8.87 (s, 1H). MS (ESI+) m/z 249 (M+H)$^+$.

Example 11B 2-methyl-7-vinylthiazolo[5,4-b]pyridine-6-carboxylic acid

Example 11A (18.5 g, 74.5 mmol) and lithium hydroxide (3.57 g, 149 mmol) were dissolved in a mixture of 1,4-dioxane (180 mL) and water (100 mL). The reaction mixture was stirred at ambient temperature for 2 hours. Upon complete hydrolysis, 1,4-dioxane was removed under reduced pressure. The resulting aqueous solution was adjusted to pH 2 with 1 M aqueous HCl. The mixture was filtered, and the filter cake dried in vacuo to afford the title compound (15 g, 91%). $^1$H NMR (300 MHz, DMSO-$d_6$) δ ppm 2.89 (s, 3H), 5.96 (dd, J=11.7, 2.1 Hz, 1H), 6.75 (dd, J=17.6, 2.1 Hz, 1H), 7.46 (dd, J=17.6, 11.7 Hz, 1H), 8.88 (s, 1H), 13.61 (s, 1H).

Example 11C tert-butyl (2-methyl-7-vinylthiazolo[5,4-b]pyridin-6-yl)carbamate

Example 11B (15 g, 68 mmol) and triethylamine (19 mL, 136 mmol) were dissolved in tert-butanol (300 mL) and treated with diphenylphosphoryl azide (28.1 g, 102 mmol). The reaction mixture was stirred at ambient temperature for 10 minutes and then refluxed at 95° C. overnight. Upon cooling, the resulting solution was concentrated under reduced pressure. The residue was purified on silica gel (10% ethyl acetate/petroleum ether) to afford the title compound. $^1$H NMR (300 MHz, CDCl$_3$) δ ppm 2.85 (s, 3H), 5.95 (dd, J=11.7, 1.6 Hz, 1H), 6.37-6.49 (m, 1H), 6.62 (s, 1H), 7.03 (dd, J=17.9, 11.7 Hz, 1H), 8.92 (s, 1H). MS (ESI+) m/z 292 (M+H)$^+$.

Example 11D tert-butyl (7-formyl-2-methylthiazolo[5,4-b]pyridin-6-yl)carbamate

Example 11C (15 g, 51.5 mmol), potassium osmate(VI) dihydrate (1.90 g, 5.15 mmol), and sodium periodate (33 g, 154 mmol) were dissolved in an acetonitrile (150 mL), water (150 mL), and tetrahydrofuran (150 mL) mixture. The resulting solution was stirred at ambient temperature for 16 hours. The reaction mixture was quenched with water (20 mL) and extracted with ethyl acetate (3×20 mL). The organic layers were dried with anhydrous sodium sulfate, filtered, and the filtrate was concentrated. The residue was purified on silica gel (20% ethyl acetate/petroleum ether) to afford the title compound. $^1$H NMR (300 MHz, CDCl$_3$) δ ppm 1.59 (s, 9H), 2.92 (s, 3H), 9.82 (s, 1H), 10.34 (s, 1H), 11.10 (d, J=0.8 Hz, 1H). MS (ESI+) m/z 294 (M+H)$^+$.

Example 11E tert-butyl (2-methyl-7-(2,2,2-trifluoro-1-hydroxyethyl)thiazolo[5,4-b]pyridin-6-yl)carbamate A mixture of Example 11D (26 g, 89 mmol), 4 Å molecular sieves (10 g), and dimethyl sulfoxide (250 mL) were treated with (trifluoromethyl)trimethylsilane (15.1 g, 106 mmol). The resulting mixture was stirred at ambient temperature under nitrogen atmosphere for 12 hours. Potassium carbonate (12.3 g, 89 mmol) and dichloromethane (250 mL) were added, and the combined solution was stirred at ambient temperature. After 2 hours, the mixture was filtered, and the filtrate was diluted with water (1.2 L). The aqueous layer was extracted with dichloromethane (3×800 mL). The organic layers were dried with anhydrous sodium sulfate, filtered, and the filtrate was concentrated under reduced pressure. The residue was purified on silica gel (20% ethyl acetate/petroleum ether) to afford the title compound. $^1$H NMR (300 MHz, DMSO-$d_6$) δ ppm 1.47 (s, 9H), 2.85 (s, 3H), 6.08-6.25 (m, 1H), 8.29 (d, J=6.2 Hz, 1H), 8.62 (s, 1H), 9.07 (s, 1H).

Example 11F tert-butyl (2-methyl-7-(2,2,2-trifluoro-1-methoxyethyl)thiazolo[5,4-b]pyridin-6-yl)carbamate Potassium carbonate (12.3 g, 89 mmol) and methyl iodide (5.6 mL, 89 mmol) were added to a solution of Example 11E (29.4 g, 81 mmol) in NN-dimethyl formamide (500 mL). The resulting heterogeneous mixture was stirred at ambient temperature for 12 hours, and then diluted with water (1000 mL). The layers were separated, and the aqueous layer was extracted with ethyl acetate (3×300 mL). The combined organic layers were washed with brine (300 mL), dried with anhydrous sodium sulfate, filtered, and the filtrate concentrated under reduced pressure. The residue was purified on silica gel (0-100% ethyl acetate/petroleum ether) to afford the title compound. $^1$H NMR (400 MHz, DMSO-$d_6$) δ ppm 1.47 (s, 9H), 2.87 (s, 3H), 3.54 (s, 3H), 5.98 (q, J=7.6 Hz, 1H), 8.28 (s, 1H), 8.97 (s, 1H). MS (ESI+) m/z 378 (M+H)$^+$.

Example 11G (R)-2-methyl-7-(2,2,2-trifluoro-1-methoxyethyl)thiazolo[5,4-b]pyridin-6-amine; and

Example 11H (S)-2-methyl-7-(2,2,2-trifluoro-1-methoxyethyl)thiazolo[5,4-b]pyridin-6-amine Example 11F (35.2 g, 93.3 mmol) was dissolved in 4 M HCl in ethyl acetate (200 mL, 800 mmol) and stirred at ambient temperature for 2 hours. After complete consumption of starting material as determined by LCMS, the reaction mixture was filtered, and the filter cake was washed with ethyl acetate (80 mL). The filter cake was dispersed in water (80 mL), and the resulting suspension was adjusted to pH 9 with 15% aqueous sodium carbonate and filtered. The filter cake was washed with water (80 mL) and dried under vacuum to afford a 1:1 mixture of Example 11G and 11H. The racemic material was subjected to chiral SFC (supercritical fluid chromatography) using a CHIRALPAK® AD-H column (5×25 cm, 5 micron), eluting with 15% methanol (2 mM ammonia) in CO$_2$ at 35° C., 150 mL/minute, to afford the title compounds (Example 11G: retention time 5.14 minutes and Example 11H: retention time 5.95 min). Example 11G: $^1$H NMR (300 MHz, DMSO-$d_6$) δ ppm 2.77 (s, 3H), 3.44 (s, 3H), 5.64 (s, 2H), 5.83 (q, J=7.8 Hz, 1H), 8.12 (s, 1H). MS (ESI+) m/z 278 (M+H)$^+$. Example 11H: $^1$H NMR (300 MHz, DMSO-$d_6$) δ ppm 2.77 (s, 3H), 3.44 (s, 3H), 5.64 (s, 2H), 5.83 (q, J=7.8 Hz, 1H), 8.12 (s, 1H). MS (ESI+) m/z 278 (M+H)$^+$.

Example 11I

N-methyl-1,1-dioxo-N-{(1S)-2,2,2-trifluoro-1-[4-({2-methyl-7-[(1S)-2,2,2-trifluoro-1-methoxyethyl][1,3]thiazolo[5,4-b]pyridin-6-yl}amino)phenyl]ethyl}-1λ$^6$-thiane-4-carboxamide Example 11H (0.15 g, 0.54 mmol), Example 1I (0.24 g, 0.57 mmol), and cesium carbonate (0.53 g, 1.6 mmol) in 1,4-dioxane (10 mL) were sparged with N$_2$ for 2 minutes. XPhos Pd G4 (70 mg, 0.081 mmol) was added, and the reaction mixture was heated 95° C. for 16 hours. The solution was cooled to ambient temperature, filtered through diatomaceous earth, and the diatomaceous earth pad was washed with ethyl acetate. The filtrate was concentrated, and the residue was purified by reverse phase chromatography (C18 HPLC, eluting with 20-100% acetonitrile in water/ 0.1% trifluoroacetic acid) to isolate the title compound. Clean fractions were combined and concentrated to remove acetonitrile. The aqueous solution was partitioned with ethyl acetate and neutralized with saturated aqueous sodium bicarbonate to free base the desired product. The organic layer was dried over anhydrous magnesium sulfate, filtered, and concentrated. The residue was lyophilized to provide the title compound. $^1$H NMR (600 MHz, DMSO-$d_6$) δ ppm 8.60 (s, 1H), 7.62 (d, J=18.2 Hz, 1H), 7.25 (d, J=8.4 Hz, 2H), 7.15 (d, J=8.6 Hz, 2H), 6.46 (q, J=9.2 Hz, 1H), 5.93 (q, J=7.6 Hz, 1H), 3.52 (s, 3H), 3.30-3.07 (m, 5H), 2.92 (s, 3H), 2.86 (s, 3H), 2.19-1.94 (m, 4H). MS (ESI+) m/z 626.0 (M+H)$^+$.

Example 12

N-{(1S)-2,2-difluoro-1-[4-({7-[(1R)-1-methoxyethyl]-2-methyl[1,3]thiazolo[5,4-b]pyridin-6-yl}amino)phenyl]ethyl}-N-methyl-1,1-dioxo-1λ$^6$-thiane-4-carboxamide

Example 12A

N-(4-((S)-2,2-difluoro-1-(methylamino)ethyl)phenyl)-7-((R)-1-methoxyethyl)-2-methylthiazolo[5,4-b]pyridin-6-amine Example 8B (0.500 g, 2.24 mmol), Example 4B (0.588 g, 2.35 mmol), and cesium carbonate (2.19 g, 6.72 mmol) in 1,4-dioxane (25 mL) were sparged with N$_2$ for 2 minutes. XPhos Pd G4 (0.39 g, 0.45 mmol) was added, and the reaction mixture was heated 95° C. for 16 hours. The reaction mixture was cooled, filtered through diatomaceous earth, and the diatomaceous earth pad was washed with ethyl acetate. The filtrate was concentrated, and the residue was purified on silica gel (0-100% ethyl acetate/heptanes) to afford the title compound. $^1$H NMR (400 MHz, DMSO-$d_6$) δ ppm 8.48 (s, 1H), 7.55 (s, 1H), 7.29-7.22 (m, 2H), 7.07-6.99 (m, 2H), 6.00 (d, J=4.3 Hz, 1H), 5.37 (q, J=6.6 Hz, 1H), 3.70 (d, J=13.9 Hz, 1H), 3.24 (s, 3H), 2.83 (s, 3H), 2.34 (s, 1H), 2.19 (d, J=3.2 Hz, 3H), 1.52 (d, J=6.7 Hz, 3H). MS (ESI) m/z 393.2 (M+H)$^+$.

Example 12B

N-{(1S)-2,2-difluoro-1-[4-({7-[(1R)-1-methoxy-ethyl]-2-methyl[1,3]thiazolo[5,4-b]pyridin-6-yl}amino)phenyl]ethyl}-N-methyl-1,1-dioxo-1λ⁶-thiane-4-carboxamide Example 12B was prepared according to the procedure used for the preparation of Example 5B, substituting Example 12A for Example 5A, to provide the title compound. ¹H NMR (600 MHz, DMSO-d₆) δ ppm 8.49 (d, J=2.6 Hz, 1H), 7.62 (s, 1H), 7.29 (d, J=8.5 Hz, 1H), 7.24-7.20 (m, 2H), 7.08-7.01 (m, 2H), 6.73 (dd, J=12.3, 5.3 Hz, OH), 5.80-5.72 (m, 1H), 5.34 (q, J=6.7 Hz, 1H), 3.22 (d, J=2.9 Hz, 4H), 3.13-3.06 (m, 3H), 2.93 (s, 3H), 2.83 (d, J=1.5 Hz, 3H), 2.67 (s, 1H), 2.09-2.00 (m, 3H), 2.02-1.95 (m, 1H), 1.52 (dd, J=6.6, 1.7 Hz, 3H). MS (ESI) m/z 553.6 (M+H)⁺.

Example 13

N-{(1S)-1-[4-({7-[(1S)-2,2-difluoro-1-methoxy-ethyl]-2-methyl[1,3]thiazolo[5,4-b]pyridin-6-yl}amino)phenyl]-2,2-difluoroethyl}-N-methyl-1,1-dioxo-1λ⁶-thiane-4-carboxamide

Example 13A

N-(4-((S)-2,2-difluoro-1-(methylamino)ethyl)phenyl)-7-((S)-2,2-difluoro-1-methoxyethyl)-2-methyl-thiazolo[5,4-b]pyridin-6-amine Example 3H (0.500 g, 2.24 mmol), Example 4B (0.506 g, 2.03 mmol), and cesium carbonate (2.19 g, 6.72 mmol) in 1,4-dioxane (30 mL) were sparged with N₂ for 2 minutes. XPhos Pd G4 (0.17 g, 0.19 mmol) was added, and the reaction mixture was heated 95° C. for 16 hours. The reaction mixture was cooled, filtered through diatomaceous earth, and the diatomaceous earth pad was washed with ethyl acetate. The filtrate was concentrated, and the residue was purified on silica gel (0-100% ethyl acetate/heptanes) to afford the title compound. ¹H NMR (400 MHz, DMSO-d₆) δ ppm 8.49 (s, 1H), 7.77 (s, 1H), 7.39-7.11 (m, 2H), 7.10-6.93 (m, 2H), 6.74 (ddd, J=57.5, 54.5, 5.8 Hz, 1H), 5.99 (td, J=56.3, 4.3 Hz, 1H), 5.36 (dt, J=13.8, 5.9 Hz, 1H), 3.71 (t, J=12.8 Hz, 1H), 3.31 (s, 3H), 2.85 (s, 3H), 2.32 (s, 1H), 2.19 (s, 3H). MS (ESI) m/z 429.8 (M+H)⁺.

Example 13B

N-{(1S)-1-[4-({7-[(1S)-2,2-difluoro-1-methoxy-ethyl]-2-methyl[1,3]thiazolo[5,4-b]pyridin-6-yl}amino)phenyl]-2,2-difluoroethyl}-N-methyl-1,1-dioxo-1λ⁶-thiane-4-carboxamide Example 13B was prepared according to the procedure used for the preparation of Example 5B, substituting Example 13A for Example 5A, to provide the title compound. ¹H NMR (600 MHz, DMSO-d₆) δ ppm 8.51 (d, J=3.3 Hz, 1H), 7.88 (s, 1H), 7.22-7.16 (m, 2H), 7.00-6.91 (m, 2H), 6.87-6.56 (m, 2H), 5.75 (td, J=13.3, 5.3 Hz, 1H), 5.33 (dt, J=14.0, 5.5 Hz, 1H), 3.29 (d, J=2.3 Hz, 3H), 3.27-3.04 (m, 5H), 2.93 (s, 3H), 2.86 (s, J=1.9 Hz, 3H), 2.16-1.87 (m, 4H). MS (ESI) m/z 589.5 (M+H)⁺.

Example 14

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-N-methyl-1,1-dioxo-1λ⁶-thiane-4-carboxamide

Example 14A

N-(4-((S)-2,2-difluoro-1-(methylamino)ethyl)phenyl)-2-methyl-7-((R)-2,2,2-trifluoro-1-methoxyethyl)thiazolo[5,4-b]pyridin-6-amine Example 14A (345.2 mg, 97%) was prepared using the conditions described in Example 4C substituting Example 11G for Example 1F. MS (APCI) m/z 447.3 (M+H)⁺.

Example 14B

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-N-methyl-1,1-dioxo-1λ⁶-thiane-4-carboxamide Example 14B (75.4 mg, 51%) was prepared using the conditions described in Example 4D substituting Example 14A for Example 4C. ¹H NMR (400 MHz, DMSO-d₆) δ ppm 8.53 (s, 1H), 7.37 (s, 1H), 7.29 (d, J=8.3 Hz, 2H), 7.12 (d, J=8.7 Hz, 2H), 6.88-6.46 (m, 1H), 5.94 (q, J=7.7 Hz, 1H), 5.72 (s, 1H), 3.56 (s, 3H), 3.28-3.04 (m, 5H), 2.94 (s, 3H), 2.85 (s, 3H), 2.20-1.98 (m, 4H). MS (APCI) m/z 607.3 (M+H)⁺.

Example 15

N-{(1S)-1-[4-({2-(difluoromethyl)-7-[(1S)-1-methoxyethyl][1,3]thiazolo[5,4-b]pyridin-6-yl}amino)phenyl]-2,2,2-trifluoroethyl}-N-methyl-1,1-dioxo-1λ⁶-thiane-4-carboxamide

Example 15A methyl (S)-7-(1-methoxyethyl)-2-methylthiazolo[5,4-b]pyridine-6-carboxylate To a solution of Example 1D (1 g, 3.96 mmol) in N,N-dimethylformamide (12 mL) was added potassium carbonate (1.096 g, 7.93 mmol), and iodomethane (0.296 mL, 4.76 mmol). The resulting suspension was stirred at ambient temperature for 2 hours. The reaction mixture was partitioned between water (40 mL) and ethyl acetate (30 mL). The layers were separated, and the aqueous layer extracted with ethyl acetate (2×30 mL). The combined organic extracts were washed with water (30 mL) and saturated sodium chloride solution (30 mL), dried over anhydrous magnesium sulfate, and filtered. The filtrate was concentrated in vacuo. The crude product was purified by chromatography on the Companion (24 g column, 10-50% ethyl acetate/2-methylpentane) to afford the title compound (980 mg, 3.68 mmol, 93%). ¹H NMR (400 MHz, DMSO-d₆) δ ppm 8.61 (s, 1H), 5.25 (q, J=6.7 Hz, 1H), 3.86 (s, 3H), 3.14 (s, 3H), 2.89 (s, 3H), 1.59 (d, J=6.6 Hz, 3H). MS (ESI) m/z 267.1 (M+H)⁺.

Example 15B methyl (S)-2-formyl-7-(1-methoxyethyl)thiazolo[5,4-b]pyridine-6-carboxylate A mixture of Example 15A (15 g, 56.3 mmol) and selenium dioxide (25.00 g, 225 mmol) in 1,4-dioxane (210 mL) was stirred at 93° C. for 8 hours. After cooling, the reaction mixture was filtrated, concentrated under reduced pressure, and the residue was purified by column chromatography on silica gel eluting with ethyl acetate/petroleum (1:4) to afford the title compound (2.808 g, 9.66 mmol, 17.15%). $^1$H NMR (300 MHz, DMSO-$d_6$) δ ppm 10.13 (s, 1H), 8.90 (s, 1H), 5.30-5.43 (m, 1H), 3.90 (s, 3H), 3.18 (s, 3H), 1.65 (d, J=6.7 Hz, 3H). LCMS (ESI) m/z 281 (M+H)$^+$.

Example 15C methyl (S)-2-(difluoromethyl)-7-(1-methoxyethyl)thiazolo[5,4-b]pyridine-6-carboxylate To a solution of Example 15B (1.2 g, 4.28 mmol) in toluene (36 mL) was added [bis(2-methoxyethyl)amino]sulfur trifluoride (5.21 g, 23.55 mmol) at 0° C. The reaction mixture was stirred at 50° C. overnight. After cooling, the reaction mixture was partitioned between saturated aqueous sodium bicarbonate (50 mL) and dichloromethane (3×100 mL). The combined organic layers were washed with sodium bicarbonate solution (50 mL), dried over anhydrous sodium sulfate, filtered and the filtrate was concentrated. The residue was purified by Preparative TLC with ethyl acetate/petroleum ether (1/1) to afford the title compound (812.4 mg, 2.63 mmol, 61.5%). $^1$H NMR (400 MHz, DMSO-$d_6$) δ ppm 8.83 (d, J=1.4 Hz, 1H), 5.27 (q, J=6.6 Hz, 1H), 3.86 (s, 3H), 3.13 (s, 3H), 1.58 (d, J=6.7 Hz, 3H). MS (ESI) m/z 303 (M+H)$^+$.

Example 15D (S)-2-(difluoromethyl)-7-(1-methoxyethyl)thiazolo[5,4-b]pyridine-6-carboxylic acid A mixture of Example 15C (0.3 g, 0.992 mmol) and sodium carbonate (0.526 g, 4.96 mmol) in methanol (10 mL) was stirred at ambient temperature overnight. The solvent was removed, and the residue was redissolved in ethyl acetate and 0.1 N aqueous HCl. The aqueous layer was extracted with additional ethyl acetate twice. The combined organic layers were washed with saturated sodium bicarbonate, dried over anhydrous magnesium sulfate, filtered and concentrated. The residue was purified by reverse phase Prep HPLC on a C18 column eluting with 20-100% acetonitrile in 0.1% trifluoroacetic acid water solution to afford the title compound (0.082 g, 0.284 mmol, 28.7%). Also 0.10 g of Example 15C was recovered. $^1$H NMR (600 MHz, DMSO-$d_6$) δ ppm 13.60 (s, 1H), 8.86 (s, 1H), 7.63-7.45 (m, 1H), 5.35 (q, J=6.6 Hz, 1H), 3.15 (s, 3H), 1.64 (d, J=6.7 Hz, 3H). MS (ESI) m/z 289.0 (M+H)$^+$.

Example 15E

A mixture of Example 15D (0.07 g, 0.243 mmol), diphenyl phosphorazidate (0.080 g, 0.291 mmol), and triethylamine (0.203 mL, 1.457 mmol) in tert-butyl alcohol (3 mL) was heated at 80° C. overnight. The solvent was removed, and the residue was purified by flash column chromatography on silica gel eluting with 50% ethyl acetate in heptanes to afford the title compound (0.017 g, 0.066 mmol, 27.0%). $^1$H NMR (500 MHz, DMSO-$d_6$) δ ppm 8.26 (s, 1H), 7.42 (t, J=53.9 Hz, 1H), 5.67 (s, 2H), 5.37 (q, J=6.7 Hz, 1H), 3.24 (s, 3H), 1.49 (d, J=6.7 Hz, 3H). MS (ESI) m/z 261.0 (M+H)$^+$.

Example 15F

N-{(1S)-1-[4-({2-(difluoromethyl)-7-[(1S)-1-methoxyethyl][1,3]thiazolo[5,4-b]pyridin-6-yl}amino)phenyl]-2,2,2-trifluoroethyl}-N-methyl-1,1-dioxo-1λ$^6$-thiane-4-carboxamide A mixture of Example 15E (0.018 g, 0.070 mmol), Example 1J (0.03 g, 0.070 mmol), and cesium carbonate (0.068 g, 0.210 mmol) in 1,4-dioxane (1.5 mL) was degassed and backfilled with nitrogen several times. To this reaction mixture was added chloro(2-dicyclohexylphosphino-2',4',6'-triisopropyl-1,1'-biphenyl)[2-(2'-amino-1,1'-biphenyl)]palladium(II) (5.51 mg, 7.01 µmol). The reaction vessel was re-capped, then degassed and backfilled with nitrogen several times. The reaction mixture was heated at 95° C. overnight. The reaction mixture was partitioned between water and ethyl acetate, and the aqueous layer extracted with additional ethyl acetate. The combined organic layers were washed with saturated sodium chloride, dried over anhydrous magnesium sulfate, filtered, and the filtrate was concentrated. The residue was purified by reverse phase Prep HPLC on a C18 column, eluting with 20-100% acetonitrile in 0.1% trifluoroacetic acid water solution to afford the title compound (0.031 g, 0.051 mmol, 73.0%). $^1$H NMR (600 MHz, DMSO-$d_6$) δ ppm 8.70 (s, 1H), 7.88 (s, 1H), 7.50 (t, J=53.8 Hz, 1H), 7.24 (d, J=8.4 Hz, 2H), 7.14-7.07 (m, 2H), 6.45 (q, J=9.3 Hz, 1H), 5.32 (q, J=6.7 Hz, 1H), 3.21 (s, 3H), 3.29-3.07 (m, 4H), 2.91 (s, 3H), 2.13-2.07 (m, 1H), 2.05 (dq, J=8.7, 3.3 Hz, 2H), 2.05-1.96 (m, 1H), 1.56 (d, J=6.7 Hz, 3H). MS (ESI) m/z 608.0 (M+H)$^+$.

Example 16

N-[(1S)-1-(4-{[7-(1,1-difluoropropan-2-yl)-2-methyl[1,3]thiazolo[5,4-b]pyridin-6-yl]amino}phenyl)-2,2,2-trifluoroethyl]-N-methyl-1,1-dioxo-1λ$^6$-thiane-4-carboxamide

Example 16A tert-butyl (7-(2,2-difluoro-1-hydroxyethyl)-2-methylthiazolo[5,4-b]pyridin-6-yl)carbamate To a suspension of Example 11D (4 g) in N,N-dimethylformamide (40 mL) was added (bromodifluoromethyl)trimethylsilane (4.24 mL) and triphenylphosphine (7.15 g), and the reaction mixture was stirred at ambient temperature for 16 hours. The reaction mixture was cooled to 0° C. and potassium hydroxide (2 M in water, 13.64 mL) was slowly added. The reaction mixture was stirred at this temperature for 1 hour and then saturated aqueous ammonium chloride (50 mL) was added. Water (50 mL) and ethyl acetate (50 mL) were added, and the layers were separated. The aqueous layer was extracted with ethyl acetate (3×70 mL), and the combined organic extracts were washed with water/brine (1:1, 3×50 mL), dried over magnesium sulfate and filtered. The filtrate was concentrated in vacuo. The residue was purified by chromatography on silica gel (0-60% ethyl acetate/2-methylpentane) to afford the title compound. $^1$H NMR (400 MHz, DMSO-$d_6$) δ ppm 9.00 (s, 1H), 8.88 (s, 1H), 7.35 (d, 1H), 6.40 (td, 1H), 5.82-5.72 (m, 1H), 2.84 (s, 3H), 1.48 (s, 9H). MS (ESI) m/z 345.8 (M+H)$^+$.

Example 16B tert-butyl (7-(2,2-difluoroacetyl)-2-methylthiazolo[5,4-b]pyridin-6-yl)carbamate To a solution of Example 16A (500 mg) in dichloromethane (15 mL) was added 1,1,1-tris(acetyloxy)-1,1-dihydro-1,2-benzodioxol-3-(1H)-one (Dess-Martin periodinane) (921 mg) and sodium hydrogen carbonate (243 mg). The reaction mixture was stirred at ambient temperature for 45 minutes, filtered, and the filter cake was washed with dichloromethane (10 mL). The filtrate was washed with saturated aqueous sodium hydrogen carbonate (10 mL), dried over magnesium sulfate, and filtered. The filtrate was concentrated in vacuo. The residue was purified by chromatography on silica gel (0-40% ethyl acetate/2-methylpentane) to afford the title compound. $^1$H NMR (400 MHz, DMSO-d$_6$) δ ppm 10.18 (s, 1H), 8.51 (s, 1H), 6.82 (t, 1H), 2.85 (s, 3H), 1.45 (s, 9H). MS (ESI) m/z 362.4 (M+H$_3$O)$^+$.

Example 16C tert-butyl (7-(3,3-difluoroprop-1-en-2-yl)-2-methylthiazolo[5,4-b]pyridin-6-yl)carbamate To a suspension of methyltriphenylphosphonium bromide (1270 mg) in tetrahydrofuran (15 mL) at 0° C. was slowly added potassium tert-butoxide (1 M in tetrahydrofuran, 3.23 mL). The reaction was stirred for 40 minutes at this temperature. To a solution of Example 16B (370 mg) in tetrahydrofuran (10 mL) at −10° C. was added, a portion of the pre-formed ylid solution (6 mL), and the reaction mixture was stirred for 30 minutes. Another portion of ylid solution (6 mL) was added, and the reaction mixture was stirred overnight, slowly warming to ambient temperature. The reaction mixture was stirred at 50° C. for 1 hour, then at 70° C. for 12 hours, and was left to stand at ambient temperature for 3 days. Saturated aqueous ammonium chloride (20 mL) was added, and the mixture was extracted with ethyl acetate (3×20 mL). The combined organic extracts were dried over magnesium sulfate and filtered. The filtrate was concentrated in vacuo. The residue was purified by chromatography on silica gel (0-100% ethyl acetate/2-methylpentane) to afford the title compound. $^1$H NMR (400 MHz, DMSO-d$_6$) δ ppm 8.75 (s, 1H), 8.57 (s, 1H), 6.86 (t, 1H), 6.16 (q, 1H), 5.76 (s, 1H), 2.82 (s, 3H), 1.43 (s, 9H). MS (ESI) m/z 342.2 (M+H)$^+$.

Example 16D tert-butyl (7-(3,3-difluoroprop-1-en-2-yl)-2-methylthiazolo[5,4-b]pyridin-6-yl)carbamate To a solution of Example 16C (130 mg) in tetrahydrofuran (3 mL) was added palladium (5 weight % on carbon, 130 mg). The reaction mixture was stirred under atmosphere of hydrogen (3 bar) at ambient temperature for 3 hours. The reaction mixture was filtered through a glass microfiber pad, washing with methanol (5 mL), and the filtrate was concentrated in vacuo. The residue was purified by chromatography on silica gel (0-50% ethyl acetate/2-methylpentane) to afford the title compound. $^1$H NMR (400 MHz, DMSO-d$_6$) δ ppm 9.17 (s, 1H), 8.43 (s, 1H), 6.98-6.61 (m, 1H), 3.72 (dp, 1H), 2.86 (s, 3H), 1.48 (d, 3H), 1.46 (s, 9H). MS (ESI) m/z 344.2 (M+H)$^+$.

Example 16E 7-(1,1-difluoropropan-2-yl)-2-methylthiazolo[5,4-b]pyridin-6-amine

To a solution of Example 16D (1.1 g) in dichloromethane (20 mL) was added 2,2,2-trifluoroacetic acid (4.90 mL). The reaction mixture was stirred at ambient temperature for 3 hours. Toluene (10 mL) was added, and the reaction mixture was concentrated in vacuo. The residue was dissolved in dichloromethane (20 mL) and washed with saturated aqueous sodium hydrogen carbonate (20 mL). The layers were separated, and the aqueous layer was extracted with dichloromethane (2×10 mL). The combined organic extracts were dried over magnesium sulfate and filtered. The filtrate was concentrated in vacuo to afford the title compound. $^1$H NMR (400 MHz, DMSO-d$_6$) δ ppm 8.05 (s, 1H), 6.85 (ddd, 1H), 5.53 (s, 2H), 3.86-3.67 (m, 1H), 2.76 (s, 3H), 1.39 (d, 3H). MS (ESI) m/z 244.2 (M+H)$^+$.

Example 16F

N-[(1S)-1-(4-{[7-(1,1-difluoropropan-2-yl)-2-methyl[1,3]thiazolo[5,4-b]pyridin-6-yl]amino}phenyl)-2,2,2-trifluoroethyl]-N-methyl-1,1-dioxo-1λ$^6$-thiane-4-carboxamide To a degassed suspension of Example 16E (150 mg), Example 1J (396 mg) and potassium phosphate (262 mg) in 1,4-dioxane (5 mL) was added XPhos Pd G4 (106 mg), and the reaction mixture was stirred at 70° C. for 18 hours. After cooling to ambient temperature, the reaction mixture was filtered through diatomaceous earth, washing with dichloromethane (15 mL). The filtrate was concentrated in vacuo, and the residue was purified by chromatography on silica gel (0-80% ethyl acetate/2-methylpentane). The product was dissolved in tetrahydrofuran (5 mL) and pyrrolidine-1-carbodithioic acid, ammonia salt (APDTC) was added. The resulting suspension was stirred at 40° C. for 3 hours and then filtered. The filtrate was concentrated in vacuo onto silica gel and the residue purified by chromatography on silica gel (0-80% ethyl acetate/2-methylpentane) to afford the title compound. $^1$H NMR (400 MHz, DMSO-d$_6$) δ ppm 8.43 (s, 1H), 8.13 (s, 1H), 7.16 (d, 2H), 6.84 (td, 1H), 6.78 (d, 2H), 6.41 (q, 1H), 3.88 (dq, 1H), 3.30-3.06 (m, 5H), 2.90 (s, 3H), 2.87 (s, 3H), 2.11-1.94 (m, 4H), 1.45 (d, 3H). MS (ESI) m/z 591.1 (M+H)$^+$.

Example 17

N-{(1S)-1-[4-({7-[(1R)-2,2-difluoro-1-methoxyethyl]-2-methyl[1,3]thiazolo[5,4-b]pyridin-6-yl}amino)-3-fluorophenyl]-2,2,2-trifluoroethyl}-N-methyl-1,1-dioxo-1λ$^6$-thiane-4-carboxamide To a degassed suspension of Example 3G (116 mg), Example 10C (200 mg) and potassium phosphate (95 mg) in 1,4-dioxane (2 mL) was added XPhos Pd G4 (77 mg), and the reaction mixture was stirred at 70° C. for 16 hours. After cooling to ambient temperature, the reaction mixture was filtered through diatomaceous earth, washing with dichloromethane (10 mL). The filtrate was concentrated in vacuo, and the residue was purified by chromatography on silica gel (0-100% ethyl acetate-ethanol (3:1)/2-methylpentane) to afford the product as a mixture of diastereomers. The mixture of diastereomers was separated by chiral SFC (supercritical fluid chromatography) using a CHIRALPAK® IC column (10×250 mm, 5 micron), eluting with 35% methanol (0.1% ammonia) in $CO_2$ at 40° C., 15 mL/minute, 120 bar, to afford the title compounds as individual diastereomers. The absolute stereochemistry of these title compounds was arbitrarily assigned. $^1$H NMR (400 MHz, DMSO-$d_6$) δ ppm 8.46 (s, 1H), 7.84 (s, 1H), 7.21 (d, 1H), 7.15-7.04 (m, 2H), 6.72 (td, 1H), 6.48 (q, 1H), 5.41 (dt, 1H), 3.34 (s, 3H), 3.28-3.05 (m, 5H), 2.93 (s, 3H), 2.86 (s, 3H), 2.14-1.93 (m, 4H). MS (ESI) m/z 625.1 (M+H)$^+$.

Example 18

1-acetyl-N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methylpiperidine-4-carboxamide Example 18A (S)-1-acetyl-N-(1-(4-bromophenyl)-2,2,2-trifluoroethyl)-N-methylpiperidine-4-carboxamide To a 40 mL vial containing the hydrochloride salt of Example 1I (1.0 g, 3.28 mmol) in dichloromethane (3 mL), pyridine (1.328 mL, 16.42 mmol), and N,N-dimethylpyridin-4-amine (0.401 g, 3.28 mmol) was added 1-acetylpiperidine-4-carbonyl chloride (0.747 g, 3.94 mmol). The reaction stirred at ambient temperature for 30 minutes and diluted with dichloromethane (20 mL). The organic layer was washed with saturated aqueous ammonium chloride solution (20 mL), dried over anhydrous magnesium sulfate, and filtered. The filtrate was concentrated. The residue was purified by automated flash chromatography (ISCO, $SiO_2$, ethyl acetate/hexanes) to afford the title compound.

Example 18B 1-acetyl-N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methylpiperidine-4-carboxamide Example 18A (125 mg, 0.297 mmol), Example 3G (70 mg, 0.270 mmol), Pd-Xphos-G2 (21.24 mg, 0.027 mmol) and $Cs_2CO_3$ (264 mg, 0.810 mmol) were placed in a vial. The contents were evacuated and backfilled with nitrogen twice. 1,4-Dioxane was added, and the mixture stirred at 90° C. under nitrogen overnight. The crude mixture was filtered over diatomaceous earth and concentrated in vacuo. The crude residue was purified using reverse phase chromatography (C18 HPLC, eluting with 20-70% acetonitrile in water/0.1% formic acid) to afford the title compound. $^1$H NMR (500 MHz, CDCl$_3$) 8.61 (s, 1H), 7.26 (t, J=8.5 Hz, 2H), 7.08-7.02 (m, 2H), 6.59 (q, J=9.0 Hz, 1H), 6.12 (td, J=55 Hz, 1H), 5.57 (m, 1H), 4.61 (t, J=12.1 Hz, 1H), 3.91 (d, J=13.2 Hz, 1H), 3.57 (s, 3H), 3.14 (m, 1H), 2.93 (d, J=2.4 Hz, 3H), 2.83 (s, 3H), 2.82-2.67 (m, 3H), 2.11 (s, 3H), 1.92-1.70 (m, 4H). MS (ESI) m/z 600.4 (M+H)$^+$.

Example 19

1-acetyl-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 18A (83 mg, 0.197 mmol), Example 1F (40 mg, 0.179 mmol), Pd-Xphos-G2 (14.09 mg, 0.018 mmol) and $Cs_2CO_3$ (175 mg, 0.537 mmol) were placed in a vial. The contents were evacuated and backfilled with nitrogen twice. 1,4-Dioxane was added, and the mixture stirred at 90° C. under nitrogen overnight. The mixture was filtered over diatomaceous earth and concentrated in vacuo. The residue was purified using automated flash chromatography (ISCO, $SiO_2$, ethyl acetate/hexanes) to afford the title compound. $^1$H NMR (500 MHz, CDCl$_3$) 8.60 (s, 1H), 7.46 (s, 1H), 7.26 (t, J=7.4 Hz, 2H), 7.16-7.05 (m, 2H), 6.59 (q, J=9.0 Hz, 1H), 5.57 (q, J=6.7 Hz, 1H), 4.61 (t, J=12.1 Hz, 1H), 3.91 (d, J=13.2 Hz, 1H), 3.41 (s, 3H), 3.14 (ddd, J=17.2, 9.8, 4.4 Hz, 1H), 2.94 (d, J=2.4 Hz, 3H), 2.83 (s, 3H), 2.82 (s, 1H), 2.81-2.68 (m, 1H), 2.11 (s, 3H), 1.92-1.70 (m, 3H), 1.56 (d, J=6.7 Hz, 3H). MS (ESI) m/z 564.0 (M+H)$^+$.

Example 20

1-(hydroxyacetyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 20A (S)-tert-butyl 4-((1-(4-bromophenyl)-2,2,2-trifluoroethyl)(methyl)carbamoyl)piperidine-1-carboxylate To a mixture of 1-(tert-butoxycarbonyl)piperidine-4-carboxylic acid (459 mg, 2.00 mmol) in dichloromethane (10 mL) was added 2.0 M oxalyl chloride in dichloromethane (2.00 mL, 4.00 mmol) at 0° C., followed by the addition of trace of N,N-dimethylformamide. The reaction mixture was stirred at 5° C. for 3 hours, concentrated, and azeotroped with toluene twice. The residue was dissolved in dichloromethane (5.0 mL), added slowly to the mixture of the hydrochloric acid salt of Example 1I (305 mg, 1.00 mmol) and N,N-diisopropylethylamine (0.875 mL, 5.01 mmol) in dichloromethane (5.0 mL) at 0° C. The reaction mixture was stirred at 5° C. for 1 hour, and partitioned with dichloromethane and water. The organic layer was washed with 5% aqueous sodium bicarbonate and saturated aqueous sodium chloride, dried with anhydrous sodium sulfate, filtered, and concentrated. The residue was purified by flash chromatography (silica gel, 10-50% 3:1 ethyl acetate/ethanol in heptane) to give the title compound. MS (ESI+) m/z 479.1, 481.0 (M+H)$^+$.

Example 20B tert-butyl 4-(methyl((S)-2,2,2-trifluoro-1-(4-((7-((S)-1-methoxyethyl)-2-methylthiazolo[5,4-b]pyridin-6-yl)amino)phenyl)ethyl)carbamoyl)piperidine-1-carboxylate Example 1F (179 mg, 0.800 mmol), Example 20A (383 mg, 0.800 mmol), XPhos Pd G3 (67.7 mg, 0.0800 mmol) and cesium carbonate (782 mg, 2.40 mmol) were combined in dioxane (5.0 mL). The reaction mixture was purged with nitrogen for 10 minutes, stirred at 90° C. for 2 hours, cooled to room temperature, filtered through diatomaceous earth, washed with ethyl acetate and concentrated. The residue was purified by flash chromatography (silica gel, 20-60% ethyl acetate in heptane) to give the title compound. MS (ESI+) m/z 622.3 (M+H)$^+$.

Example 20C

N-methyl-N—((S)-2,2,2-trifluoro-1-(4-((7-((S)-1-methoxyethyl)-2-methylthiazolo[5,4-b]pyridin-6-yl)amino)phenyl)ethyl)piperidine-4-carboxamide To a mixture of Example 20B (410 mg, 0.659 mmol) in dichloromethane (7.5 mL) was added trifluoroacetic acid (2.50 mL, 32.4 mmol). The reaction mixture was stirred at room temperature for 1 hour, and concentrated. The residue was purified by reverse phase HPLC (250×50 mm C18 Phenomenex® LUNA®, 10-100% acetonitrile/0.1% trifluoroacetic acid water solution) to give the title compound as trifluoroacetic acid salt. MS (ESI+) m/z 522.3 (M+H)$^+$.

Example 20D 1-(hydroxyacetyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide To a solution of Example 20C (51 mg, 0.080 mmol), 2-hydroxyacetic acid (6.7 mg, 0.088 mmol) and N,N-diisopropylethylamine (0.042 mL, 0.24 mmol) in N,N-dimethylformamide (1 mL) was added 1-[bis(dimethylamino)methylene]-1H-1,2,3-triazolo[4,5-b]pyridinium 3-oxid hexafluorophosphate (34 mg, 0.088 mmol) portion wise. The reaction mixture was stirred at ambient temperature for 2 hours and purified by reverse phase HPLC (250×50 mm C18 Phenomenex®LUNA®, 10-100% acetonitrile/0.1% trifluoroacetic acid water solution). The fractions containing the product were combined and acetonitrile removed by evaporation. The solution was neutralized with saturated aqueous sodium bicarbonate and extracted with ethyl acetate. The organic layer was dried with anhydrous sodium sulfate, filtered, and the filtrate was concentrated. The residue was lyophilized with acetonitrile/water to afford the title compound. $^1$H NMR (500 MHz, DMSO-d$_6$) δ ppm 8.50 (s, 1H), 7.70 (s, 1H), 7.21 (d, J=8.3 Hz, 2H), 7.05 (d, J=8.7 Hz, 2H), 6.46 (q, J=9.4 Hz, 1H), 5.33 (q, J=6.6 Hz, 1H), 4.50 (s, 1H), 4.35 (d, J=13.1 Hz, 1H), 4.16-4.01 (m, 2H), 3.71 (d, J=13.4 Hz, 1H), 3.21 (s, 3H), 3.09-2.97 (m, 2H), 2.92 (s, 3H), 2.84 (s, 3H), 2.76-2.65 (m, 1H), 1.80-1.66 (m, 2H), 1.66-1.37 (m, 5H). MS (ESI+) m/z 580.2 (M+H)$^+$.

Example 21

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide

Example 21A tert-butyl 4-(((S)-1-(4-((7-((R)-2,2-difluoro-1-methoxyethyl)-2-methylthiazolo[5,4-b]pyridin-6-yl)amino)phenyl)-2,2,2-trifluoroethyl)(methyl)carbamoyl)piperidine-1-carboxylate Example 21A was prepared according to the procedure used for the preparation of Example 20B, substituting Example 3G for Example 1F to provide the title compound. MS (ESI+) m/z 658.6 (M+H)$^+$.

Example 21B

N—((S)-1-(4-((7-((R)-2,2-difluoro-1-methoxyethyl)-2-methylthiazolo[5,4-b]pyridin-6-yl)amino)phenyl)-2,2,2-trifluoroethyl)-N-methylpiperidine-4-carboxamide, trifluoroacetic acid Example 21B was prepared according to the procedure used for the preparation of Example 20C, substituting Example 21A for Example 20B, to provide the title compound. MS (ESI+) m/z 558.4 (M+H)$^+$.

Example 21C

N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide Example 21C was prepared according to the procedure used for the preparation of Example 20D, substituting Example 21B for Example 20C, to provide the title compound. $^1$H NMR (500 MHz, DMSO-d$_6$) δ ppm 8.53 (s, 1H), 7.99 (s, 1H), 7.20 (d, J=8.3 Hz, 2H), 6.97 (d, J=8.7 Hz, 2H), 6.75 (ddd, J=57.6, 54.4, 5.9 Hz, 1H), 6.45 (q, J=9.4 Hz, 1H), 5.31 (dt, J=14.0, 5.6 Hz, 1H), 4.49 (s, 1H), 4.35 (d, J=13.1 Hz, 1H), 4.15-4.01 (m, 2H), 3.70 (d, J=13.2 Hz, 1H), 3.28 (s, 3H), 3.08-2.97 (m, 2H), 2.91 (s, 3H), 2.86 (s, 3H), 2.77-2.65 (m, 1H), 1.80-1.59 (m, 2H), 1.59-1.35 (m, 2H). MS (ESI+) m/z 615.9 (M+H)$^+$.

Example 22

1-(3-hydroxypropanoyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 22 was prepared according to the procedure used for the preparation of Example 20D, substituting 30% 3-hydroxypropanoic acid in water for 2-hydroxyacetic acid, to provide the title compound. $^1$H NMR (600 MHz, DMSO-d$_6$) δ ppm 8.50 (s, 1H), 7.70 (s, 1H), 7.21 (d, J=8.3 Hz, 2H), 7.05 (d, J=8.7 Hz, 2H), 6.46 (q, J=9.4 Hz, 1H), 5.33 (q, J=6.7 Hz, 1H), 4.48 (t, J=5.4 Hz, 1H), 4.40 (d, J=13.1 Hz, 1H), 3.92 (d, J=13.5 Hz, 1H), 3.63 (td, J=6.5, 5.3 Hz, 2H), 3.21 (s, 3H), 3.12-2.98 (m, 2H), 2.92 (s, 3H), 2.84 (s, 3H), 2.69-2.57 (m, 2H), 2.50-2.41 (m, 1H), 1.80-1.61 (m, 2H), 1.58-1.45 (m, 4H), 1.43-1.33 (m, 1H). MS (ESI+) m/z 594.3 (M+H)$^+$.

Example 23

1-(2-hydroxy-2-methylpropanoyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 23 was prepared according to the procedure used for the preparation of Example 20D, substituting 2-hydroxy-2-methylpropanoic acid for 2-hydroxyacetic acid to provide the title compound. $^1$H NMR (600 MHz, DMSO-d$_6$) δ ppm 8.50 (s, 1H), 7.70 (s, 1H), 7.21 (d, J=8.3 Hz, 2H), 7.05 (d, J=8.7 Hz, 2H), 6.46 (q, J=9.4 Hz, 1H), 5.38 (s, 1H), 5.33 (q, J=6.7 Hz, 1H), 4.81 (s, br, 1H), 4.43 (s, br, 1H), 3.21 (s, 3H), 3.10-2.96 (m, 2H), 2.92 (s, 3H), 2.84 (s, 3H), 2.64 (s, 1H), 1.78-1.43 (m, 7H), 1.31 (s, 6H). MS (ESI+) m/z 608.3 (M+H)$^+$.

Example 24

1-(2,3-dihydroxypropanoyl)-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 24 was prepared according to the procedure used for the preparation of Example 20D, substituting 20% 2,3-dihydroxypropanoic acid in water for 2-hydroxyacetic acid to provide the title compound. $^1$H NMR (500 MHz, DMSO-$d_6$) δ ppm 8.50 (s, 1H), 7.70 (s, 1H), 7.21 (d, J=8.3 Hz, 2H), 7.05 (d, J=8.7 Hz, 2H), 6.46 (q, J=9.3 Hz, 1H), 5.33 (q, J=6.7 Hz, 1H), 4.90-4.81 (m, 1H), 4.74-4.62 (m, 1H), 4.42-4.30 (m, 2H), 4.10-4.03 (m, 1H), 3.55-3.48 (m, 1H), 3.47-3.41 (m, 1H), 3.21 (s, 3H), 3.15-3.00 (m, 2H), 2.92 (s, 3H), 2.84 (s, 3H), 2.75-2.65 (m, 1H), 1.80-1.66 (m, 2H), 1.59-1.37 (m, 5H). MS (ESI+) m/z 610.2 (M+H)$^+$.

Example 25

1-[(2R)-2-hydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 25 was prepared according to the procedure used for the preparation of Example 20D, substituting (R)-2-hydroxypropanoic acid for 2-hydroxyacetic acid to provide the title compound. $^1$H NMR (400 MHz, DMSO-$d_6$) δ ppm 8.50 (s, 1H), 7.70 (s, 1H), 7.21 (d, J=8.3 Hz, 2H), 7.05 (d, J=8.6 Hz, 2H), 6.46 (q, J=9.4 Hz, 1H), 5.33 (q, J=6.7 Hz, 1H), 4.87-4.80 (m, 1H), 4.47-4.31 (m, 2H), 4.01 (d, J=12.9 Hz, 1H), 3.21 (s, 3H), 3.13-2.99 (m, 2H), 2.92 (s, 3H), 2.84 (s, 3H), 2.77-2.65 (m, 1H), 1.81-1.66 (m, 2H), 1.60-1.35 (m, 5H), 1.21-1.12 (m, 3H). MS (ESI+) m/z 594.2 (M+H)$^+$.

Example 26

1-[(2S)-2-hydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 26 was prepared according to the procedure used for the preparation of Example 20D, substituting (S)-2-hydroxypropanoic acid for 2-hydroxyacetic acid to provide the title compound. $^1$H NMR (500 MHz, DMSO-$d_6$) δ ppm 8.50 (s, 1H), 7.70 (s, 1H), 7.21 (d, J=8.4 Hz, 2H), 7.05 (d, J=8.7 Hz, 2H), 6.46 (q, J=9.4 Hz, 1H), 5.33 (q, J=6.7 Hz, 1H), 4.84 (d, J=6.9 Hz, 1H), 4.46-4.34 (m, 2H), 4.02 (d, J=13.2 Hz, 1H), 3.21 (s, 3H), 3.14-2.99 (m, 2H), 2.92 (s, 3H), 2.84 (s, 3H), 2.73-2.64 (m, 1H), 1.82-1.66 (m, 2H), 1.63-1.37 (m, 5H), 1.20-1.15 (m, 3H). MS (ESI+) m/z 594.2 (M+H)$^+$.

Example 27

1-[(2R)-2,3-dihydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide

Example 27A (R)-2,2-dimethyl-1,3-dioxolane-4-carboxylic acid

To a solution of (R)-methyl 2,2-dimethyl-1,3-dioxolane-4-carboxylate (1.00 g, 6.24 mmol) in tetrahydrofuran (10 mL) was added a mixture of lithium hydroxide (0.299 g, 12.5 mmol) in water (10 mL). The reaction mixture was stirred at ambient temperature for 2 hours and partitioned with ethyl acetate and water. The organic layer was discarded. The aqueous layer was adjusted to pH 3 by addition of 2 M aqueous HCl and extracted with ethyl acetate three times. The combined organic layers were washed with saturated aqueous sodium chloride, dried with anhydrous sodium sulfate, filtered, and the filtrate was concentrated to afford the title compound.

Example 27B

1-[(2R)-2,3-dihydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide To a solution of Example 20C (153 mg, 0.240 mmol), Example 27A (35.1 mg, 0.240 mmol), and N,N-diisopropylethylamine (0.126 mL, 0.720 mmol) in NN-dimethyl formamide (2.0 mL) was added 1-[bis(dimethylamino)methylene]-1H-1,2,3-triazolo[4,5-b]pyridinium 3-oxid hexafluorophosphate (100 mg, 0.264 mmol) portion wise. The reaction mixture was stirred at ambient temperature for 2 hours, and purified by reverse phase HPLC (250×50 mm C18 Phenomenex® LUNA, 10-100% acetonitrile/0.1% trifluoroacetic acid water solution) to afford the title compound and the protected intermediate. The fractions of protected intermediate were concentrated, dissolved in the mixture of acetic acid (1.0 mL)/water (0.50 mL), stirred at 70° C. for 15 minutes, cooled to ambient temperature and concentrated. The residue was purified by reverse phase HPLC (250×50 mm C18 Phenomenex® LUNA®, 10-100% acetonitrile/0.1% trifluoroacetic acid water solution). The combined fractions of the title compound were concentrated to remove acetonitrile, neutralized with saturated aqueous sodium bicarbonate, and extracted with ethyl acetate. The organic layer was dried with anhydrous sodium sulfate, filtered, and the filtrate was concentrated. The residue was lyophilized with acetonitrile/water to afford the title compound. $^1$H NMR (500 MHz, DMSO-$d_6$) δ ppm 8.50 (s, 1H), 7.70 (s, 1H), 7.21 (d, J=8.4 Hz, 2H), 7.05 (d, J=8.7 Hz, 2H), 6.46 (q, J=9.4 Hz, 1H), 5.33 (q, J=6.7 Hz, 1H), 4.92-4.81 (m, 1H), 4.72-4.62 (m, 1H), 4.43-4.29 (m, 2H), 4.11-4.03 (m, 1H), 3.56-3.48 (m, 1H), 3.47-3.40 (m, 1H), 3.21 (s, 3H), 3.14-3.00 (m, 2H), 2.92 (s, 3H), 2.84 (s, 3H), 2.76-2.65 (m, 1H), 1.80-1.65 (m, 2H), 1.63-1.53 (m, 1H), 1.52 (d, J=6.7 Hz, 3H), 1.48-1.37 (m, 1H). MS (ESI+) m/z 610.3 (M+H)$^+$.

Example 28

N-{(1S)-2,2-difluoro-1-[4-({7-[(1S)-1-methoxyethyl]-2-methyl[1,3]thiazolo[5,4-b]pyridin-6-yl}amino)phenyl]ethyl}-1-(hydroxyacetyl)-N-methylpiperidine-4-carboxamide

Example 28A tert-butyl 4-(((S)-2,2-difluoro-1-(4-((7-((S)-1-methoxyethyl)-2-methylthiazolo[5,4-b]pyridin-6-yl)amino)phenyl)ethyl)(methyl)carbamoyl)piperidine-1-carboxylate 1-(tert-Butoxycarbonyl)piperidine-4-carboxylic acid (73.6 mg, 0.321 mmol), 2,4-dichloro-6-methoxy-1,3,5-triazine (69.3 mg, 0.385 mmol), and N-methylmorpholine (42.4 µL, 0.385 mmol) were mixed in dichloromethane (1.6 mL) and stirred at ambient temperature for 1 hour. The resulting suspension was dropwise added to a solution of Example 4C (126 mg, 0.321 mmol) in dichloromethane (1.6 mL), and the mixture was stirred at ambient temperature overnight. The reaction was concentrated and directly purified by flash chromatography (0-70% ethyl acetate/heptanes) to afford the title compound. MS (ESI) m/z 604.4 (M+H)$^+$.

Example 28B

N—((S)-2,2-difluoro-1-(4-((7-((S)-1-methoxyethyl)-2-methylthiazolo[5,4-b]pyridin-6-yl)amino)phenyl)ethyl)-N-methylpiperidine-4-carboxamide To a mixture of Example 28A (104 mg, 0.172 mmol) in dichloromethane (3.5 mL) was added trifluoroacetic acid (0.67 mL, 8.61 mmol). The mixture was stirred at ambient temperature for 1 hour, and concentrated. The residue was purified by flash chromatography (12 g silica gel, 2-10% methanol/dichloromethane with 3% NH$_4$OH) to afford the title compound. MS (ESI) m/z 504.4 (M+H)$^+$.

Example 28C

N-{(1S)-2,2-difluoro-1-[4-({7-[(1S)-1-methoxyethyl]-2-methyl[1,3]thiazolo[5,4-b]pyridin-6-yl}amino)phenyl]ethyl}-1-(hydroxyacetyl)-N-methylpiperidine-4-carboxamide To a solution of Example 28B (50 mg, 0.099 mmol), 2-hydroxyacetic acid (5.07 µL, 0.099 mmol), and N,N-diisopropylethylamine (34.7 µL, 0.199 mmol) in N,N-dimethylformamide (1.0 mL) was dropwise added a solution of (1-[bis(dimethylamino)methylene]-1H-1,2,3-triazolo[4,5-b]pyridinium 3-oxid hexafluorophosphate (41.5 mg, 0.109 mmol) in N,N-dimethylformamide (1.0 mL). The mixture was stirred at ambient temperature for 2 hours, and directly purified by reverse phase HPLC (250×50 mm C18 Phenomenex® LUNA®, 10-90% acetonitrile/0.1% trifluoroacetic acid water solution). The fractions containing the product were concentrated and redissolved in acetonitrile. The sample was desalted by filtering through a 1 g SiliCycle SiliaPrep carbonate cartridge to afford the title compound. $^1$H NMR (400 MHz, DMSO-d$_6$) δ ppm 8.46 (s, 1H), 7.48 (s, 1H), 7.25 (d, J=8.3 Hz, 2H), 7.04 (d, J=8.6 Hz, 2H), 6.64 (td, J=55.0, 5.1 Hz, 1H), 5.70 (s, 1H), 5.40 (q, J=6.6 Hz, 1H), 4.40-3.65 (m, 5H), 3.28 (s, 3H), 3.05-2.85 (m, 6H), 2.83 (s, 3H), 1.71 (d, J=10.4 Hz, 2H), 1.54 (m, 5H). MS (APCI) m/z 562.3 (M+H)$^+$.

Example 29

1-acetyl-N-{(1S)-2,2-difluoro-1-[4-({7-[(1S)-1-methoxyethyl]-2-methyl[1,3]thiazolo[5,4-b]pyridin-6-yl}amino)phenyl]ethyl}-N-methylpiperidine-4-carboxamide To a solution of Example 28B (45 mg, 0.089 mmol) and triethylamine (31.1 µL, 0.223 mmol) in N,N-dimethylformamide (0.9 mL) was added acetyl chloride (7.62 µL, 0.107 mmol) dropwise. The mixture was stirred at ambient temperature for 2 hours, and directly purified by reverse phase HPLC (250×50 mm C18 Phenomenex® LUNA®, 10-90% acetonitrile/0.1% trifluoroacetic acid water solution). The desired fractions were concentrated and redissolved in acetonitrile. The sample was desalted by filtering through a 1 g SiliCycle SiliaPrep carbonate cartridge to afford the title compound. $^1$H NMR (400 MHz, DMSO-d$_6$) δ ppm 8.46 (s, 1H), 7.48 (s, 1H), 7.25 (d, J=8.3 Hz, 2H), 7.04 (d, J=8.6 Hz, 2H), 6.64 (td, J=55.2, 5.1 Hz, 1H), 5.70 (s, 1H), 5.40 (q, J=6.6 Hz, 1H), 4.50-3.60 (m, 2H), 3.28 (s, 3H), 3.12-2.85 (br, 6H), 2.83 (s, 3H), 1.99 (s, 3H), 1.70 (d, J=11.4 Hz, 2H), 1.63-1.41 (m, 5H). MS (APCI) m/z 546.4 (M+H)$^+$.

Example 30

1-[(2S)-2,3-dihydroxypropanoyl]-N-methyl-N-{(1S)-2,2,2-trifluoro-1-[4-({7-[(1S)-1-methoxyethyl]-2-methyl[1,3]thiazolo[5,4-b]pyridin-6-yl}amino)phenyl]ethyl}piperidine-4-carboxamide Example 30 was prepared according to the procedure used for the preparation of Example 20D, substituting (S)-2,3-dihydroxypropanoic acid for 2-hydroxyacetic acid to provide the title compound (26 mg, 18%). $^1$H NMR (400 MHz, DMSO-d$_6$) δ ppm 8.50 (s, 1H), 7.70 (s, 1H), 7.21 (d, J=8.3 Hz, 2H), 7.05 (d, J=8.6 Hz, 2H), 6.46 (q, J=9.4 Hz, 1H), 5.33 (q, J=6.7 Hz, 1H), 4.89-4.80 (m, 1H), 4.72-4.59 (m, 1H), 4.42-4.30 (m, 2H), 4.12-4.02 (m, 1H), 3.57-3.47 (m, 1H), 3.47-3.40 (m, 1H), 3.21 (s, 3H), 3.13-2.99 (m, 2H), 2.92 (s, 3H), 2.84 (s, 3H), 2.75-2.65 (m, 1H), 1.82-1.67 (m, 2H), 1.63-1.36 (m, 5H). MS (ESI+) m/z 610.3 (M+H)$^+$.

Example 31

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-1-(hydroxyacetyl)-N-methylpiperidine-4-carboxamide Example 31A tert-butyl 4-(((S)-1-(4-((7-((R)-2,2-difluoro-1-methoxyethyl)-2-methylthiazolo[5,4-b]pyridin-6-yl)amino)phenyl)-2,2-difluoroethyl)(methyl)carbamoyl)piperidine-1-carboxylate The title compound (100 mg, 45%) was prepared using the conditions described in Example 28A, substituting Example 6A for Example 4C. MS (APCI) m/z 640.4 (M+H)$^+$.

Example 31B

N—((S)-1-(4-((7-((R)-2,2-difluoro-1-methoxyethyl)-2-methylthiazolo[5,4-b]pyridin-6-yl)amino)phenyl)-2,2-difluoroethyl)-N-methylpiperidine-4-carboxamide The title compound (70 mg, 83%) was prepared using the conditions described in Example 28B, substituting Example 31A for Example 28A. MS (APCI) m/z 540.4 (M+H)$^+$.

Example 31C

N-{(1S)-1-[4-({7-[(1R)-2,2-difluoro-1-methoxyethyl]-2-methyl[1,3]thiazolo[5,4-b]pyridin-6-yl}amino)phenyl]-2,2-difluoroethyl}-1-(hydroxyacetyl)-N-methylpiperidine-4-carboxamide The title compound (33.4 mg, 43%) was prepared using the conditions described in Example 28C, substituting Example 31B for Example 28B. $^1$H NMR (400 MHz, DMSO-d$_6$) δ ppm 8.48 (s, 1H), 7.60 (s, 1H), 7.24 (d, J=8.4 Hz, 2H), 6.97 (d, J=8.6 Hz, 2H), 6.85-6.41 (m, 2H), 5.70 (s, 1H), 5.40 (ddd, J=13.1, 7.3, 5.5 Hz, 1H), 4.38-3.56 (m, 5H), 3.36 (s, 3H), 3.00-2.96 (m, 3H), 2.92 (s, 3H), 2.85 (s, 3H), 1.71 (d, J=8.3 Hz, 2H), 1.54 (d, J=12.9 Hz, 2H). MS (APCI) m/z 598.4 (M+H)$^+$.

Example 32

N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide

Example 32A (S)-tert-butyl 4-((1-(4-bromophenyl)-2,2,2-trifluoroethyl)(methyl)carbamoyl)piperidine-1-carboxylate 1-(tert-Butoxycarbonyl)piperidine-4-carboxylic acid (2.45 g, 10.7 mmol), 2,4-dichloro-6-methoxy-1,3,5-triazine (1.77 g, 9.85 mmol), CH$_2$Cl$_2$ (50 mL), and N-methylmorpholine (1.08 mL, 9.85 mmol) were stirred at ambient temperature for 1 hour. To this solution was added Example 1I (2.50 g, 8.21 mmol), and the combined solution was stirred at ambient temperature for 15 hours. Upon completion as determined by LCMS, the reaction mixture was concentrated. The residue was purified on silica gel (0-100% ethyl acetate/heptanes). The residue was further purified by reverse phase chromatography (C18 HPLC, eluting with 20-100% acetonitrile in water/0.1% trifluoroacetic acid) to isolate the title compound. Clean fractions were combined and concentrated. The aqueous solution was partitioned with ethyl acetate and neutralized with saturated aqueous sodium bicarbonate to free base the desired product. The organic layer was dried over anhydrous magnesium sulfate, filtered, and the filtrate was concentrated to afford the title compound. $^1$H NMR (400 MHz, DMSO-d$_6$) δ ppm 7.80-7.61 (m, 2H), 7.30 (d, J=8.3 Hz, 2H), 6.55 (q, J=9.2 Hz, 1H), 3.96 (d, J=13.3 Hz, 2H), 3.08-2.67 (m, 6H), 1.70 (t, J=16.9 Hz, 2H), 1.40 (s, 11H). MS (ESI+) m/z 479.6 and 481.7 (M+H)$^+$.

Example 32B tert-butyl 4-(((S)-1-(4-((7-((S)-2,2-difluoro-1-methoxyethyl)-2-methylthiazolo[5,4-b]pyridin-6-yl)amino)phenyl)-2,2,2-trifluoroethyl)(methyl)carbamoyl)piperidine-1-carboxylate Example 3H (0.500 g, 2.24 mmol), Example 32A (0.75 g, 1.57 mmol), and cesium carbonate (1.51 g, 4.63 mmol) in 1,4-dioxane (30 mL) were sparged with N$_2$ for 2 minutes. XPhos Pd G4 (0.20 g, 0.23 mmol) was added, and the reaction mixture was heated at 95° C. for 16 hours. The reaction mixture was cooled, filtered through diatomaceous earth, and the diatomaceous earth pad was washed with ethyl acetate. The filtrate was concentrated. The material was purified on silica gel (0-70% ethyl acetate/heptanes) to afford the title compound. $^1$H NMR (500 MHz, DMSO-d$_6$) δ ppm 8.53 (s, 1H), 7.99 (s, 1H), 7.20 (d, J=8.3 Hz, 2H), 7.01-6.91 (m, 2H), 6.76 (ddd, J=57.7, 54.3, 6.0 Hz, 1H), 6.46 (q, J=9.3 Hz, 1H), 5.32 (dt, J=14.2, 5.5 Hz, 1H), 3.99 (dd, J=39.7, 10.1 Hz, 2H), 3.28 (s, 3H), 2.88 (d, J=20.3 Hz, 9H), 1.68 (dd, J=34.8, 12.9 Hz, 2H), 1.40 (s, 11H). MS (ESI) m/z 658.7 (M+H)$^+$.

Example 32C

N—((S)-1-(4-((7-((S)-2,2-difluoro-1-methoxyethyl)-2-methylthiazolo[5,4-b]pyridin-6-yl)amino)phenyl)-2,2,2-trifluoroethyl)-N-methylpiperidine-4-carboxamide Example 32B (0.95 g, 1.45 mmol) was dissolved in a 1:1 mixture of dichloromethane (3 mL) and trifluoroacetic acid (3 mL, 38.9 mmol). The solution was left at ambient temperature for 30 minutes. After complete consumption of the starting material, the reaction mixture was concentrated. The residue was dissolved in ethyl acetate and washed with saturated aqueous sodium bicarbonate. The aqueous layer was extracted with dichloromethane (20 mL). The combined organic layers were dried with anhydrous magnesium sulfate, filtered, and the filtrate was concentrated to afford the title compound. $^1$H NMR (600 MHz, DMSO-d$_6$) δ ppm 8.53 (s, 1H), 8.00 (s, 1H), 7.20 (d, J=8.4 Hz, 2H), 7.03-6.94 (m, 2H), 6.75 (ddd, J=57.8, 54.3, 5.9 Hz, 1H), 6.44 (q, J=9.3 Hz, 1H), 5.31 (dt, J=14.1, 5.5 Hz, 1H), 3.28 (s, 3H), 3.11-2.83 (m, 11H), 1.94-1.56 (m, 5H). MS (ESI) m/z 558.3 (M+H)$^+$.

Example 32D

N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-1-(hydroxyacetyl)-N-methylpiperidine-4-carboxamide To a solution of 2-hydroxyacetic acid (0.033 g, 0.43 mmol), Example 32C (0.20 g, 0.36 mmol), NN-dimethyl formamide (3 mL) and N,N-diisopropylethylamine (0.31 mL, 1.79 mmol) was added 1-[bis(dimethylamino)methylene]-1H-1,2,3-triazolo[4,5-b]pyridinium 3-oxid hexafluorophosphate (0.15 g, 0.40 mmol) in three portions over 10 minutes. The combined solution was stirred at ambient temperature for 1 hour. Upon complete consumption of starting material, the crude material was directly purified by reverse phase chromatography (C18 HPLC, eluting with 20-100% acetonitrile in water/0.1% trifluoroacetic acid) to isolate the title compound. Clean fractions were combined and concentrated. The aqueous solution was partitioned with ethyl acetate and neutralized with saturated aqueous sodium bicarbonate to free base the desired product. The organic layer was dried over anhydrous magnesium sulfate, filtered, and the filtrate was concentrated. The residue was lyophilized to provide the title compound. $^1$H NMR (600 MHz, DMSO-d$_6$) δ ppm 8.53 (s, 1H), 7.99 (s, 1H), 7.20 (d, J=8.4 Hz, 2H), 7.02-6.94 (m, 2H), 6.75 (ddd, J=57.8, 54.3, 5.9 Hz, 1H), 6.45 (q, J=9.3 Hz, 1H), 5.32 (dt, J=14.1, 5.5 Hz, 1H), 4.49 (t, J=5.4 Hz, 1H), 4.35 (d, J=12.9 Hz, 1H), 4.23-4.01 (m, 2H), 3.70 (d, J=13.8 Hz, 1H), 3.28 (s, 3H), 3.03 (tq, J=11.1, 3.6 Hz, 1H), 2.92 (s, 3H), 2.86 (s, 3H), 2.71 (dt, J=24.0, 13.0 Hz, 1H), 1.84-1.32 (m, 5H). MS (ESI) m/z 616.0 (M+H)$^+$.

Example 33

1-acetyl-N-{(1S)-1-[4-({7-[(1S)-2,2-difluoro-1-methoxyethyl]-2-methyl[1,3]thiazolo[5,4-b]pyridin-6-yl}amino)phenyl]-2,2,2-trifluoroethyl}-N-methylpiperidine-4-carboxamide A solution of acetic acid (0.097 g, 1.6 mmol), 1-[bis(dimethylamino)methylene]-1H-1,2,3-triazolo[4,5-b]pyridinium 3-oxid hexafluorophosphate (0.31 g, 0.81 mmol), NN-dimethyl formamide (2 mL), and N,N-diisopropylethylamine (0.47 mL, 2.7 mmol) was added to a solution of Example 32C (0.30 g, 0.54 mmol) in N,N-dimethyl formamide (1.0 mL). The combined mixture was stirred at ambient temperature for 20 minutes. LCMS showed full conversion. Upon complete consumption of starting material, the crude material was directly purified by reverse phase chromatography (C18 HPLC, eluting with 20-80% acetonitrile in water/0.1% trifluoroacetic acid) to isolate the title compound. Clean fractions were combined and concentrated. The aqueous solution was partitioned with ethyl acetate and neutralized with saturated aqueous sodium bicarbonate to free base the desired product. The organic layer was dried over anhydrous magnesium sulfate, filtered, and the filtrate was concentrated. The residue was lyophilized to provide the title compound. $^1$H NMR (400 MHz, DMSO-$d_6$) δ ppm 8.53 (s, 1H), 8.00 (s, 1H), 7.20 (d, J=8.3 Hz, 2H), 7.07-6.94 (m, 2H), 6.92-6.58 (m, 1H), 6.44 (t, J=9.4 Hz, 1H), 5.31 (dt, J=13.8, 5.6 Hz, 1H), 4.37 (d, J=13.1 Hz, 1H), 3.83 (d, J=13.4 Hz, 1H), 3.28 (s, 3H), 3.05 (dt, J=41.6, 11.7 Hz, 1H), 2.91 (s, 3H), 2.86 (s, 3H), 2.61 (q, J=19.1, 16.6 Hz, 2H), 1.99 (d, J=1.8 Hz, 3H), 1.87-1.22 (m, 4H). MS (ESI) m/z 600.5 (M+H)$^+$.

Example 34

1-(hydroxyacetyl)-N-methyl-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}piperidine-4-carboxamide Example 34A tert-butyl 4-(methyl((S)-2,2,2-trifluoro-1-(4-((7-((R)-1-methoxyethyl)-2-methylthiazolo[5,4-b]pyridin-6-yl)amino)phenyl)ethyl)carbamoyl)piperidine-1-carboxylate Example 34A was prepared according to the procedure used for the preparation of Example 32B, substituting Example 8B for Example 3H, to provide the title compound. $^1$H NMR (600 MHz, DMSO-$d_6$) δ ppm 8.50 (s, 1H), 7.70 (s, 1H), 7.21 (d, J=8.3 Hz, 2H), 7.09-6.99 (m, 2H), 6.45 (t, J=9.4 Hz, 1H), 5.33 (q, J=6.7 Hz, 1H), 3.95 (s, 2H), 3.21 (s, 3H), 2.87 (d, J=43.2 Hz, 7H), 1.68 (dd, J=42.3, 13.3 Hz, 2H), 1.52 (d, J=6.7 Hz, 3H), 1.40 (m, 13H). MS (ESI) m/z 622.4 (M+H)$^+$.

Example 34B

N-methyl-N—((S)-2,2,2-trifluoro-1-(4-((7-((R)-1-methoxyethyl)-2-methylthiazolo[5,4-b]pyridin-6-yl)amino)phenyl)ethyl)piperidine-4-carboxamide Example 34B was prepared according to the procedure used for the preparation of Example 32C, substituting Example 34A for Example 32B to provide the title compound. $^1$H NMR (600 MHz, DMSO-$d_6$) δ ppm 8.50 (s, 1H), 7.72 (s, 1H), 7.22 (d, J=8.4 Hz, 2H), 7.06-6.97 (m, 2H), 6.45 (q, J=9.3 Hz, 1H), 5.33 (q, J=6.7 Hz, 1H), 3.21 (s, 3H), 3.12-2.87 (m, 8H), 2.84 (s, 3H), 1.95-1.66 (m, 4H), 1.52 (d, J=6.6 Hz, 3H). MS (ESI) m/z 522.4 (M+H)$^+$.

Example 34C 1-(hydroxyacetyl)-N-methyl-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}piperidine-4-carboxamide Example 34C was prepared according to the procedure used for the preparation of Example 32D, substituting Example 34B for Example 32C to provide the title compound. $^1$H NMR (600 MHz, DMSO-$d_6$) δ ppm 8.50 (s, 1H), 7.70 (s, 1H), 7.21 (d, J=8.3 Hz, 2H), 7.09-7.03 (m, 2H), 6.46 (q, J=9.4 Hz, 1H), 5.32 (q, J=6.7 Hz, 1H), 4.49 (t, J=5.4 Hz, 1H), 4.35 (d, J=12.9 Hz, 1H), 4.17-3.99 (m, 2H), 3.70 (d, J=13.6 Hz, 1H), 3.21 (s, 3H), 3.10-2.98 (m, 1H), 2.92 (s, 3H), 2.84 (s, 3H), 2.71 (dt, J=24.4, 12.5 Hz, 1H), 1.82-1.33 (m, 8H). MS (ESI) m/z 580.4 (M+H)$^+$.

Example 35

1-acetyl-N-methyl-N-{(1S)-2,2,2-trifluoro-1-[4-({7-[(1R)-1-methoxyethyl]-2-methyl[1,3]thiazolo[5,4-b]pyridin-6-yl}amino)phenyl]ethyl}piperidine-4-carboxamide Example 35 was prepared according to the procedure used for the preparation of Example 33, substituting Example 34B for Example 32C to provide the title compound. $^1$H NMR (500 MHz, DMSO-$d_6$) δ ppm 8.51 (s, 1H), 7.70 (s, 1H), 7.21 (d, J=8.2 Hz, 2H), 7.10-7.02 (m, 2H), 6.46 (q, J=9.4 Hz, 1H), 5.33 (q, J=6.7 Hz, 1H), 4.40-4.33 (m, 1H), 3.86-3.79 (m, 1H), 3.21 (s, 3H), 3.16-2.96 (m, 2H), 2.92 (s, 3H), 2.84 (s, 3H), 2.64 (d, J=7.1 Hz, 1H), 2.00 (d, J=2.3 Hz, 3H), 1.75 (t, J=15.7 Hz, 1H), 1.66 (d, J=16.2 Hz, 1H), 1.52 (d, J=6.6 Hz, 4H), 1.44-1.31 (m, 1H). MS (ESI) m/z 564.7 (M+H)$^+$.

Example 36

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-1-(hydroxyacetyl)-N-methylpiperidine-4-carboxamide Example 36A tert-butyl 4-(((S)-2,2-difluoro-1-(4-((2-methyl-7-((R)-2,2,2-trifluoro-1-methoxyethyl)thiazolo[5,4-b]pyridin-6-yl)amino)phenyl)ethyl)(methyl)carbamoyl)piperidine-1-carboxylate The title compound (175.7 mg, 51%) was prepared using the conditions described in Example 28A substituting Example 14A for Example 4C. MS (APCI) m/z 640.4 (M+H)$^+$.

Example 36B

N—((S)-2,2-difluoro-1-(4-((2-methyl-7-((R)-2,2,2-trifluoro-1-methoxyethyl)thiazolo[5,4-b]pyridin-6-yl)amino)phenyl)ethyl)-N-methylpiperidine-4-carboxamide The title compound (149.9 mg, 100%) was prepared using the conditions described in Example 28B substituting Example 36A for Example 28A. MS (APCI) m/z 558.4 (M+H)$^+$.

Example 36C

N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-1-(hydroxyacetyl)-N-methylpiperidine-4-carboxamide The title compound (58.6 mg, 71%) was prepared using the conditions described in Example 28C, substituting Example 36B for Example 28B. $^1$H NMR (400 MHz, DMSO-d$_6$) δ ppm 8.53 (s, 1H), 7.37 (s, 1H), 7.28 (d, J=8.3 Hz, 2H), 7.12 (d, J=8.6 Hz, 2H), 6.66 (td, J=55.2, 5.1 Hz, 1H), 5.94 (q, J=7.7 Hz, 1H), 5.72 (s, 1H), 4.36-3.70 (m, 5H), 3.56 (s, 3H), k 2.85 (s, 3H), 1.72 (dd, J=13.0, 6.8 Hz, 2H), 1.55 (d, J=12.9 Hz, 2H). MS (APCI) m/z 616.0 (M+H)$^+$.

Example 37

1-acetyl-N-{(1S)-2,2-difluoro-1-[4-({2-methyl-7-[(1R)-2,2,2-trifluoro-1-methoxyethyl][1,3]thiazolo[5,4-b]pyridin-6-yl}amino)phenyl]ethyl}-N-methylpiperidine-4-carboxamide The title compound was prepared using the conditions described in Example 29, substituting Example 36B for Example 28B. $^1$H NMR (400 MHz, DMSO-d$_6$) δ ppm 8.53 (s, 1H), 7.37 (s, 1H), 7.28 (d, J=8.4 Hz, 2H), 7.12 (d, J=8.6 Hz, 2H), 6.66 (td, J=55.1, 5.1 Hz, 1H), 5.94 (q, J=7.7 Hz, 1H), 5.72 (s, 1H), 4.57-3.65 (m, 2H), 3.56 (s, 3H), 2.99-2.87 (m, 6H), 2.85 (s, 3H), 1.99 (s, 3H), 1.78-1.65 (m, 2H), 1.63-1.39 (m, 2H). MS (APCI) m/z 600.3 (M+H)$^+$.

Example 38

N-methyl-1,1-dioxo-N-{(1S)-2,2,2-trifluoro-1-[4-({2-methyl-7-[(2R)-1,1,1-trifluoropropan-2-yl][1,3]thiazolo[5,4-b]pyridin-6-yl}amino)phenyl]ethyl}-1λ$^6$-thiane-4-carboxamide Example 38A To a solution of ethyl 7-chloro-2-methylthiazolo[5,4-b]pyridine-6-carboxylate (50 g, 195 mmol) in 1,4-dioxane (600 mL) and water (500 mL) was added LiOH (4.66 g, 195 mmol). The reaction mixture was stirred at 20° C. for 3 hours. The resulting solution was acidified to pH 2 with a 1 M aqueous HCl solution and filtered to afford the crude title compound. The crude material was used as is in the next step. LCMS (ESI) m/z 375 (M+H)$^+$.

Example 38B tert-butyl (7-chloro-2-methylthiazolo[5,4-b]pyridin-6-yl)carbamate

To a mixture of Example 38A (30 g, 131 mmol), triethylamine (54.9 mL, 394 mmol) in tert-butanol (600 mL) was added diphenylphosphoryl azide (43.3 g, 157 mmol) and the mixture was stirred at 90° C. for 12 hours. Next, the reaction mixture was concentrated to remove the tert-butanol and the residue obtained was diluted with water (10 mL) and extracted with ethyl acetate (3×20 mL). The combined organic layers were washed with brine (50 mL), dried over Na$_2$SO$_4$, filtered, and the filtrate was concentrated. The residue was purified by silica gel flash column chromatography (0-100% ethyl acetate/petroleum ether) to afford the title compound. $^1$H NMR (300 MHz, DMSO-d$_6$) δ ppm 1.48 (s, 9H), 2.87 (s, 3H), 8.62 (s, 1H), 9.21 (s, 1H). LCMS (ESI) m/z 300 (M+H)$^+$.

Example 38C tert-butyl (7-iodo-2-methylthiazolo[5,4-b]pyridin-6-yl)carbamate

Example 38B (12.5 g, 41.7 mmol) was dissolved in acetonitrile (180 mL) and treated with sodium iodide (18.75 g, 125 mmol). The mixture was cooled to 0° C. before the addition of acetyl chloride (3.56 mL, 50.0 mmol). The reaction was stirred for 3 hours at 0° C. The reaction mixture was poured into a stirred cooled (10° C.) saturated solution of sodium hydrogen carbonate (500 mL). Following this, 1M sodium thiosulfate solution (100 mL) was added, and the suspension was stirred for 5 minutes before being filtered and washed with water (100 mL). The filtrate was collected and triturated with ethyl acetate (500 mL) and filtered again. The residue was dried in a desiccator overnight to afford the title compound. $^1$H NMR (300 MHz, DMSO-d$_6$) δ ppm 1.48 (s, 9H), 2.86 (s, 3H), 8.32 (s, 1H), 9.00 (s, 1H). LCMS (ES) m/z 392 (M+H)$^+$.

Example 38D tert-butyl (2-methyl-7-(3,3,3-trifluoroprop-1-en-2-yl)thiazolo[5,4-b]pyridin-6-yl)carbamate To a degassed suspension of Example 38C (2.4 g), 4,4,6-trimethyl-2-(3,3,3-trifluoroprop-1-en-2-yl)-1,3,2-dioxaborinane (2.043 g), and cesium carbonate (6.00 g) in 1,2-dimethoxyethane (20 mL) and water (2 mL) was added [bis(diphenylphosphino)ferrocene]dichloropalladium(II)-dichloromethane adduct (0.501 g). The reaction mixture was stirred under microwave irradiation at 110° C. for 90 minutes. The reaction mixture was cooled to ambient temperature and degassed again, and [bis(diphenylphosphino)ferrocene]dichloropalladium(II)-dichloromethane adduct (0.250 g) was added. The reaction mixture was stirred under microwave irradiation at 110° C. for 90 minutes. The reaction mixture was cooled to ambient temperature and partitioned between water (30 mL) and ethyl acetate (80 mL). The aqueous layer was adjusted to pH 7 by addition of 1 M aqueous HCl and was extracted with ethyl acetate (50 mL). The combined organic extracts were dried over magnesium sulfate, filtered, and the filtrate was concentrated in vacuo. The crude product was purified by chromatography on silica gel (0-40% ethyl acetate/2-methylpentane) to afford the title compound. MS (ESI) m/z 360.2 (M+H)$^+$.

Example 38E tert-butyl (2-methyl-7-(1,1,1-trifluoropropan-2-yl)thiazolo[5,4-b]pyridin-6-yl)carbamate To a solution of Example 38D (200 mg) in ethanol (10 mL) was added palladium (5 weight % on carbon, 59.2 mg). The reaction mixture was stirred under atmosphere of hydrogen (5 bar) at 50° C. overnight. The reaction mixture was cooled to ambient temperature, diluted with ethanol (10 mL) and filtered through diatomaceous earth. The filtrate was concentrated in vacuo to afford the title compound. MS (ESI) m/z 362.1 (M+H)$^+$.

Example 38F 2-methyl-7-(1,1,1-trifluoropropan-2-yl)thiazolo[5,4-b]pyridin-6-amine To a solution of Example 38E (175 mg) in dichloromethane (5 mL) was added 2,2,2-trifluoroacetic acid (1.119 mL). The reaction mixture was stirred overnight and then concentrated in vacuo. The residue was dissolved in dichloromethane (15 mL) and washed with saturated aqueous sodium hydrogen carbonate (20 mL). The aqueous layer was further extracted with dichloromethane (5 mL). The combined organic extracts were concentrated in vacuo. The crude product was purified by chromatography on silica gel (0-50% ethyl acetate/2-methylpentane) to afford the title compound. MS (ESI) m/z 262.1 (M+H)$^+$.

Example 38G

N-methyl-1,1-dioxo-N-{(1S)-2,2,2-trifluoro-1-[4-({2-methyl-7-[(2R)-1,1,1-trifluoropropan-2-yl][1,3]thiazolo[5,4-b]pyridin-6-yl}amino)phenyl]ethyl}-1λ$^6$-thiane-4-carboxamide and Example 39

N-methyl-1,1-dioxo-N-{(1S)-2,2,2-trifluoro-1-[4-({2-methyl-7-[(2S)-1,1,1-trifluoropropan-2-yl][1,3]thiazolo[5,4-b]pyridin-6-yl}amino)phenyl]ethyl}-1λ$^6$-thiane-4-carboxamide To a degassed mixture of Example 38F (65 mg), Example 1J (107 mg), and cesium carbonate (243 mg) in 1,4dioxane (2 mL) was added XantPhos Pd G3 (23.59 mg), and the mixture was stirred at 90° C. for 2 hours. The reaction mixture was cooled to ambient temperature, filtered through diatomaceous earth, washed with dichloromethane (12 mL), and the filtrate was concentrated in vacuo. The crude product was purified by chromatography on silica gel (0-25% acetonitrile/dichloromethane) to afford the title compounds as a mixture of diastereomers. The mixture of diastereomers was separated by chiral SFC (supercritical fluid chromatography) using a CHIRALPAK® IG column (10×250 mm, 5 micron), eluting with 40% ethanol (0.1% ammonia) in $CO_2$ at 40° C., 15 mL/minute, 120 bar, to afford the title compounds as individual diastereomers. The absolute stereochemistry of these title compounds was arbitrarily assigned. The fast-eluting diastereomer corresponds to Example 38G and the slow-eluting diastereomer corresponds to Example 39. Example 38G: $^1$H NMR (400 MHz, DMSO-d$_6$, 90° C.) δ ppm 8.43 (s, 1H), 7.77 (s, 1H), 7.19 (d, 2H), 6.88-6.73 (m, 2H), 6.40 (s, 1H), 4.52 (dd, 1H), 3.26-3.05 (m, 5H), 2.90 (s, 3H), 2.86 (s, 3H), 2.18-2.00 (m, 4H), 1.77 (d, 3H). MS (ESI) m/z 609.4 (M+H)$^+$. Example 39: $^1$H NMR (400 MHz, DMSO-d$_6$, 90° C.) δ ppm 8.43 (s, 1H), 7.77 (s, 1H), 7.19 (d, 2H), 6.85-6.75 (m, 2H), 6.39 (s, 1H), 4.53 (dd, 1H), 3.27-3.04 (m, 5H), 2.90 (s, 3H), 2.86 (s, 3H), 2.16-2.01 (m, 4H), 1.77 (d, 3H). MS (ESI) m/z 609.4 (M+H)$^+$.

Comparative Example A

N-{(1S)-1-[4-({2-chloro-7-[(1S)-1-methoxyethyl]pyrazolo[1,5-a]pyrimidin-6-yl}amino)phenyl]-2,2,2-trifluoroethyl}-N-methyl-1,1-dioxo-1λ$^6$-thiane-4-carboxamide Comparative Example A was prepared according to the procedure used for the preparation of Example 1K, substituting (S)-2-chloro-7-(1-methoxyethyl)pyrazolo[1,5-a]pyrimidin-6-amine for Example 1J to provide the title compound. (S)-2-chloro-7-(1-methoxyethyl)pyrazolo[1,5-a]pyrimidin-6-amine was obtained as described in WO2018226150, Intermediate I-2b page 87. $^1$H NMR (500 MHz, DMSO-d$_6$) δ ppm 8.55 (s, 1H), 7.81 (s, 1H), 7.20 (d, J=8.4 Hz, 2H), 6.98-6.90 (m, 3H), 6.44 (q, J=9.3 Hz, 1H), 5.29 (q, J=6.7 Hz, 1H), 3.30-3.07 (m, 7H), 2.91 (s, 3H), 2.15-1.96 (m, 5H), 1.60 (d, J=6.7 Hz, 3H). MS (ESI) m/z 574.1 (M+H)$^+$.

Comparative Example B (S)-1-(6-(2H-1,2,3-triazol-2-yl)-5-(trifluoromethyl)pyridin-3-yl)-3-(7-(1-methoxyethyl)-2-methylthiazolo[5,4-b]pyridin-6-yl)urea Comparative Example B was prepared as described in WO2018020474, Compound 142.

Biological Assays

MALT-1 Biochemical Assay

A Quenched Fluorescence Resonance Energy Transfer (Quench-FRET) enzyme assay was used to test the ability of exemplary MALT-1 inhibitors Example 1 to Example 39 to inhibit the cleavage of a MALT1 specific quenched fluorescent substrate of sequence [TAMRA-PEG2-Leu-Val-Ser-Arg-Gly-Ala-Ala-Ser-PEG2-K(QSY7) by human MALT-1 protein; where TAMRA is 6-carboxytetramethylrhodamine, PEG2 is 2-(2-(2-aminoethoxy)ethoxyamide linker, QSY7 is a non-fluorescent quenching dye (Thermo-Fisher catalog #Q10193). The assay was performed by pre-dispensing compounds into 384 well Proxiplates™ (PE 6008289). Human MALT-1 (6 nM) was prepared using the assay buffer (25 mM HEPES pH 7.5, 1 mM ethylenediaminetetraacetic acid, 0.8 M sodium citrate, 0.005% Bovine serum albumin (BSA), 2 mM dithiothreitol (DTT)) and added to the compound plates. The plates were incubated 40 minutes at room temperature. The reaction was carried out by adding the substrate (2 μM) to the plates and incubating for 60 minutes at room temperature. A fluorescence readout was then measured using a PE EnVision® reader (Ex.535/Em.590). The results of the enzyme assay are provided subsequently in Table 2 and demonstrate the ability of the compounds of the present disclosure to inhibit MALT-1 protease activity. $EC_{50}$ is defined as the half maximal effective concentration of compound to inhibit MALT-1 protease activity.

TABLE 2

| Example | Enzyme Activity $EC_{50}$ (μM) |
|---|---|
| 1 | 0.091 |
| 2 | 0.19 |
| 3 | 0.11 |
| 4 | 0.158 |
| 5 | 0.077 |
| 6 | 0.146 |
| 7 | 0.135 |
| 8 | 0.099 |
| 9 | 0.102 |
| 10 | 0.198 |
| 11 | 0.155 |
| 12 | 0.061 |
| 13 | 0.193 |
| 14 | 0.097 |
| 15 | 0.103 |
| 16 | 0.106 |
| 17 | 0.092 |
| 18 | 0.284 |
| 19 | 0.198 |
| 20 | 0.12 |
| 21 | 0.141 |
| 22 | 0.228 |
| 23 | 0.139 |
| 24 | 0.979 |
| 25 | 0.067 |
| 26 | 0.393 |
| 27 | 0.07 |
| 28 | 0.138 |
| 29 | 0.232 |
| 30 | 0.082 |
| 31 | 0.082 |
| 32 | 0.113 |
| 33 | 0.162 |

TABLE 2-continued

| Example | Enzyme Activity EC$_{50}$ (μM) |
|---|---|
| 34 | 0.112 |
| 35 | 0.5 |
| 36 | 0.048 |
| 37 | 0.06 |
| 38 | 0.156 |
| 39 | 0.083 |

MALT-1 Cell IL-6 AlphaLISA Assay

The following MALT-1 Cell Interleukin-6 (IL-6) AlphaLISA assay was conducted using a Perkin Elmer® IL-6 AlphaLISA® detection kit (PE AL223). The IL-6 detection assay is a homogeneous immunoassay that detects human IL-6 present in the cell culture medium in the MALT-1 dependent human ABC-DLBCL cell line, OCI-LY3. Compounds were pre-dispensed into Black 384w microtiter plates (Greiner, 781090) from 30 μM to 1.5 nM. Viable OCI-LY3 cells were then seeded on top of compounds at a seeding density of 50,000 cells/mL. Plates were then placed into 37° C. incubators for 48 hours. After 48 hours incubation, 2 μL of cell medium from each well was transferred into white ProxiPlates™ (PE 6008289). A fresh mix of AlphaLISAAcceptor beads (10 μg/mL) and Biotinylated IL-6 Antibody (1 nM) was made in AlphaLISA Immunoassay buffer and added to all wells (4 μL). The plates were incubated for 60 minutes at room temperature. Streptavidin donor beads (40 μg/mL) were prepared using the assay buffer and added to all wells (5 μL). The plates were incubated for 30 minutes at room temperature and read using PE EnVision® reader. Results are shown in Table 3.

TABLE 3

| Example | OCI-LY3 IL6 48 hour Inhibition EC$_{50}$ (μM) |
|---|---|
| 1 | 0.2 |
| 2 | 0.11 |
| 3 | 0.14 |
| 4 | 1.33 |
| 5 | 0.34 |
| 6 | 0.21 |
| 7 | 0.14 |
| 8 | 0.07 |
| 9 | 0.14 |
| 10 | 0.23 |
| 11 | 0.39 |
| 12 | 0.2 |
| 13 | 0.42 |
| 14 | 0.2 |
| 15 | 0.3 |
| 16 | 0.47 |
| 17 | 0.58 |
| 18 | 1.15 |
| 19 | 0.95 |
| 20 | 0.18 |
| 21 | 0.67 |
| 22 | 0.38 |
| 23 | 0.21 |
| 24 | 12.2 |
| 25 | 0.25 |
| 26 | 1.15 |
| 27 | 0.41 |
| 28 | 0.42 |
| 29 | 0.3 |
| 30 | 0.71 |
| 31 | 0.44 |
| 32 | 0.25 |
| 33 | 0.18 |
| 34 | 0.19 |
| 35 | 7.3 |
| 36 | 0.27 |
| 37 | 0.21 |
| 38 | 0.19 |
| 39 | 0.04 |

Cardiovascular Assay

The following cardiovascular assay was conducted using male Sprague-Dawley rats that were anesthetized with Inactin (thiobutabarbital), instrumented (catheterized both femoral artery and vein; catheterize left ventricular) and allowed to stabilize. Following a 30-minute baseline period, each compound was infused at low, medium, and high doses/30 minutes. Plasma samples were taken at the end of each dose infusion. If, at any point, the mean arterial pressure (MAP) of an animal decreased below 70 mmHg, the infusion was immediately stopped, a final blood sample was taken, and hemodynamic data for that animal was removed from the group average for all subsequent time points. A 1500 change from vehicle for MAP or heart rate (HR), respectively, is considered biologically relevant. A 200% change from vehicle for dP/dt@50 is considered biologically relevant. Results are shown in Table 4.

TABLE 4

| Example | Dose (mg/kg) | Drug (μg/mL SEM) | MAP (%) | HR (%) | dP/dt@50 (%) |
|---|---|---|---|---|---|
| 1 | 3 | 2.32 ± 0.12 | −5 | −4 | 5 |
|   | 10 | 9.36 ± 0.41 | −8 | −8 | 12 |
|   | 30 | 24.00 ± 1.63 | −16 | −17 | 11 |
| 3 | 3 | 2.18 ± 0.10 | 1 | −1 | 0 |
|   | 10 | 8.34 ± 0.55 | 0 | −3 | 3 |
|   | 30 | 22.87 ± 2.67 | −13 | −12 | −3 |
| 19 | 3 | 2.51 ± 0.29 | 0 | −5 | −5 |
|   | 10 | 8.92 ± 0.73 | −1 | −5 | −5 |
|   | 30 | 25.13 ± 0.98 | −2 | −9 | −3 |
| 33 | 3 | 2.52 ± 0.39 | −5 | −5 | 1 |
|   | 10 | 11.20 ± 0.60 | −5 | −7 | 1 |
|   | 30 | 34.10 ± 1.95 | −9 | −8 | 7 |
| Comparative Example A | 3 | 1.45 ± 0.06 | −10 | −7 | −4 |
|   | 10 | 5.15 ± 0.32 | −14 | −11 | −7 |
|   | 30 | 12.91 ± 1.71 | −22 | −18 | −6 |

CYP3A4 Induction Assay

CYP induction by compounds of the Examples was evaluated in vitro by determining the expression levels of CYP 3A4 mRNA using the qPCR (quantitative polymerase chain reaction) assay. On day one, cryopreserved human hepatocytes were thawed in prewarmed (37° C.) thawing medium (cryopreserved hepatocyte recovery medium, Gibco™ CM 7000; Thermo Fisher Scientific), centrifuged (1000 g for 10 minutes) and resuspended in plating medium (Gibco™ CM3000—Williams Medium E supplemented with hepatocytes plating supplement pak-serum containing; Thermo Fisher Scientific). Cells were counted by trypan blue exclusion using a hemocytometer and adjusted to a cell density of 1.2×10$^6$ cells/μL. Thereafter, 0.05 μL of cell suspension was aliquoted per well in a 96-well plate, resulting in 60,000 cells/well. Plates were shaken in the north-south and east-west direction during plating. Plated cells were incubated at 37° C./5% CO$_2$ in a humidified cell culture incubator for 4-6 hours. During this time, incubation medium (Gibco™ CM4000, cell maintenance supplement pack; Thermo Fisher Scientific) was mixed with Gibco™ Geltrex™ (Thermo Fischer Scientific) at the appropriate Geltrex™ protein concentration. Following recovery, medium was removed from cells and replaced with freshly prepared incubation medium. Cells were incubated overnight in a cell culture incubator (37° C./5% $CO_2$).

The next day the incubation medium was prepared by combining the hepatocyte maintenance supplement pack with Williams Medium E. The medium was warmed to 37° C. 1000× dimethyl sulfoxide compound stocks of the compounds of the Examples were prepared to the desired concentrations. 10 mM compound stocks in dimethyl sulfoxide were diluted (1 μL to 1 mL CM4000; final concentration=10 μM). Overlay medium was aspirated and 0.1 μL dose solution added to the desired labeled 96 well plate. Cells were then dosed with compound (10 μM) and prototypical induces at the targeted concentrations either 50 μM for omeprazole (Sigma 0104/lot BCBF-2161V) or 10 μM for rifampicin (Sigma R3501/lot 011M1159V). A negative control, probenecid, was dosed at 10 μM (Sigma P8761/lot 013K0148).

On day 3, RNA isolation was performed. All surfaces were cleaned using RNase RNAy. Total RNA was isolated using MagMAX Express 96 RNA Isolation System (Life Technologies, AM1830). Briefly, hepatocytes were washed once with 1×PBS (phosphate buffered saline). 145 μL of RNA Lysis Buffer was added to each well and each well was mixed by pipetting several times. Lysate was then transferred to a well of a 96 well Binding Plate. Samples were then mixed with 20 μL magnetic beads coming from the kit. RNA bound to beads was then captured by the magnetic tip manifold and beads were washed with the wash solution. Samples were treated with TURBO™ DNase. After TURBO™ DNase treatment, RNA was rebound to beads and washed with the provided wash buffer an additional two times. Beads are then dried, and RNA was eluted with 50 μL elution buffer. The eluted mRNA was transferred from the wells to RNase-free sealable microtiter plates and stored at −80° C. until use.

Following mRNA isolation, reverse transcription (RT) reactions were performed using Taqman™ Reverse Transcription Reagents (ThermoFisher Scientific). RT master mix was prepared by mixing 2.5 μL 10×RT buffer, 5.5 μL 25 mM $MgCl_2$, 5 μL deoxyNTP mixture, 1.25 μL 50 mM random hexamers, 0.5 μL 2×RNAse inhibitor, 0.625 μL multiscript RTase (50 U/μL) and 0.625 μL water. An aliquot of RT mix (16 μL) and an aliquot of mRNA sample (9 μL) was added to each well of a 96-well plate. The SimpliAmp™ Thermal cycler PCR System VIIA7 from Applied Biosystems was used for reverse transcription under the following conditions: segment 1: 25° C. for 10 minutes; segment 2: 45° C. for 45 minutes; segment 3: 95° C. for 5 minutes; and segment 4: 4° C. hold; with 1 cycle for each segment.

Thereafter, TaqMan™ qPCR was performed using Applied Biosystems QuantStudio 7 Flex System (Applied Biosystem, Foster City, CA). TaqMan™ Fast Advanced Master Mix and Gene expression assay primers (HS00604506_ml (ThermoFisher) for CYP3A4 and HS02758991_g1 hGAPDH (ThermoFisher) as control, glyceraldehyde-3-phosphate dehydrogenase) were purchased from Applied Biosystems. The PCR reaction mix included diluted cDNA (2 μL) and 18 μL of the TaqMan™ qPCR master mix (10 μL TaqMan™ Fast Advanced Master Mix, 1 μL of gene expression primer probe mix, 7 μL nuclease-free water). qPCR thermal cycling conditions: segment 1: 50° C. held for 10 minutes; segment 2: 95° C. held for 3 minutes; followed by 40 cycles of segment 3: 95° C. for 15 seconds and segment 4: 60° C. for 1 minute.

The fold induction in CYP isoform mRNA caused by treatment with the compounds was determined using the comparative quantitative real-time polymerase chain reaction (qPCR). This method calculated the CYP fold induction over vehicle (0.100 DMSO) and as a percentage of the response of the positive control, rifampicin. The fold induction=Fold of Treated/Fold of Vehicle Control. The percent of positive control=(Fold Induction of Treated−1)/(Fold Induction of Rifampicin−1).

TABLE 5

| Example | CYP3A4 Fold induction % of positive control (%) |
|---|---|
| 1 | 1.45 (5.46) |
| 2 | 1.13 (2.19) |
| 3 | 1.12 (1.75) |
| 4 | 1.98 (16.1) |
| 5 | 1.77 (15.3) |
| 6 | 1.4 (5.46) |
| 7 | 1.93 (12.7) |
| 8 | 1.53 (9.23) |
| 9 | 0.548 (−5.95) |
| 10 | 8.24 (84.8) |
| 11 | 2.59 (20) |
| 12 | 3.65 (31) |
| 13 | 3.19 (34.8) |
| 14 | 2.71 (27.3) |
| 15 | 0.413 (−4.74) |
| 16 | Not determined |
| 17 | Not determined |
| 18 | 2.8 (16.5) |
| 19 | 0.985 (−0.162) |
| 20 | 1.38 (4.08) |
| 21 | 1.29 (5.55) |
| 22 | 1.09 (1.16) |
| 23 | 0.677 (−4.35) |
| 24 | 1.49 (7.62) |
| 25 | 1.16 (2.45) |
| 26 | 1.17 (2.57) |
| 27 | 1.47 (7.55) |
| 28 | 2.24 (15.1) |
| 29 | 3.29 (27.8) |
| 30 | 1.49 (5) |
| 31 | 1.37 (4.87) |
| 32 | 1.2 (2.56) |
| 33 | 2.72 (20.2) |
| 34 | 2.11 (13) |
| 35 | 2.45 (17) |
| 36 | 1.9 (14.4) |
| 37 | 2.19 (19) |
| 38 | 2.72 (19.9) |
| 39 | 2.29 (14.9) |
| Comparative Example B | 2.32 (25.3) |

It is understood that the foregoing detailed description and accompanying examples are merely illustrative and are not to be taken as limitations upon the scope of the present disclosure, which is defined solely by the appended claims and their equivalents. Various changes and modifications to the disclosed embodiments will be apparent to those skilled in the art. Such changes and modifications may be made without departing from the spirit and scope thereof. All publications, patents, and patent applications cited herein are hereby incorporated by reference in their entirety for all purposes.

What is claimed is:

1. N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1λ⁶-thiane-4-carboxamide; or a pharmaceutically acceptable salt thereof.

2. N-{(1S)-1-[4-({7-[(1R)-2,2-difluoro-1-methoxyethyl]-2-methyl[1,3]thiazolo[5,4-b]pyridin-6-yl}amino)phenyl]-2,2,2-trifluoroethyl}-N-methyl-1,1-dioxo-1λ⁶-thiane-4-carboxamide.

* * * * *

UNITED STATES PATENT AND TRADEMARK OFFICE
CERTIFICATE OF CORRECTION

| | | |
|---|---|---|
| PATENT NO. | : 11,993,613 B2 | Page 1 of 1 |
| APPLICATION NO. | : 18/192810 | |
| DATED | : May 28, 2024 | |
| INVENTOR(S) | : Puneet Kumar et al. | |

It is certified that error appears in the above-identified patent and that said Letters Patent is hereby corrected as shown below:

In the Specification

In Column 25, Table 1, EX 36, delete

"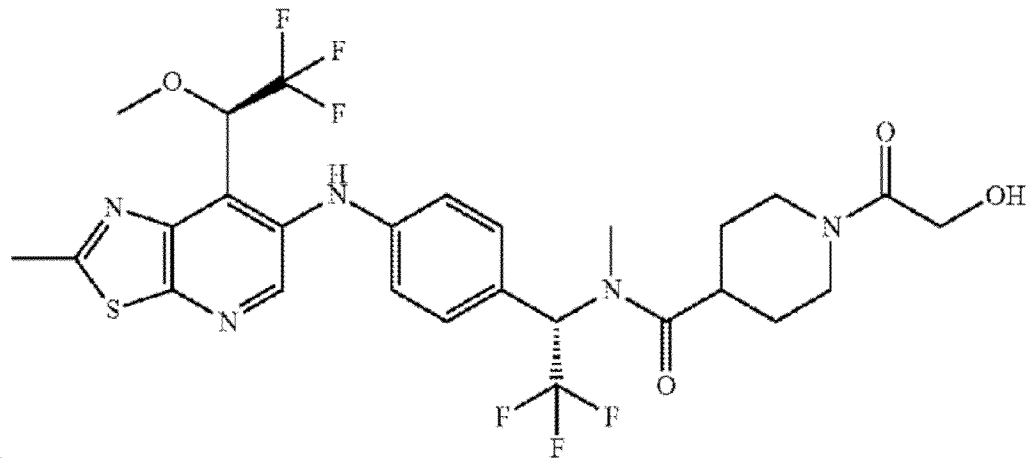" and insert

--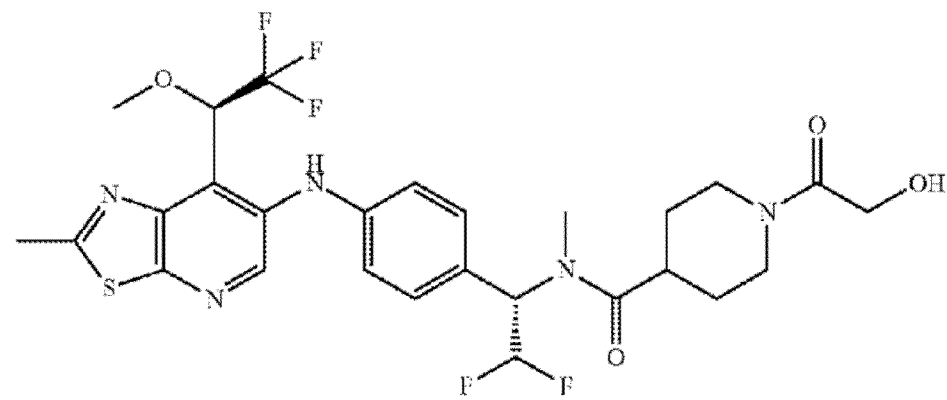--, therefor.

Signed and Sealed this
Sixth Day of January, 2026

John A. Squires
*Director of the United States Patent and Trademark Office*